(12) United States Patent
Murata et al.

(10) Patent No.: US 7,109,195 B2
(45) Date of Patent: Sep. 19, 2006

(54) HEXACYCLIC COMPOUNDS AND THEIR THERAPEUTIC USE

(75) Inventors: Takeshi Murata, Kamakura (JP); Satoshi Niizuma, Yokohama (JP); Nobuo Shimma, Chigasaki (JP); Hitomi Suda, Fujisawa (JP); Masao Tsukazaki, Fujisawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/942,044

(22) Filed: Sep. 16, 2004

(65) Prior Publication Data

US 2005/0059679 A1 Mar. 17, 2005

Related U.S. Application Data

(62) Division of application No. 10/304,672, filed on Nov. 26, 2002, now Pat. No. 6,825,194.

(30) Foreign Application Priority Data

Nov. 30, 2001 (EP) .................................. 01128361

(51) Int. Cl.
  *A61K 31/407* (2006.01)
  *C07D 491/22* (2006.01)
(52) U.S. Cl. .................. 514/233.2; 514/257; 544/115; 544/245
(58) Field of Classification Search ............. 514/233.2, 514/257; 544/115, 245
  See application file for complete search history.

(56) References Cited

FOREIGN PATENT DOCUMENTS

| EP | 0 074 256 | 3/1983 |
|---|---|---|
| EP | 0 296 597 | 12/1988 |
| EP | 0 471 358 | 2/1992 |
| EP | 0 495 432 | 7/1992 |
| WO | WO 95/22549 | 8/1995 |
| WO | WO 96/38146 | 12/1996 |
| WO | WO 98/35940 | 8/1998 |
| WO | WO 99/05103 | 2/1999 |

OTHER PUBLICATIONS

Wall et al., J. Am. Chem. Soc., vol. 88, 1966, pp. 3888-3890.
Kingsbury et al., J. Med. Chem., vol. 34, 1991, pp. 98-107.
Kunimoto et al., Cancer Research, vol. 47, 1987, pp. 5944-5947.
Vey et al., Clin. Cancer Res., vol. 6, 2000, pp. 731-736.
Wani et al., J. Med. Chem., vol. 29, 1986, pp. 2358-2363.
Bedeschi et al., Med. Chem. Lett., vol. 6, No. 6, 1996, pp. 671-674, XP002239568.
Sugimori et al., J. Med. Chem., vol. 41, No. 13, 1998, pp. 2308-2318, XP002239569.
Patent Abstracts of Japan, vol. 018, No. 347, 1994, & JP 06-087746, Yakult Honsha Co., Ltd.
Sugimori et al., J. Med. Chem. vol. 37, No. 19, 1994, pp. 3033-3039, XP002239570.
Simone, Oncology, Introduction, Cecil Textbook of Medicine, 20th Edition, vol. 1, 1996, pp. 1004-1010.

*Primary Examiner*—Deepak Rao
(74) *Attorney, Agent, or Firm*—Foley & Lardner LLP

(57) ABSTRACT

The present invention relates to hexacyclic compound of the formula [1],

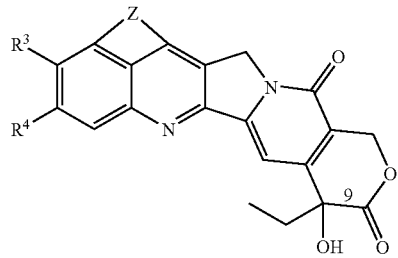

wherein Z, $R^3$ and $R^4$ are as identified therein, and pharmaceutically acceptable salts thereof. These compounds are useful in the treatment of cell proliferative disorders.

7 Claims, No Drawings

HEXACYCLIC COMPOUNDS AND THEIR THERAPEUTIC USE

This application is a divisional of U.S. application Ser. No. 10/304,672 filed Nov. 26, 2002 now U.S. Pat. No. 6,825,194.

FIELD OF THE INVENTION

The present invention is related to a novel hexacyclic compound of formula [1],

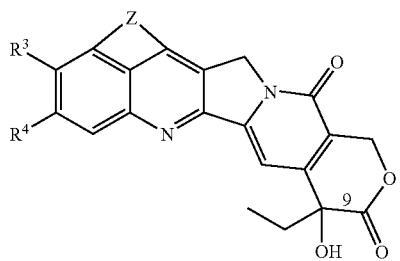

[1]

wherein

Z, $R^3$ and $R^4$ are as defined below. These compounds have antitumor activities and are useful in the treatment of cancer. The invention also relates to pharmaceutical compositions containing an amount of a compound of formula [1], as well as to a method of treating cancer comprising administering a therapeutically effective amount of a compound of formula [1].

BACKGROUND OF THE INVENTION

4(S)-ethyl-4-hydroxy-1H-pyrano[3',4':6,7]indolizino[1,2-b]quinoline-3,14(4H,12H)-dione (camptothecin), a pentacyclic alkaloid isolated from the Chinese tree *Camptotheca acuminata*, was first discovered in 1960's by Wall et al. as an anti-tumor agent (Wall, M. E. et al. Plant tumor antigens. I. The isolation and structure of camptothecin, a novel alkaloidal leukemia and tumor inhibition from *Camptotheca acuminata*. J. Am. Chem. Sco., 88:3888–3890, 1966). Cytotoxic activity of camptothecin is attributable to its ability to interfere with DNA topoisomerase I (Hsiang, Y.-H. et al. Campiothecin induces protein-linked DNA breaks via mammalian DNA topoisomerase I. J. Biol. Chem., 260:14873–14878, 1985). DNA topoisomerase I is a phosphorylated protein and is required for DNA replication, transcription and recombination. It forms a covalent reversible DNA topoisomerase I-double strand DNA complex (referred to as cleavable complex) and relaxes supercoiled DNA by cleaving and religating one of the two DNA strands (Wang, J. C. DNA topoisomerases. Annu. Rev. Biochem. 54:665–697, 1985; Champoux, J. J. Mechanistic aspects of type-I topoisomerase. In "DNA topology and its biological effects" pp. 217–242, 1990; Wang, J. C. et al. The role of DNA topoisomerase in recombination and genome stability: A double-edged sword? Cell 62:403–406, 1990; Muller, M. T. Quantification of eukaryotic topoisomerase reactivity with DNA. Preferential cleavage of supercoiled DNA. Biochim. Biophys. Acta. 824:263–267, 1985). Camptothecin reversibly interacts with the cleavable complex and subsequently induces DNA single strand breaks by interfering with the religation step (Hsiang, Y.-H. et al. Camptothecin induces protein-linked DNA DNA brasks via mammalian DNA topoisomerase I. J. Biol. Chem., 260:14873–14878, 1985; Porter, S. E. et al. The basis for camptothecin enhancement of DNA breakage by eukaryotic DNA topoisomerase I. Nucleic Acid Res. 17:8521–8532, 1989). Unlike DNA topoisomerase II, DNA topoisomerase I-mediated relaxation of DNA occurs independently of nucleotide cofactor, or divalent cations.

Although DNA topoisomerase I is an ubiquitous enzyme and is present throughout the cell cycle, antiproliferative activities of camptothecin are only limited to clinical trials, and half-life in plasma of camptothecin appeared to be short (less than 30 min) being converted to the inactive carboxylate form. Furthermore, campthotecin is poorly soluble in water, and therefore, it itself can not be formulated for the use of intravenous injection. A number of camptothecin derivatives were synthesized to improve anti-tumor activity, lactone stability in plasma and/or water solubility, and were tested clinically (Gerrits, C. J. H., de Jonge, M. J. et al. Topoisomerase I inhibitors: the relevance of prolonged exposure for clinical development. Br. J. Cancer, 76: 952–962, 1997; O'Leary, J. et al. Camptothecins: a review of their development and schedules of administration. Eur. J. Cancer, 34: 1500–1508, 1988; Gerderblom, H. A. et al. Oral topoisomerase I inhibitors in adults patients: present and future. Investig. New Drugs, 17: 401–415, 1999). However, at the present time, only two campthotecin derivatives, 7-ethyl-10-[4-(1-piperidino)-1-piperidino]carbonyloxy-camptothecin (irinotecan) that is the prodrug of 7-ethyl-10-hydroxycamptothecin (SN-38, EP 0074256) and 9-(dimethylamino)methyl-10-hydroxycamptothecin (topotecan) have been introduced to for the clinical practice (Kunimoto, T. et al. Antitumor activity of 7-ethyl-10-[4-(1-piperidino)-1-piperidino]carbonyloxy-camptothecin, a novel water-soluble derivative of camptothecin, against murine tumors. Cancer Res., 47:5944–5947, 1987; Kingsbury, W. D. et al. Synthesis of water-soluble (aminoalkyl)camptothecin analogs: inhibition of topoisomerase I and antitumor activity. J. Med. Chem., 34:98–107, 1991).

Due to its complexities of the synthetic routes, there is clearly a limitation for producing camptothecin. As was the case of irinotecan or topotecan, large majority of the camptothecin analogues were the camptothecin derivatives having substituents on the A-ring or B-ring independently. Such camptothecin derivatives include 9-nitrocamptothecin (Pantazis, P. et al. The role of pH and serum albmin in the metabolic conversion of 9-nitrocamptothecin to 9-aminocamptothecin by human hematopoietic and other cells. Eur. J. Hematol., 55:211–213, 1995; Loos, W. J. et al. Determination of the lactone and lactone plus carboxylate forms of 9-aminocamptothecin in human plasma by sensitive high-performance liquid chromatography with fluorescent detection. J. Chromatogr. B., 694: 435–441, 1997; Blaney, S. M. et al. Plasma and cerebrospinal fluid pharmacokinetics of 9-aminocamptothecin (9-AC), irinotecan, and SN-38 in nonhuman primates. Cancer Chemother. Pharmacol., 41: 464–468, 1998), and lurtotecan (Emerson, D. L. et al. In vitro anti-tumor activity of two new seven-substituted water-soluble camptothecin analogues. Cancer Res., 55: 603–609, 1955).

Few derivatives, such as (1S,9S)-1-amino-9-ethyl-5-fluoro-9-hydroxy-4-methyl-2,3,9,10,13,15-hexahydro-1H, 12H-benzo[de]pyrano[3',4':6,7]indolizino[1,2-b]quinoline-10,13(9H,15H)-dione methanesulfonate (DX-8951f), having the F-ring over the A- and B-ring were also reported to possess potent anti-tumor activities' both in vitro and in vivo (Vey, N. et al. The topoisomerase I inhibitor DX-8951f is active in a severe combined immunodeficient mouse model of human acute myelogenous leukemia. Clin. Cancer Res., 6:731–736, 2000). However, the F-ring introduced to the particular position is restricted to a saturated hydrocarbon chain with or without a heteroatom involved in the chain due to the limitations of their synthetic routes.

Based on the deficiencies of the prior art, there are still strong needs to discover new synthetic routes and deliver of new camptothecin analogs with improved activities against wide variety of tumor cells.

SUMMARY OF THE INVENTION

In accordance with the present invention it has found that the novel hexacyclic compounds show antitumor activity. The present invention is directed to these novel hexacyclic compounds having potent anti-tumor activity, a process for producing the same, pharmaceutical compositions containing said compounds and processes for producing the novel hexacyclic compounds.

It is an aspect of the present invention to provide hexacyclic compounds of the formula [1],

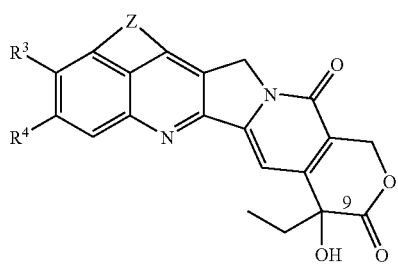

[1]

wherein
Z is —NH—C(=X)—N($R^1$)— or —N=C($R^2$)—N($R^1$)—;
$R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino;
$R^2$ is hydrogen; amino; (C1–C5) alkyl; (C1–C5) alkoxy; (C1–C5) alkylthio; mono-(C1–C5) alkylamino; di-(C1–C5) alkylamino optionally substituted with one to three moieties independently selected from the group consisting of (C1–C5) alkoxy, hydroxy, halogen, amino, (C3–C7) cycloalkyl, heterocyclic ring or an aryl ring in which the aryl ring is optionally substituted with one to three moieties independently selected from the group consisting of hydroxy, (C1–C5) alkoxy, amino, mono-(C1–C5) alkylamino and di-(C1–C5) alkylamino;
$R^3$ and $R^4$ are independently hydrogen, halogen or (C1–C5) alkyl; and
X is oxygen or sulfur;

or a pharmaceutically acceptable salt thereof.

A more specific aspect of the present invention is provide hexacyclic compounds of the formula [1A],

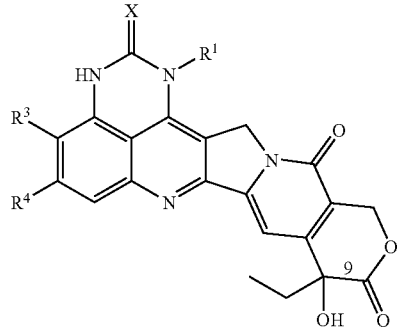

[1A]

wherein X is oxygen and $R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino; and
$R^3$ and $R^4$ are independently hydrogen, halogen or (C1–C5) alkyl; or a pharmaceutically acceptable salt thereof.

Another aspect of the present invention to provide hexacyclic compounds of the formula [1B],

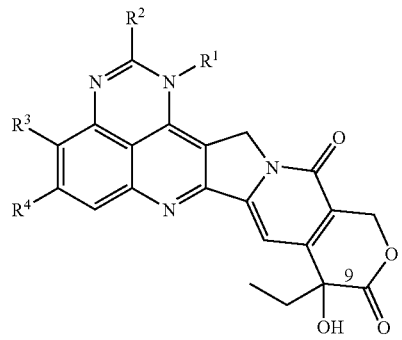

[1B]

wherein $R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino;
$R^2$ is hydrogen; amino; (C1–C5) alkyl; (C1–C5) alkoxy; (C1–C5) alkylthio; mono-(C1–C5) alkylamino; di-(C1–C5) alkylamino optionally substituted with one to three moieties independently selected from the group consisting of (C1–C5) alkoxy, hydroxy, halogen, amino, (C3–C7) cycloalkyl, heterocyclic ring and an aryl ring in which the aryl ring is optionally substituted with one to three moieties independently selected from the group consisting of hydroxy, (C1–C5) alkoxy, amino, mono-(C1–C5) alkylamino or di-(C1–C5) alkylamino;

$R^3$ and $R^4$ are independently hydrogen, halogen or (C1–C5) alkyl; and or a pharmaceutically acceptable salt thereof.

It is yet another aspect of the present invention to provide pharmaceutical composition containing the above compounds.

A still further aspect of the present invention is to provide a process for the preparation of the above hexacyclic compounds.

DETAILED DESCRIPTION OF THE INVENTION

Unless otherwise indicated, the following definitions are set forth to illustrate and defined the meaning and scope of the various terms used to describe the invention herein.

The term "alkyl" refers a straight or branched monovalent saturated aliphatic hydrocarbon group. (C1–C10) alkyl" means a straight chain or branched hydrocarbon chain having 1 to 10, preferably 1 to 8 carbon atom(s), e.g. methyl, ethyl, propyl, isopropyl, butyl, isobutyl, ter-butyl, sec-butyl, pentyl, 1-methylbutyl, 2-methylbutyl, 3-methylbutyl, 1,1-dimethylpropyl, 2,2-dimethylpropyl, 1-ethylpropyl, hexyl, 1-methylpentyl, 2-methylpentyl, 3-methylpentyl, 4-methylpentyl, 2,2-dimethylbutyl, 2,3-dimethylbutyl, 3,3-dimethylbutyl and the like, more preferably butyl, isobutyl, 3-methylbutyl, pentyl and the like. "(C1–C5)alkyl" preferably means methyl, ethyl, propyl, isopropyl, butyl, isobutyl, ter-butyl, sec-butyl, pentyl, 1-methylbutyl, 2-methylbutyl, 3-methylbutyl as the like, more preferably methyl, ethyl, propyl and the like.

The term "alkoxy" refers to the group —O—R', wherein R' is an alkyl group as defined above. "(C1–C5)alkoxy" preferably means methoxy, ethoxy, propoxy, isopropoxy, butoxy, isobutoxy, tert-butoxy, pentoxy, 3-methylbutoxy, 2,2-dimethylpropoxy and the like.

The term "hydroxy" refers to the group HO—.

The term "halogen" refers to fluoro, chloro, bromo and iodo.

The term "amino" refers to the group —NH$_2$ and includes amino groups which are protected by a group known in the art such as a formyl, acetyl, trithyl, tert-butoxycarbonyl, benzyl, benzyloxycarbonyl, and the like. Preferably, "amino" means —NH$_2$.

The term "mono-alkylamino" refers to the group —NH—R', wherein R' is an alkyl group as defined above, and includes amino groups which are protected by a group known in the art such as a formyl, acetyl, trithyl, tert-butoxycarbonyl, benzyl, benzyloxycarbonyl, and the like. The term "mono-(C1–C5)alkylamino" preferably means N-methylamino, N-ethylamino, N-propylamino, N-isopropylamino, N-butylamino, N-(1-methylpropyl)amino, N-(2-methylpropyl)amino, N-pentylamino, and the like, more preferably N-ethylamino, N-propylamino, N-butylamino and the like.

The term "di-alkylamino" refers to the group —NR'R", wherein R' and R" are (independently from each other) an alkyl group as defined above. "di-(C1–C5)alkylamino" preferably means N,N-dimethylamino, N,N-diethylamino, N,N-dipropylamino, N,N-diisopropylamino, N,N-dibutylamino, N-methyl-N-ethylamino, N-methyl-N-propylamino and the like, more preferably N,N-dimethylamino, N,N-diethylamino.

The term "(C3–C7)cycloalkyl" means 3 to 7 membered ring, which do not contain any heteroatoms in the ring. "Cycloalkyl" preferably means cyclopropyl, cyclobutyl, cyclopentyl, cyclohexyl, cycloheptyl and the like, more preferably cyclopentyl and cyclohexyl.

The term "heterocyclic ring" refers a 3 to 10 membered ring which contains one or more heteroatom(s) selected from N, S and O, preferably oxazolyl, thiazolyl, 4,5-dihydro-oxazolyl, 4,5-dihydro-thiazolyl, furyl, pyrrolyl, thienyl, imidazolyl, triazolyl, tetrazolyl, pyridyl, pyrazinyl, pyrimidinyl, triazinyl, oxadiazolyl, thiadiazolyl, pyrrolidinyl, tetrahydrothienyl, tetrahydrofuryl, morpholinyl, piperidyl, piperazinyl, 1-methylpiperazinyl and the like, more preferably imidazolyl, pyridyl, morpholinyl and pyrrolidinyl.

The term "aryl" means an aromatic carbocyclic group, i.e. a 6 or 10 membered aromatic or partially aromatic ring, e.g. phenyl, naphthyl or tetrahydronaphthyl, preferably phenyl or naphthyl, and most preferably phenyl.

The term "(C1–C5)alkylthio" refers to the group R'—S—, wherein R' is an (C1–C5)alkyl as defined above, preferably methyl, ethyl, propyl, isopropyl and the like, more preferably methyl and ethyl.

In the present invention, the expression "optionally substituted with" means that substitution can occur at one to three positions, preferably at one position, and, unless otherwise indicated, that the substituents are independently selected from the specified options.

The term "pharmaceutically acceptable," such as pharmaceutically acceptable carrier, excipient, prodrug, etc., means pharmacologically acceptable and substantially nontoxic to the subject to which the particular compound is administered.

The term "pharmaceutically acceptable salt" refers to conventional acid-addition salts or base-addition salts which retain the biological effectiveness and properties of the hexacyclic compounds of formula [1] and are formed from suitable non-toxic organic or inorganic acids or organic or inorganic bases. The acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid and the like. The base-addition salts include those derived from potassium, sodium, ammonium, and quarternary ammonium hydroxide, such as for example tetramethylammonium hydroxide.

In the above definitions, the preferable embodiments of $R^1$ are methyl, ethyl, propyl, isopropyl, butyl, isobutyl, pentyl, 3-methylbutyl, 2,2-dimethylpropyl, 1-ethylpropyl, hexyl, 4-methylpentyl, 3,3-dimethylbutyl, heptyl, 2-methoxyethyl, 2-ethoxyethyl, 2-propoxyethyl, 3-methoxypropyl, 4-methoxybutyl, 2-hydroxyethyl, 3-hydroxypropyl, 4-hydroxybutyl, 5-hydroxypentyl, 2-fluoroethyl, 3-fluoropropyl, 4-fluorobutyl, 2-chloroethyl, 3-chloropropyl, 4-chlorobutyl, 2-(dimethylamino)ethyl, 3-(dimethylamino)propyl, 2-(cyclohexyl)ethyl, 2-(4-morpholino)ethyl, 2-(pyyrrolidino)ethyl, 2-(piperidino)ethyl, 2-(4-methylpiperazino)ethyl, 2-(pyridin-2-yl)ethyl, 2-(pyridin-3-yl)ethyl, 2-(imidazol-1-yl)ethyl, benzyl, phenethyl, 2-(1-naphthyl)ethyl, 3-phenylpropyl, 2-(4-fluorophenyl)ethyl, 2-(4-chlorophenyl)ethyl, 2-(4-methoxyphenyl)ethyl, 2-(4-hydroxyphenyl)ethyl, 2-[4-(dimethylamino)phenyl]ethyl, 2-(3,4-methyenedioxyphenyl)ethyl and the kile, more preferably methyl, ethyl, propyl, isopropyl, butyl, isobutyl, pentyl, 3-methylbutyl, hexyl, 3,3-dimethylbutyl, heptyl, 2-hydroxyethyl, 3-hydroxypropyl, 2-(dimethylamino)ethyl, 3-(dimethylamino)propyl, 2-(4-morpholino)ethyl, 2-(pyridin-2-yl)ethyl, 2-(pyridin-3-yl)ethyl, benzyl, phenethyl, 3-phenylpropyl, 2-(4-fluorophenyl)ethyl, 2-(4-chlorophenyl)ethyl, 2-(4-methoxyphenyl)ethyl and the like.

The preferable embodiments of $R^2$ are hydrogen, methyl, ethyl, propyl, isopropyl, butyl, pentyl, hydroxymethyl, methoxymethyl, acetoxymethyl, aminomethyl, (methylamino)methyl, (dimethylamino)methyl, fluoromethyl, chloromethyl, trifluoromethyl, phenyl, pyridin-2-yl, methoxy, ethoxy, methylthio, ethylthio, amino, methylamino, ethylamino, propylamino, butylamino, dimethylamino, diethylamino and the like, and more preferably hydrogen, methyl, ethyl, propyl, hydroxymethyl, aminomethyl, chloromethyl, trifluoromethyl, methoxy, methylthio, ethylthio, methylamino, butylamino and dimethylamino.

In more detail the present invention refers to hexacyclic compounds of formula [1],

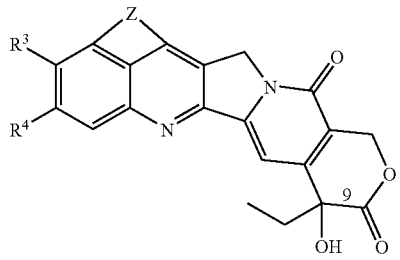

[1]

wherein

Z is —NH—C(=X)—N($R^1$)— or —N=C($R^2$)—N($R^1$)—;

$R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino;

$R^2$ is hydrogen; amino; (C1–C5) alkyl; (C1–C5) alkoxy; (C1–C5) alkylthio; mono-(C1–C5) alkylamino, di-(C1–C5) alkylamino optionally substituted with one to three moieties independently selected from the group consisting of (C1–C5) alkoxy, hydroxy, halogen, amino, (C3–C7) cycloalkyl, heterocyclic ring or an aryl ring in which the aryl ring is optionally substituted with one to three moieties independently selected from the group consisting of hydroxy, (C1–C5) alkoxy, amino, mono-(C1–C5) alkylamino and di-(C1–C5) alkylamino;

$R^3$ and $R^4$ are independently hydrogen, halogen or (C1–C5) alkyl; and

X is oxygen or sulfur;

or a pharmaceutically acceptable salt thereof.

In a preferred embodiment of the present invention, the stereochemistry of position 9 of the compound of the formula [1] is S configuration Preferred compounds of the present invention are those of formula [1A],

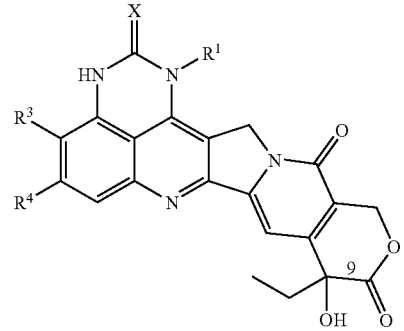

[1A]

wherein X is oxygen;

$R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino; (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino; and $R^3$ and $R^4$ are independently hydrogen, halogen or (C1–C5) alkyl;

or a pharmaceutically acceptable salt thereof. The invention preferably refers to compounds of formula [1A], wherein $R^1$ is hydrogen; or (C1–C8) alkyl optionally substituted with one or three moieties independently selected from the group consisting of (C1–C3) alkoxy, hydroxy, halogen, amino, mono-(C1–C3) alkylamino, di-(C1–C3) alkylamino, (C3–C7) cycloalkyl, a heterocyclic ring and an aryl ring in which the aryl ring is optionally substituted with one to three moieties independently selected from the group consisting of hydroxy, alkoxy and halogen; and $R^3$ and $R^4$ are hydrogen. Even more preferably $R^1$ in compounds of formula [1A] is (C1–C8)alkyl, phenyl-(C1–C8) alkyl, heterocyclic ring-(C1–C8)alkyl, alkoxyphenyl(C1–C8)alkyl or halogenphenyl(C1–C8)alkyl, and most preferably $R^1$ in compounds of formula [1A] is methyl, ethyl, n-propyl, 1-methylethyl, n-butyl, 1,1-dimethylethyl, 2-methylpropyl, 2,2-dimethylpropyl, n-pentyl, 3-methylbutyl, 2-n-hexyl, 3,3-dimethylbutyl, n-heptyl, n-octyl, benzyl, phenethyl, 2-(dimethylamino)ethyl, 2-(4-morpholino)ethyl, 3-(dimethylamino)propyl, 2-(pyridin-2-yl)ethyl, 2-(pyridin-3-yl)ethyl, 2-(4-methoxyphenyl)ethyl, 2-(4-chlorophenyl)ethyl, 2-(4-fluorophenyl)ethyl or 3-phenylpropyl.

Examples for these compounds are
a) (9S)-1-butyl-9-ethyl-9-hydroxy-1H,12H-pyrano[3",4":6',7']indolizino[1',2':6,5]pyrido[4,3,2-de]quinazoline-2,10,13(3H,9H,15H)-trione;
b) (9S)-9-ethyl-9-hydroxy-1-[2-(4-morpholino)ethyl]-1H,12H-pyrano[3",4":6',7']indolizino[1',2':6,5]pyrido[4,3,2-de]quinazoline-2,10,13(3H,9H,15H)-trione hydrochloride;
c) (9S)-1-[3-(dimethylamino)propyl]-9-ethyl-9-hydroxy-1H,12H-pyrano[3",4":6',7']indolizino[1',2':6,5]pyrido[4,3,2-de]quinazoline-2,10,13(3H,9H,15H)-trione hydrochloride;
d) (9S)-9-ethyl-9-hydroxy-1-phenetyl-1H,12H-pyrano[3",4":6',7']indolizino[1',2':6,5]pyrido[4,3,2-de]quinazoline-2,10,13(3H,9H,15H)-trione;

e) (9S)-9-ethyl-9-hydroxy-1-[2-(pyridin-2-yl)ethyl]-1H,12H-pyrano[3",4":6',7']indolizino[1',2':6,5]pyrido[4,3,2-de]quinazoline-2,10,13(3H,9H,15H)-trione hydrochloride;

f) (9S)-9-ethyl-1-heptyl-9-hydroxy-1H,12H-pyrano[3",4":6',7']idolizino[1',2':6,5]pyrido[4,3,2-de]quinazoline-2,10,13(3H,9H,15H)-trione;

g) (9S)-9-ethyl-9-hydroxy-1-propyl-1H,12H-pyrano[3",4":6',7']indolizino[1',2':6,5]pyrido[4,3,2-de]quinazoline-2,10,13(3H,9H,15H)-trione;

h) (9S)-9-ethyl-9-hydroxy-1-[2-(pyridin-3-yl)ethyl]-1H,12H-pyrano[3",4":6',7']indolizino[1',2':6,5]pyrido[4,3,2-de]quinazoline-2,10,13(3H,9H,15H)-trione hydrochloride;

i) (9S)-9-ethyl-9-hydroxy-1-(3-phenylpropyl)-1H,12H-pyrano[3",4":6',7']indolizino[1',2':6,5]pyrido[4,3,2-de]quinazoline-2,10,13(3H,9H,15H)-trione;

j) (9S)-9-ethyl-9-hydroxy-1-(2-methylpropyl)-1H,12H-pyrano[3",4":6',7']indolizino[1',2':6,5]pyrido[4,3,2-de]quinazoline-2,10,13(3H,9H,15H)-trione;

k) (9S)-9-ethyl-1-hexyl-9-hydroxy-1H,12H-pyrano[3",4":6',7']indolizino[1',2':6,5]pyrido[4,3,2-de]quinazoline-2,10,13(3H,9H,15H)-trione;

l) (9S)-9-ethyl-9-hydroxy-1-pentyl-1H,12H-pyrano[3",4":6',7']indolizino[1',2':6,5]pyrido[4,3,2-de]quinazoline-2,10,13(3H,9H,15H)-trione;

m) (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-2,10,13(3H,9H,15H)-trione;

n) (9S)-1-benzyl-9-ethyl-9-hydroxy-1H,12H-pyrano[3",4":6',7']indolizino[1',2':6,5]pyrido[4,3,2-de]quinazoline-2,10,13(3H,9H,15H)-trione;

o) (9S)-9-ethyl-9-hydroxy-1-(3-methylbutyl)-1H,12H-pyrano[3",4":6',7']indolizino[1',2':6,5]pyrido[4,3,2-de]quinazoline-2,10,13(3H,9H,15H)-trione;

p) (9S)-1,9-diethyl-9-hydroxy-1H,12H-pyrano[3",4":6',7']indolizino[1',2':6,5]pyrido[4,3,2-de]quinazoline-2,10,13(3H,9H,15H)-trione;

q) (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-2,10,13(3H,9H,15H)-trione;

r) (9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-2,10,13(3H,9H,15H)-trione;

s) (9S)-9-ethyl-9-hydroxy-1-(1-methylethyl)-1H,12H-pyrano[3",4":6',7']indolizino[1',2':6,5]pyrido[4,3,2-de]quinazoline-2,10,13(3H,9H,15H)-trione; and t) (9S)-1-(3,3-dimethylbutyl)-9-ethyl-9-hydroxy-1H,12H-pyrano[3",4":6',7']indolizino[1',2':6,5]pyrido[4,3,2-de]quinazoline-2,10,13(3H,9H,15H)-trione.

The most preferred compounds are a) (9S)-1-butyl-9-ethyl-9-hydroxy-1H,12H-pyrano[3",4":6',7']indolizino[1',2':6,5]pyrido[4,3,2-de]quinazoline-2,10,13(3H,9H,15H)-trione;

b) (9S)-9-ethyl-9-hydroxy-1-phenetyl-1H,12H-pyrano[3",4":6',7']indolizino[1',2':6,5]pyrido[4,3,2-de]quinazoline-2,10,13(3H,9H,15H)-trione;

c) (9S)-9-ethyl-9-hydroxy-1-(2-methylpropyl)-1H,12H-pyrano[3",4":6',7']indolizino[1',2':6,5]pyrido[4,3,2-de]quinazoline-2,10,13(3H,9H, 15H)-trione;

d) (9S)-9-ethyl-1-hexyl-9-hydroxy-1H,12H-pyrano[3",4":6',7']indolizino[1',2':6,5]pyrido[4,3,2-de]quinazoline-2,10,13(3H,9H, 15H)-trione;

e) (9S)-9-ethyl-9-hydroxy-1-pentyl-1H,12H-pyrano[3",4":6',7']indolizino[1',2':6,5]pyrido[4,3,2-de]quinazoline-2,10,13(3H,9H,15H)-trione;

f) (9S)-9-ethyl-9-hydroxy-1-(3-methylbutyl)-1H,12H-pyrano[3",4":6',7']indolizino[1',2':6,5]pyrido[4,3,2-de]quinazoline-2,10,13(3H,9H, 15H)-trione;

g) (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-2,10,13(3H,9H,15H)-trione;

h) (9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-2,10,13(3H,9H,15H)-trione; and i) (9S)-1-(3,3-dimethylbutyl)-9-ethyl-9-hydroxy-1H,12H-pyrano[3",4":6',7']indolizino[1',2':6,5]pyrido[4,3,2-de]quinazoline-2,10,13(3H,9H,15H)-trione.

In another preferred embodiment the invention refers to compounds as defined above which are represented by formula [1A],

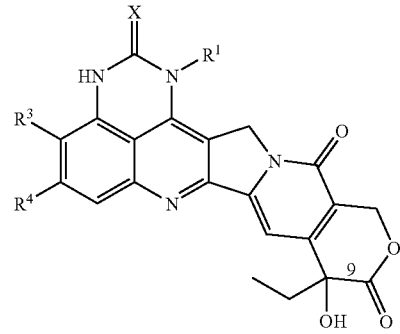

[1A]

wherein X is sulfur;

$R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino; and $R^3$ and $R^4$ are independently hydrogen, halogen or (C1–C5) alkyl;

or a pharmaceutically acceptable salt thereof. Preferably, the invention refers to compounds formula [1A] wherein $R^1$ is hydrogen or (C1–C8) alkyl optionally substituted with one to three moieties independently selected from the group consisting of (C1–C3) alkoxy, hydroxy, halogen, amino, mono-(C1–C3) alkylamino, di-(C1–C3) alkylamino, (C3–C7) cycloalkyl, a heterocyclic ring or an aryl ring in which the aryl ring is optionally substituted with one to three moieties independently selected from the group consisting of hydroxy, alkoxy or halogen; and $R^3$ and $R^4$ are hydrogen. More preferably $R^1$ is phenyl or (C1–C8) alkyl and most preferably $R^1$ is phenyl, 3-methylbutyl or n-pentyl. Examples for these compounds are a) (9S)-9-ethyl-9-hydroxy-1-(3-methylbutyl)-1H,12H-pyrano[3",4":6',7']indolizino[1',2':6,5]pyrido[4,3,2-de]quinazoline-2(3H)-thione-10,13(9H, 15H)-dione;

b) (9S)-9-ethyl-9-hydroxy-1-phenethyl-1H,12H-pyrano[3",4":6',7']indolizino[1',2':6,5]pyrido[4,3,2-de]quinazoline-2(3H)-thione-10,13(9H, 15H)-dione; and c) (9S)-9-ethyl-9-hydroxy-1-pentyl-1H,12H-pyrano[3",4":6',7']indolizino[1',2':6,5]pyrido[4,3,2-de]quinazoline-2(3H)-thione-10,13(9H,15H)-dione.

Another embodiment of the present invention refers to compounds represented by formula [1B],

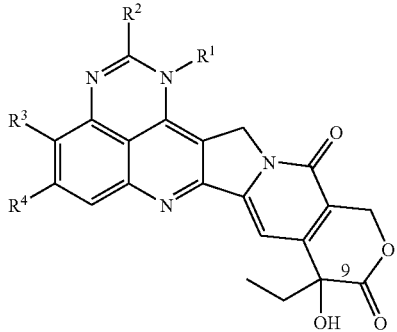

[1B]

wherein $R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino;

$R^2$ is hydrogen; amino; (C1–C5) alkyl; (C1–C5) alkoxy; (C1–C5) alkylthio; mono-(C1–C5) alkylamino; di-(C1–C5) alkylamino optionally substituted with one to three moieties independently selected from the group consisting of (C1–C5) alkoxy, hydroxy, halogen, amino, (C3–C7) cycloalkyl, heterocyclic ring or an aryl ring in which the aryl ring is optionally substituted with one to three moieties independently selected from the group consisting of hydroxy, (C1–C5) alkoxy, amino, mono-(C1–C5) alkylamino and di-(C1–C5) alkylamino;

$R^3$ and $R^4$ are independently hydrogen, halogen or (C1–C5) alkyl; or a pharmaceutically acceptable salt thereof. Preferred are compound of as defined above wherein $R^1$ is hydrogen or (C1–C8) alkyl which is optionally substituted with one to three moieties independently selected from the group consisting of (C1–C3) alkoxy, hydroxy, halogen, amino, mono-(C1–C3) alkylamino, di-(C1–C3) alkylamino, (C3–C7) cycloalkyl, a heterocyclic ring and an aryl ring in which the aryl ring is optionally substituted with one to three moieties independently selected from the group consisting of hydroxy, alkoxy and halogen; $R^2$ is hydrogen; amino or (C1–C5) alkyl optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring; (C1–C5) alkylthio; (C1–C5) alkoxy; mono-(C1–C5) alkylamino; and di-(C1–C5) alkylamino; $R^3$ is hydrogen or (C1–C3) alkyl; and $R^4$ is hydrogen. More preferred are compound of formula [1B] as described above wherein $R^1$ is methyl, ethyl, n-propyl, 1-methylethyl, n-butyl, 1,1-dimethylethyl, 2-methylpropyl, 2,2-dimethylpropyl, n-pentyl, 3-methylbutyl, 2-n-hexyl, 3,3-dimethylbutyl, n-heptyl, n-octyl, benzyl, phenethyl, 2-(dimethylamino)ethyl, 2-(4-morpholino)ethyl, 3-(dimethylamino)propyl, 2-(pyridin-2-yl)ethyl, 2-(pyridin-3-yl) ethyl, 2-(4-methoxyphenyl)ethyl, 2-(4-chlorophenyl) ethyl or 2-(4-fluorophenyl)ethyl, 3-phenylpropyl; $R^2$ is hydrogen, methyl, ethyl, propyl, hydroxymethyl, aminomethyl, (methylamino)methyl, (dimethylamino)methyl, chloromethyl, trifluoromethyl, phenyl, 2-pyridyl, methoxy, ethoxy, methylthio, ethylthio, methylamino, butylamino or dimethylamino; $R^3$ is hydrogen or methyl; and $R^4$ is hydrogen. Preferred compound may be selected from the group consisting of:

a) (9S)-1-butyl-9-ethyl-9-hydroxy-1H,12H-pyrano[3″,4″:6′,7′]indolizino[1′,2′:6,5]-pyrido[4,3,2-de]quinazoline-10,13(9H,15H)-dione;

b) (9S)-9-ethyl-9-hydroxy-1-[2-(4-morpholino)ethyl]-1H,12H-pyrano[3″,4″:6′,7′]indolizino[1′,2′:6,5]pyrido[4,3,2-de]quinazoline-10,13(9H,15H)dione hydrochloride;

c) (9S)-9-ethyl-9-hydroxy-1-propyl-1H,12H-pyrano[3″,4″:6′,7′]indolizino[1′,2′:6,5]pyrido[4,3,2-de]quinazoline-10,13(9H,15H)-dione;

e) (9S)-1-benzyl-9-ethyl-9-hydroxy-1H,12H-pyrano[3″,4″:6′,7′]indolizino[1′,2′:6,5]pyrido[4,3,2-de]quinazoline-10,13(9H,15H)-dione;

d) (9S)-9-ethyl-9-hydroxy-1-phenethyl-1H,12H-pyrano[3″,4″:6′,7′]indolizino[1′,2′:6,5]pyrido[4,3,2-de]quinazoline-10,13(9H,15H)-dione;

f) (9S)-2,9-diethyl-9-hydroxy-1-phenethyl-1H,12H-pyrano[3″,4″:6′,7′]indolizino[1′,2′:6,5]pyrido[4,3,2-de]quinazoline-10,13(9H,15H)-dione;

g) (9S)-9-ethyl-9-hydroxy-1-(3-phenylpropyl)-1H,12H-pyrano[3″,4″:6′,7′]indolizino[1′,2′:6,5]pyrido[4,3,2-de]quinazoline-10,13(9H,15H)-dione;

h) (9S)-9-ethyl-9-hydroxy-1-(3-methylbutyl)-1H,12H-pyrano[3″,4″:6′,7′]indolizino[1′,2′:6,5]pyrido[4,3,2-de]quinazoline-10,13(9H,15H)-dione;

i) (9S)-2,9-diethyl-9-hydroxy-1-(3-methylbutyl)-1H,12H-pyrano[3″,4″:6′,7′]indolizino[1′, 2′:6,5]pyrido[4,3,2-de]quinazoline-10,13(9H,15H)-dione;

j) (9S)-2,9-diethyl-9-hydroxy-1-(2-methylpropyl)-1H,12H-pyrano[3″,4″:6′,7′]indolizino[1′,2′:6,5]pyrido[4,3,2-de]quinazoline-10,13(9H,15H)-dione;

k) (9S)-9-ethyl-1-heptyl-9-hydroxy-1H,12H-pyrano[3″,4″:6′,7′]indolizino[1′,2′:6,5]pyrido[4,3,2-de]quinazoline-10,13(9H,15H)-dione;

l) (9S)-9-ethyl-9-hydroxy-1-methyl-1H,12H-pyrano[3″,4″:6′,7′]indolizino[1′,2′:6,5]pyrido[4,3,2-de]quinazoline-10,13(9H,15H)-dione;

m) (9S)-9-ethyl-9-hydroxy-1-(2-methylpropyl)-1H,12H-pyrano[3″,4″:6′,7′]indolizino[1′,2′:6,5]pyrido[4,3,2-de]quinazoline-10,13(9H,15H)-dione;

n) (9S)-9-ethyl-1-hexyl-9-hydroxy-1H,12H-pyrano[3″,4″:6′,7′]indolizino[1′,2′:6,5-]pyrido[4,3,2-de]quinazoline-10,13(9H,15H)-dione;

o) (9S)-9-ethyl-9-hydroxy-1-pentyl-1H,12H-pyrano[3″,4″:6′,7′]indolizino[1′,2′:6,5]pyrido[4,3,2-de]quinazoline-10,13(9H,15H)-dione;

p) (9S)-1,9-diethyl-9-hydroxy-1H,12H-pyrano[3″,4″:6′,7′]indolizino[1′,2′:6,5]pyrido[4,3,2-de]quinazoline-10,13(9H,15H)-dione;

q) (9S)-9-ethyl-9-hydroxy-1-[2-(4-methoxyphenyl)ethyl]-1H,12H-pyrano[3″,4″:6′,7′]indolizino[1′,2′:6,5]pyrido[4,3,2-de]quinazoline-10,13(9H,15H)-dione;

r) (9S)-1-[2-(4-chlorophenyl)ethyl]-9-ethyl-9-hydroxy-1H,12H-pyrano[3″,4″:6′,7′]indolizino[1′,2′:6,5]pyrido[4,3,2-de]quinazoline-10,13(9H,15H)-dione;

s) (9S)-9-ethyl-1-[2-(4-fluorophenyl)ethyl]-9-hydroxy-1H,12H-pyrano[3″,4″:6′,7′]indolizino[1′,2′:6,5]pyrido[4,3,2-de]quinazoline-10,13(9H,15H)-dione;

t) (9S)-9-ethyl-1-[2-(4-fluorophenyl)ethyl]-9-hydroxy-2-methyl-1H,12H-pyrano[3″,4″:6′,7′]indolizino[1′,2′:6,5]pyrido[4,3,2-de]quinazoline-10,13(9H,15H)-dione;

u) (9S)-9-ethyl-9-hydroxy-1-(1-methylethyl)-1H,12H-pyrano[3",4":6',7']indolizino[1',2':6,5]pyrido[4,3,2-de]quinazoline-10,13(9H,15H)-dione;

v) (9S)-1-(3,3-dimethylbutyl)-9-ethyl-9-hydroxy-1H,12H-pyrano[3",4":6',7']indolizino[1',2':6,5]pyrido[4,3,2-de]quinazoline-10,13(9H, 15H)-dione;

w) (9S)-9-ethyl-9-hydroxy-2-methoxy-1-(3-methylbutyl)-1H,12H-pyrano[3",4":6',7']indolizino[1',2':6,5]pyrido[4,3,2-de]quinazoline-10,13(9H, 15H)-dione;

x) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H, 15H)-dione;

y) (9RS)-9-ethyl-9-hydroxy-4-methyl-1-pentyl-1H,12H-pyrano[3",4":6',7']indolizino[1,2':6,5]pyrido[4,3,2-de]quinazoline-10,13(9H, 15H)-dione;

z). (9S)-9-ethyl-9-hydroxy-1-(2-hydroxyethyl)-1H,12H-pyrano[3",4":6',7']indolizino[1,2':6,5]pyrido[4,3,2-de]quinazoline-10,13(9H,15H)-dione;

aa) (9S)-9-ethyl-9-hydroxy-1-(2-hydroxyethyl)-2-methyl-1H,12H-pyrano[3",4":6',7']indolizino[1',2':6,5]pyrido[4,3,2-de]quinazoline-10,13(9H, 15H)-dione;

bb) (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H, 15H)-dione;

cc) (9S)-2,9-diethyl-9-hydroxy-1-pentyl-1H,12H-pyrano[3",4":6',7']indolizino[1', 2':6,5]pyrido[4,3,2-de]quinazoline-10,13(9H, 15H)-dione;

dd) (9S)-9-ethyl-9-hydroxy-1-pentyl-2-propyl-1H,12H-pyrano[3",4":6',7']indolizino[1',2':6,5]pyrido[4,3,2-de]quinazoline-10,13(9H, 15H)-dione;

ee) (9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H, 15H)-dione;

ff) (9S)-9-ethyl-9-hydroxy-2-hydroxymethyl-1-(2-methylpropyl)-1H,12H-pyrano[3",4":6',7']indolizino[1',2':6,5]pyrido[4,3,2-de]quinazoline-10,13(9H,15H)-dione;

gg) (9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione;

hh) (9S)-2-chloromethyl-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

ii) (9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H,1SH)-dione;

jj) (9S)-9-Ethyl-9-hydroxy-1-pentyl-2-trifluoromethyl-1H,12H-pyrano[3",4":6',7']indolizino[1',2':6,5]pyrido[4,3,2-de]quinazoline-10,13(9H,1SH)-dione;

kk) (9S)-9-ethyl-9-hydroxy-1-(3-methylbutyl)-2-methylthio-1H,12H-pyrano[3",4":6',7']indolizino[1',2':6,5]pyrido[4,3,2-de]quinazoline-10,13(9H,15H)-dione;

ll) (9S)-9-ethyl-2-ethylthio-9-hydroxy-1-(3-methylbutyl)-1H,12H-pyrano[3",4":6',7']indolizino[1',2':6,5]pyrido[4,3,2-de]quinazoline-10,13(9H,15H)-dione;

mm) (9S)-2-(dimethylamino)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione hydrochloride; and nn) (9S)-2-(butylamino)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione hydrochloride.

More preferably the compounds may be selected from the group consisting of:

a) (9S)-1-butyl-9-ethyl-9-hydroxy-1H,12H-pyrano[3",4":6',7']indolizino[1',2':6,5]pyrido[4,3,2-de]quinazoline-10,13(9H,15H)-dione;

b) (9S)-9-ethyl-9-hydroxy-1-phenethyl-1H,12H-pyrano[3",4":6',7']idolizino[1',2':6,5]pyrido[4,3,2-de]quinazoline-10,13(9H,15H)-dione;

c) (9S)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

d) (9S)-9-ethyl-9-hydroxy-(2-methylpropyl)-1H,12H-pyrano[3",4":6',7']indolizino[1',2':6,5]pyrido[4,3,2-de]quinazoline-10,13(9H,15H)-dione;

e) (9S)-9-ethyl-9-hydroxy-1-pentyl-1H,12H-pyrano[3",4": 6',7']indolizino[1',2':6,5]pyrido[4,3,2-de]quinazoline-10,13(9H,15H)-dione;

f) (9S)-9-ethyl-1-[2-(4-fluorophenyl)ethyl]-9-hydroxy-1H,12H-pyrano[3",4":6',7']indolizino[1,2':6,5]pyrido[4,3,2-de]quinazoline-10,13(9H,15H)-dione;

g) (9S)-1-(3,3-dimethylbutyl)-9-ethyl-9-hydroxy-1H,12H-pyrano[3",4":6',7']indolizino[1',2':6,5]pyrido[4,3,2-de]quinazoline-10,13(9H,15H)-dione;

h) (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)-dione;

i) (9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione; and j) (9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H, 15H)-dione.

Furthermore, among the compounds of the formulae [1A] and [1B], those in which the asymmetric carbon at position 9 has the S configuration are preferable from the aspect of medicinal activity.

The invention also refers to pharmaceutical compositions comprising a compound as described above as an active ingredient and a pharmaceutically acceptable carrier, especially those which are suitable for oral or parenteral administration.

Further the invention relates to the use a compound as defined above for the preparation of pharmaceutical compositions, especially for the treatment of cell proliferative disorders and/or cancer, e.g. colorectal cancer, lung cancer, breast cancer, stomach cancer, cervical cancer and bladder cancer. The invention also refers to a method for treating a cell proliferative disorder, e.g. cancer, comprising administering to a patient in need thereof a therapeutically effective amount of a compound as described above. The method is especially useful for the treatment of solid tumors and cancers like colorectal cancer, lung cancer, breast cancer, stomach cancer, cervical cancer and bladder cancer.

The invention also provide a process for producing a compound of formula [2],

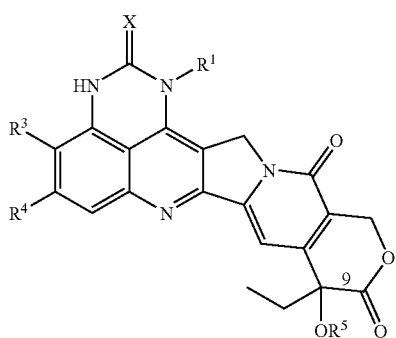

[2]

wherein $R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino; and $R^3$ and $R^4$ are independently hydrogen, halogen or (C1–C5) alkyl;

X is oxygen or sulfur;, and $R^5$ is (C1–C5) alkanoyl, which comprises reacting a compound of the formula [3] or its salt,

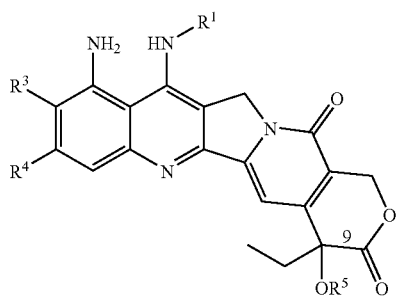

[3]

wherein $R^1$, $R^3$, $R^4$ and $R^5$ are the same as defined above, with a compound of the formula [4],

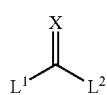

[4]

wherein X is the same as defined above, and $L^1$ and $L^2$ are independently leaving group such as halogen, (C1–C3) alkoxy optionally substituted by one to three halogen(s), phenyloxy optionally substituted by nitro group, succinimidyloxy or imidazole; in the presence of a base.

Another process of the invention refers to a process for producing a compound of formula [5],

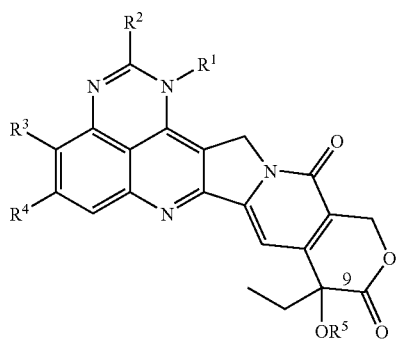

[5]

wherein $R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino;

$R^2$ is hydrogen; amino; (C1–C5) alkyl; (C1–C5) alkoxy; (C1–C5) alkylthio; mono-(C1–C5) alkylamino; di-(C1–C5) alkylamino optionally substituted with one to three moieties independently selected from the group consisting of (C1–C5) alkoxy, hydroxy, halogen, amino, (C3–C7) cycloalkyl, heterocyclic ring or an aryl ring in which the aryl ring is optionally substituted with one to three moieties independently selected from the group consisting of hydroxy, (C1–C5) alkoxy, amino, mono-(C1–C5) alkylamino or di-(C1–C5) alkylamino;

$R^3$ and $R^4$ are independently hydrogen, halogen or (C1–C5) alkyl;, and $R^5$ is (C1–C5) alkanoyl, which comprises reacting a compound of the formula [3] or its salt,

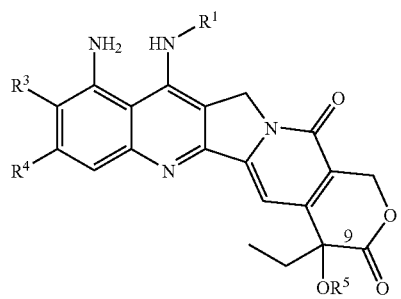

[3]

wherein $R^1$, $R^3$, $R^4$ and $R^5$ are the same as defined above, with a compound of the formula [6],

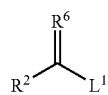

[6]

wherein $R^2$ is as defined above; $R^6$ is oxygen or sulfur; =$(OR^7)_2$ wherein $R^7$ is (C1–C3) alkyl; =$NR^8$ wherein $R^8$ is hydrogen, (C1–C3) alkyl, (C1–C3) alkanoyl or alkoxycarbonyl; =$N^+R^9R^{10}$ wherein $R^9$ and $R^{10}$ are independently (C1–C3) alkyl or halogen; and $L^1$ is a leaving group such as halogen, hydroxy, (C1–C3)alkoxy optionally substituted by one to three halogen(s), phenyloxy optionally substituted by nitro group, succinimidyloxy, or imidazole.

The invention also refers to a process for producing a compound of formula [1] as defined above or a pharmaceutically acceptable salt thereof,

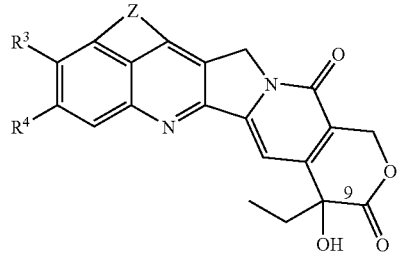

[1]

wherein Z is —NH—C(=X)—N(R¹)— or —N=C(R²)—N(R¹)—;

- R¹ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino;
- R² is hydrogen; amino; (C1–C5) alkyl; (C1–C5) alkoxy; (C1–C5) alkylthio; mono-(C1–C5) alkylamino; di-(C1–C5) alkylamino optionally substituted with one to three moieties independently selected from the group consisting of (C1–C5) alkoxy, hydroxy, halogen, amino, (C3–C7) cycloalkyl, heterocyclic ring and an aryl ring in which the aryl ring is optionally substituted with one to three moieties independently selected from the group consisting of hydroxy, (C1–C5) alkoxy, amino, mono-(C1–C5) alkylamino or di-(C1–C5) alkylamino;
- R³ and R⁴ are independently hydrogen, halogen or (C1–C5) alkyl;, which comprises subjecting a compound of the formula [1'],

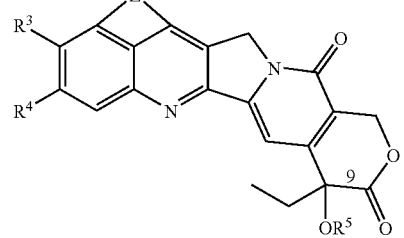

wherein Z, R¹, R² and R⁴ are as defined above; and R⁵ is (C1–C5) alkanoyl, to deacylation with a hydrazine or its derivative.

The invention comprises also those compounds prepared by a process as described above and to the compounds compound of formula [1] for use as medicament, especially in the treatment of cell proliferative disorders.

The following Scheme 1 describes the preparation of the hexacyclic compounds of the formulae formula [1], [1A] and [1B]. In the following Schemes 1, R¹, R², R³, R⁴ and X denote the same as those of the hexacyclic compounds as described above.

Scheme 1

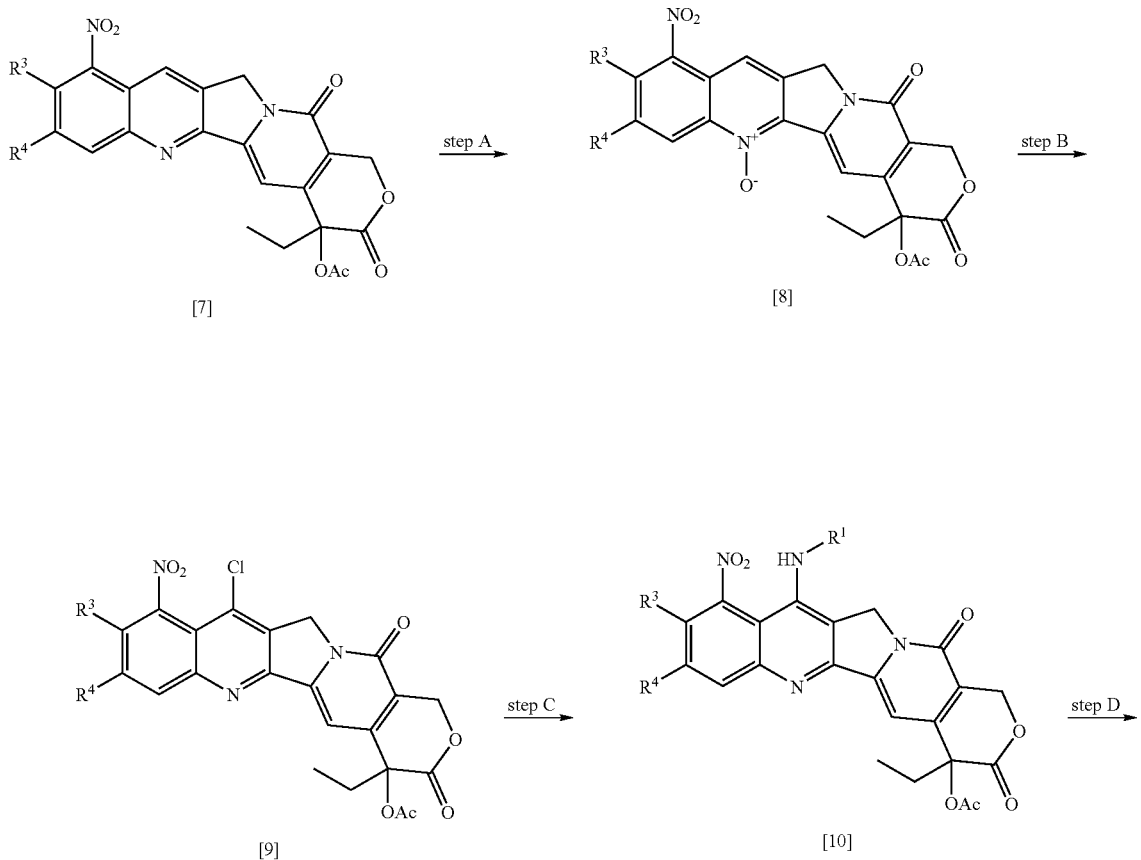

-continued
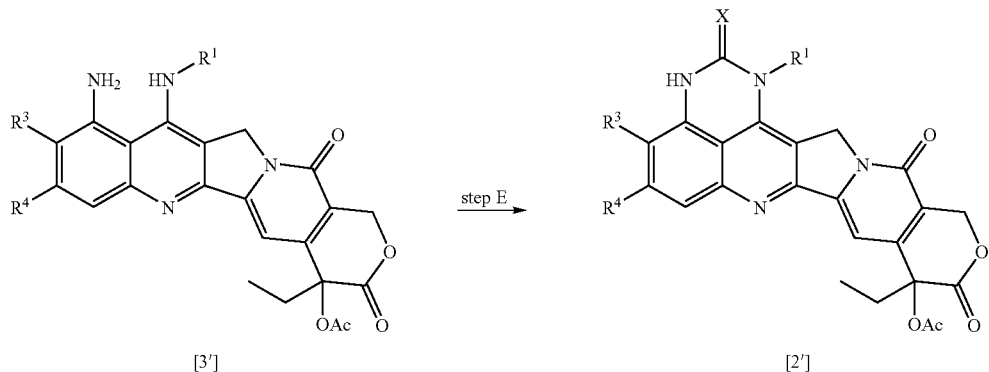
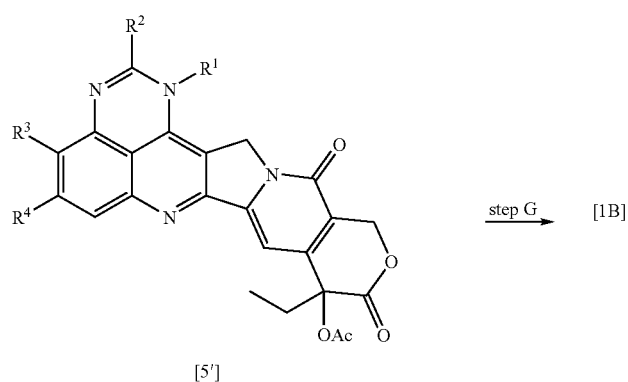
Starting compounds of the formula [7] are known compounds or can be prepared by methods known in the art. For example, (20S)-9-nitrocamptothecin 20-acetate is prepared according to the procedures reported by M. C. Wani et al. (J. Med. Chem. 1986, 29, 2358) or by F. H. Hausheer et al. (WO 9835940).
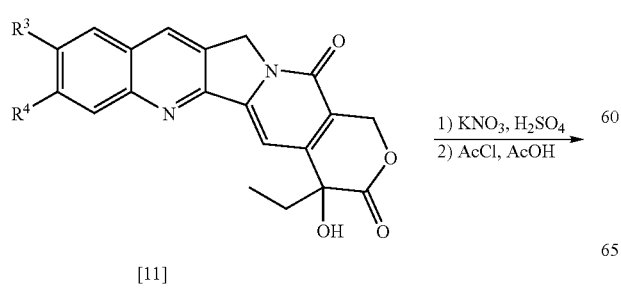
-continued
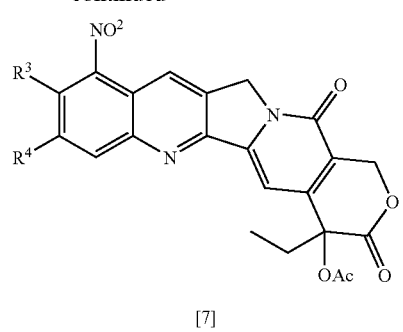
The reacting conditions of the above Steps A, B, C, D, E. F and G are briefly described hereafter.

Step A: Oxidation of a compound of the formula [7] to prepare a compound of the formula [8],

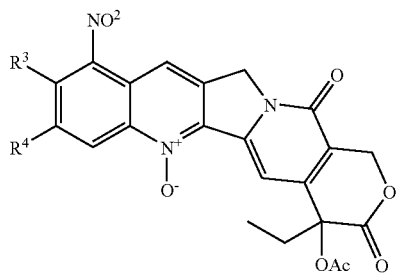

[8]

The oxidation of the above Step A is preferably carried out with a suitable oxidizing reagent in a suitable solvent. Suitable oxidizing reagents are hydrogen peroxide such as aqueous hydrogen peroxide and hydrogen peroxide-urea complex, percarboxylic acid such as peracetic acid, perbenzoic acid or m-chloroperbenzoic acid as like, and suitable solvent are acetic acid, tetrahydrofuran, chloroform, dichloromethane, as like. Typically, the oxidation is conducted at the temperature between 0 to 100° C. for 1 to 10 hours.

Step B: Chlorination of a compound of the formula [8] to prepare a compound of the formula [9],

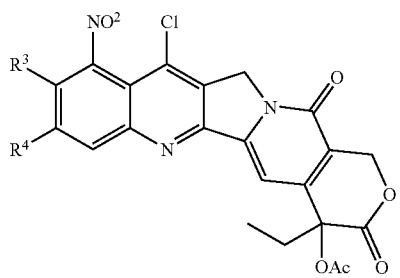

[9]

The chlorination of the above Step B is preferably carried out with a suitable chlorinating reagent in a suitable solvent. Suitable chlorinating reagents include phosphoryl chloride, thionyl chloride, oxalyl chloride, and Vilsmeier reagent, preferably with the use of N,N-dimethyl formamide as a catalyst or solvent. Suitable solvents are chloroform, dichloromethane as like as well as N,N-dimethylformamide as mentioned the above. Typically, the reaction is conducted at the temperature 0 to 80° C. for 1 to 15 hours.

Step C: Addition of an amine $R^1$—$NH_2$ to a compound of the formula [9] to prepare a compound of the formula [10],

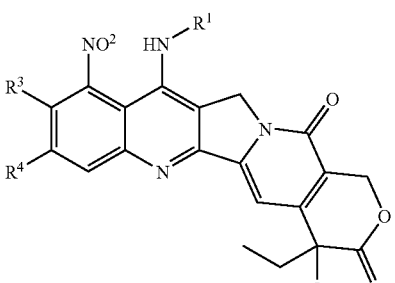

[10]

The addition of the above Step C is preferably carried out in a suitable organic solvent such as methanol, ethanol, tetrahydrofuran, 1,4-dioxane, chloroform, N,N-dimethyl formamide as like at the temperature from room temperature to 120° C. for a period of 15 minutes to 1 day.

Step D: Reduction of a compound of the formula [10] to prepare a compound of the formula [3'],

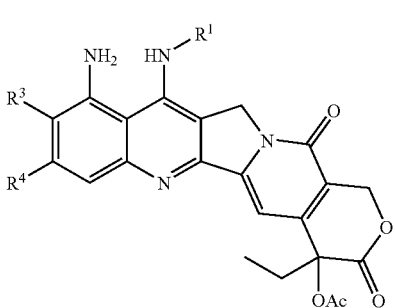

[3']

The reaction of the above Step D is preferably carried out with a reducing reagent in a suitable solvent in the presence of a suitable catalyst. Suitable reducing reagents are molecular hydrogen, or hydrogen source such as cyclohexadiene, formic acid, ammonium formate as like. Suitable solvents are e.g., methanol, ethanol, ethyl acetate, N,N-dimethyl formamide, 1,4-dioxane, and water with or without inorganic or organic acid such as 1 to 10 N aqueous hydrochloric acid, sulfonic acid, phosphonic acid, nitric acid, acetic acid, frifluoroacetic acid. Suitable catalysts are transition metals such as palladium, platinum, nickel, and typically are 5 to 10% palladium on charcoal and platinum oxide. Typically the reaction is conducted at the temperature 0 to 100° C., at the pressure 1 to 100 atmosphere for a time of 15 minutes to 1 day. The reaction of the Step D is also achieved with elemental metal or low-valent metal salt such as Zn, Fe, and $5 nCl_2$ in a suitable solvent such as aqueous hydrochloric aid and methanolic hydrochloric acid at the temperature 0 to 100° C. for a period of 15 minutes to 1 day.

Step E: Reaction of a compound of the formula [3'] with a compound of formula [4],

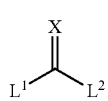

[4]

wherein $L^1$ and $L^2$ are (optionally different) leaving groups, e.g. halogen, (C1–C3)alkoxy optionally substituted by one to three halogen(s), phenyloxy optionally substituted by nitro group, succinimidyloxy, or imidazole, to prepare a compound of formula [2'],

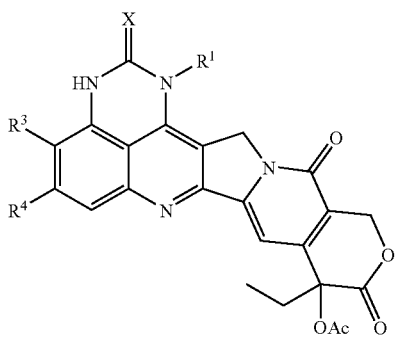

[2']

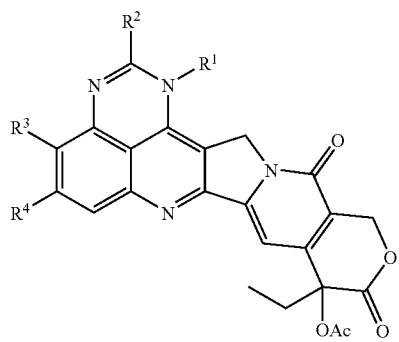

[5']

The reaction of the above Step E is preferably carried out with a suitable reagent of the formula [7] and a suitable base in a suitable solvent. Suitable bases are typically trialkylamine such as triethylamine and diisopropylethylamine, aromatic amine such as pyridine and lutidines, and inorganic base such as sodium carbonate and sodium bicarbonate. Suitable solvents are chloroform, dichloromethane, acetonitrile, 1,4-dioxane, N,N-dimethyl formamide as like. The reaction is conducted typically at between −20 to 100° C. for a period from 5 minutes to 1 several days. Typical reagents of the formula [10] are phosgene, diphosgene, triphosgene, thiophosgene, carbonyl diimidazole, thiocarbonyl diimidazole, phenyl chloroformate, ethyl chloroformate, diphenyl carbonate and the like.

Step F: Reaction of a compound of the formula [3'] with a compound of the formula [6],

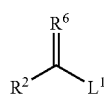

[6]

wherein $R^2$ is hydrogen; amino; (C1–C5) alkyl; (C1–C5) alkoxy; (C1–C5) alkylthio; mono-(C1–C5) alkylamino; di-(C1–C5) alkylamino optionally substituted with one to three moieties independently selected from the group consisting of (C1–C5) alkoxy, hydroxy, halogen, amino, (C3–C7) cycloalkyl, heterocyclic ring and an aryl ring in which the aryl ring is optionally substituted with one to three moieties independently selected from the group consisting of hydroxy, (C1–C5) alkoxy, amino, mono-(C1–C5) alkylamino or di-(C1–C5) alkylamino; $R^6$ is oxygen or sulfur; $(OR^7)_2$ in which $R^7$ is (C1–C5)alkyl; =$NR^8$ group in which $R^8$ is hydrogen, (C1–C5)alkyl, (C1–C5)alkanoyl or (C1–C5) alkoxycarbonyl; =$N^+R^9R^{10}$ in which $R^9$ and $R^{10}$ are independently (C1–C5)alkyl or halogen; and $L^1$ is a leaving group, such as halogen, hydroxy, (C1–C3)alkoxy optionally substituted by one to three halogen(s), phenyloxy optionally substituted by nitro group, succinimidyloxy, or imidazole, to prepare a compound of the formula [5'], The reaction of the above Step F is preferably carried out with a suitable reagent of the formula [6] and a suitable base or acid catalysts in a suitable solvent. Suitable bases are typically trialkylamine bases such as triethylamine and diisopropylethylamine, aromatic amine bases such as pyridine and lutidines, and inorganic bases such as sodium carbonate and sodium bicarbonate. Suitable acid catalysts are typically inorganic acids such as hydrochloric acid, sulfonic acid and nitric acid, organic acids such as acetic acid, trifluoroacetic acid, methanesulfonic acid and p-toluenesulfonic acid, and Lewis acid such as boron trifluoride, titanium tetrachloride and tin tetrachloride as like. Suitable solvents are chloroform, dichloromethane, acetonitrile, 1,4-dioxane, N,N-dimethyl formamide and the like. The reaction is conducted typically at between −20 to 100° C. for a period from 5 minutes to 1 several days.

Step G: Reaction (deacetylation) of a compound of the formula [2'] or [5'] with hydrazine to prepare a hexacyclic compound of the formula [1A] or [1B]

The reaction of the above Step G is preferably carried out with hydrazine in a suitable solvent and at suitable temperature. The suitable solvent are typically methanol, ethanol, 1,4-dixane, N,N-dimethylformamide, dimethylsulfoxide and water as like. The reaction is conducted typically at between −20 to 100° C. for a period from 5 minutes to 1 several days.

Furthermore, hexacyclic compounds of the formula [1B] can be prepared alternatively from a compound [2'] by processes illustrated in the following Scheme 2. In the following Schemes 2, $R^2$ is (C1–C5)alkylthio amino, mono-(C1–C5)alkylamino or di-(C1–C5)alkylamino; X is sulfur; $R^1$ is hydrogen; (C1–C10) alkyl, optionally substituted with one to three moieties independently selected from the group consisting of (C1–C5) alkoxy, hydroxy, halogen, amino, mono-(C1–C5) alkylamino, di-(C1–C5) alkylamino, (C3–C7) cycloalkyl, a heterocyclic ring and an aryl ring in which the aryl ring is optionally substituted with one to three moieties independently selected from the group consisting of hydroxy, alkoxy, halogen, amino, mono-(C1–C5) alkylamino and di-(C1–C5) alkylamino;

$R^3$ and $R^4$ are independently hydrogen, halogen or (C1–C5) alkyl; $R^{11}$ is (C1–C5)alkyl; and $R^{12}$ and $R^{13}$ are independently hydrogen or (C1–C5)alkyl.

Scheme 2

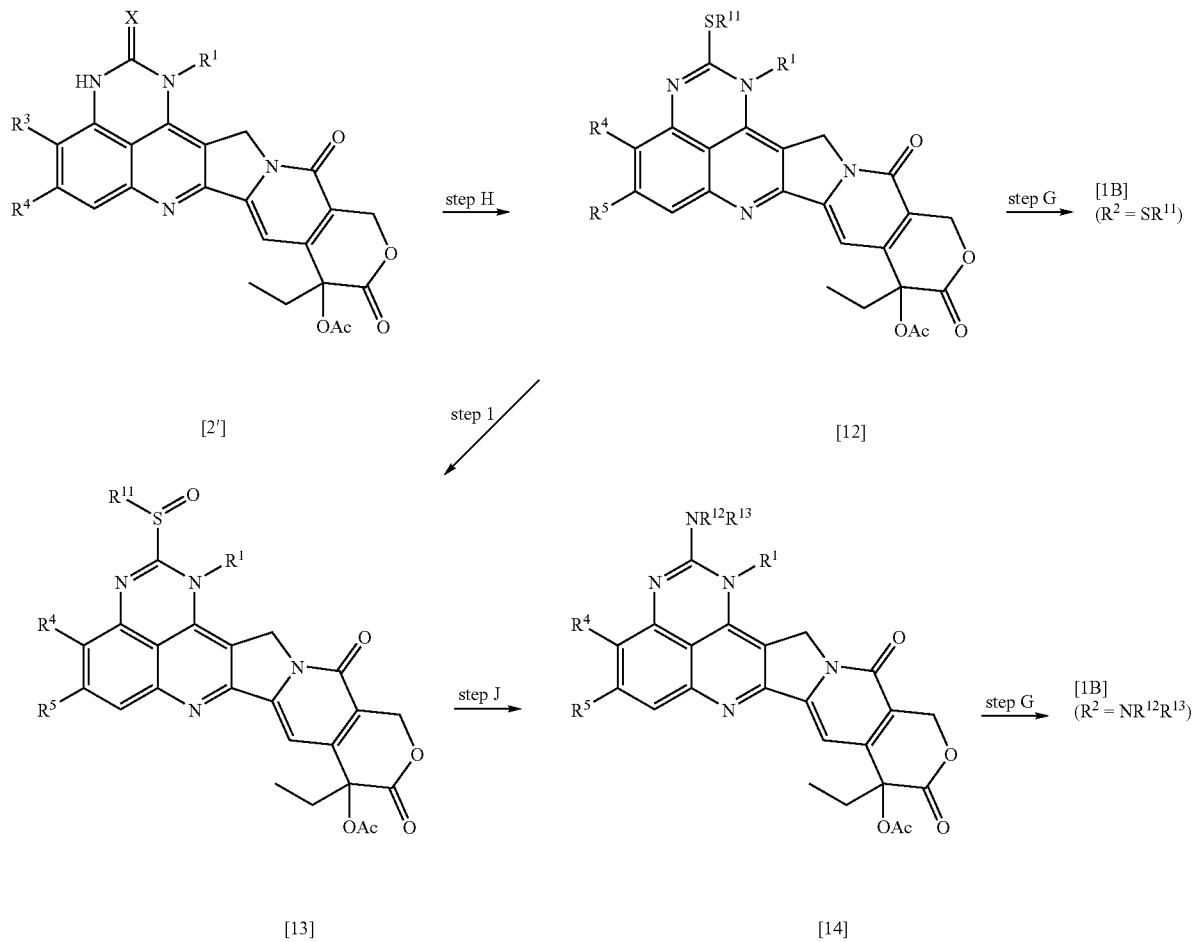

The reacting conditions of the above Steps H, I and J are also briefly described hereafter.

Step H: Alkylation of a compound of the formula [2'] with an alkylating reagent to prepare a compound of the formula [12], The alkylation of the above Step H is preferably carried out with a suitable alkylating reagent in a suitable solvent. Suitable alkylating reagents are alkyl halide, alkyl sulfonate and dialkyl sulfate such as alkyl iodide, alkyl bromide, alkyl p-toluenesulfonate, alkyl mathanesulfonate and dialkyl sulfate, as like. The suitable solvents are tetrahydrofuran, chloroform, dichloromethane and the like. Typically, the reaction is conducted at the temperature between 0 to 100° C. for 0.1 to 10 hours.

Step I: Oxidation of a compound of the formula [12] to prepare a compound of the formula [13],

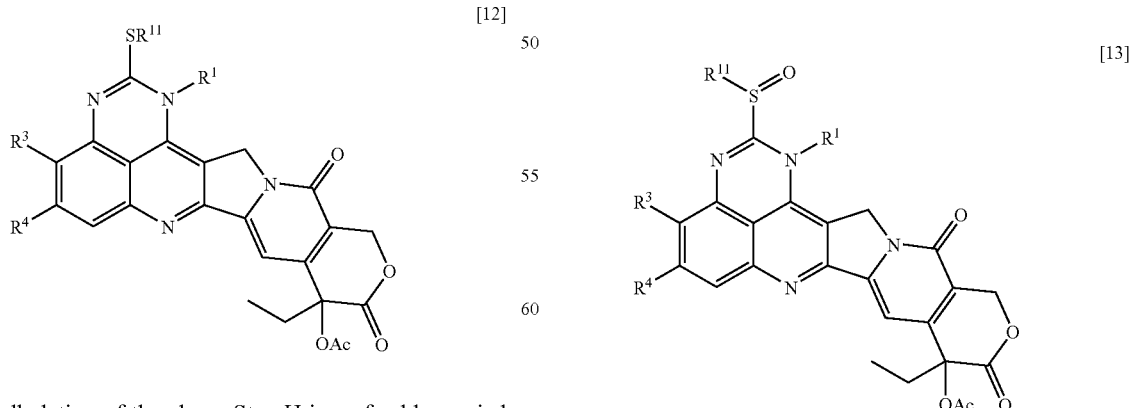

The oxidation of the above Step I is preferably carried out with a suitable oxidising reagent in a suitable solvent.

Suitable oxidising reagents are peroxide such as aqueous hydrogen peroxide and hydrogen peroxide-urea complex, percarboxylic acid such as peracetic acid, perbenzoic acid or m-chloroperbenzoic acid, and persulfate such as OXONE® (DuPont, U.S.A.), and suitable solvents are acetic acid, tetrahydrofuran, chloroform, dichloromethane, and the like. Typically, the reaction is conducted at the temperature between 0 to 100° C. for 1 to 10 hours.

Step J: Addition of an amine of the formula $HNR^{12}R^{13}$ to a compound of the formula [13] to prepare a compound of the formula [14],

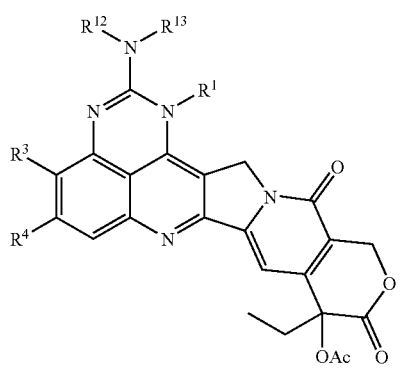

[14]

The reaction of the above Step J is preferably carried out with a suitable amine $HNR^{12}R^{13}$ in a suitable solvent. Suitable amines $HNR^{12}R^{13}$ are ammonia, primary amines and secondary amines, preferably mono- and di-(C1–C5) alkylamines such as mono- and dimethylamine, mono- and diethylamine, mono- and dipropylamine and mono- and dibutylamine and the like. The reaction is carried out in a suitable solvent such as acetic acid, tetrahydrofuran, chloroform, dichloromethane as like. Typically, the reaction is conducted at the temperature between 0 to 100° C. for 1 to 10 hours.

The hexacyclic compounds of the present invention can optionally be converted into a form of physiologically acceptable salt, e.g., a salt of an alkali metal or alkali earth metal, by using a hydroxide of these metals; or when such a compound is a basic compound such as that possessing an amino group or the like, may be converted into an inorganic or organic salt using an inorganic acid such as hydrochloric acid, sulfuric acid, phosphoric acid, or the like, or an organic acid such as formic acid, acetic acid, methanesulfonic acid or the like.

The manufacture of the pharmaceutically acceptable acid addition salts of the hexacyclic compounds of the formula [1] can be carried out by treating a free base of the hexacyclic compound of the formula [1] with an acid in a per se conventional procedure for the salt formation. Examples of therapeutically acceptable acids useful in the above process are inorganic acids (e.g. hydrochloric acid, hydrobromic acid, phosphoric acid, nitric acid, sulfuric acid) and organic acids (e.g. oxalic acid, acetic acid, formic acid, trifluoroacetic acid, maleic acid, succinic acid, fumaric acid, tartaric acid, citric acid, salicylic acid, sorbic acid, lactic acid, methanesulfonic acid). Moreover, the hexacyclic compounds of the formula [1] can be converted into the hydrates or solvates and their salts by various methods known to those skilled in the art.

The hexacyclic compounds of the present invention are useful for the treatment of cancer. Accordingly, the present invention comprises the use of the above compounds for the manufacture of pharmaceutical compositions for the treatment of cancer and the corresponding pharmaceutical compositions which comprise a hexacyclic compound as defined above and a pharmaceutically acceptable carrier.

The hexacyclic compounds of the present invention are effective at inhibiting or preventing the growth of tumors in premalignant and malignant cells and are useful for the treatment of carcinomas forming solid tumors, especially of colorectal cancer, lung cancer, breast cancer, stomach cancer, cervical cancer and bladder cancer. The hexacyclic compounds of the present invention can be used to treat such tumors, to retard the development of such tumors, and to prevent the increase in number of tumors.

The anti-cancer therapeutic activity of the hexacyclic compounds of this invention may be demonstrated by various standard in vitro assays. Such assays described below and in the examples are known to indicate anticancer activity and are assays for cancer therapeutics. The hexacyclic compounds of the present invention have the structure depicted in formula [1], and anticancer activity as determined by any standard assay, especially assays for apoptosis. The hexacyclic compounds of this invention are particularly effective to induce apoptosis in carcinoma cells, causing the death of the cell.

Thus the hexacyclic compounds of this invention are the desired activities if the compounds cause carcinoma cells to die when the cells are exposed to the hexacyclic compounds of this invention. Carcinoma cells for assays (for example breast, lung, colorectal, etc.) are readily obtained from cells depositories such as the American Type Culture Collection (ATCC) or may be isolated by skilled persons from cancer patients. The type of cancer against which the hexacyclic compounds of this invention are most active is determined by the type of cells used in the assays.

Carcinoma cells, grown in culture, may be incubated with a specific compound and changes in cells viability may be determined for example, by dyes which selectively stain dead cells or by optical density (O.D.) measurement. If more than 10% of cells have died, the compound is active in inducing apoptosis. The compounds may not directly kill the cells (cellular toxicity) but may modulate certain intra- or extracellular events which result in apoptosis. The anticancer activity of the compounds of this invention may also be determined by assays that access the effects of compounds on cells growth and differentiation. Cell growth inhibition may be determined by adding the compound in question to carcinoma cells in culture with dyes or radioactive precursors, and determining by microscopic cell counting, scintillation counting, or O.D. measurement whether the number of cells has increased over the incubation period. If the number of cells has not increased, growth has been inhibited and the compound is regarded as having therapeutic activity. Similarly, the proportion of cells which have become differentiated after addition of a test compound may be determined by known methods (i.e. measuring oxidative burst in HL-60 cells, an indicator of differentiation, by NBT(nitroblue tetrazolium). If 10% or more cells have differentiated, then the compound is regarded as having therapeutic activity.

Antiproliferative activity assay was carried out as follows. A single suspension of tumor cells was inoculated to the serially diluted 96-well microtestplate. Then the testplate was incubated in the 5% $CO_2$ ambience at 37° C. for 4 days $(2–3\times10^3$ cells/well). The degree of cell growth in a monolayer was measured by using WST-8 (Dojindo, Japan). $IC_{50}$ values of drugs against tumor cells were calculated as the concentration of drug yielding 50% OD of the control growth. The IC$_{50}$ value measures the drug concentration for 50% of the growth of tumor cells in vitro as compared to the control. The results are shown in the following Table 1.

The anti-tumor activities of hexacyclic compounds of the formula [1A] and [1B] against in vitro growth of human tumor cell lines, HCT116 and DLD-1 of colorectal cancer (CRC) and QG56 and NCI-H460 of non small cell lung cancer (NSCLC) are summarized in Table 1. These cell lines are commercially available via the American Type Culture Collection (ATTC).

In Table 1,

Compound A denotes (9S)-9-ethyl-9-hydroxy-1-phenethyl-1H,12H-pyrano[3",4":6',7']indolizino[1',2':6,5]pyrido[4,3,2-de]quinazoline-2,10,13(3H,9H,15H)-trione.

Compound B denotes (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione.

Compound D denotes (9S)-9-ethyl-9-hydroxy-1-(3-methylbutyl)-2(3H)-thioxo-1H,12H-pyrano[3",4":6',7']indolizino[1',2':6,5]pyrido[4,3,2-de]quinazoline-10,13(9H,15H)-dione.

Compound E denotes (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)-dione.

Compound F denotes (9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione. SN-38 denotes 7-ethyl-10-hydroxycamptothecin.

TABLE 1

Anti-proliferative activity assay (IC$_{50}$ in nM)

| Compound | HCT116 (CRC) | DLD-1 (CRC) | QG56 (NSCLC) | NCI-H460 (NSCLC) |
|---|---|---|---|---|
| Compound A | 1.9 | 11 | 7.1 | 6.5 |
| Compound B | 6.1 | 23 | 7.7 | 7.0 |
| Compound D | 5.1 | 15 | 17 | 10 |
| Compound E | 4.5 | 15 | 15 | 7.9 |
| Compound F | 3.1 | 12 | 7.4 | 4.8 |
| SN-38 (Reference) | 6.9 | 53 | 27 | 21 |

For clinical use, the hexacyclic compounds of the formula [1], their prodrugs, or salt forms thereof and the like can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, rectal or topical administration.

In more detail, as mentioned earlier, pharmaceutical compositions containing a compound of the formula [1] or its prodrug are also an aspect of the present invention, as is a process for the manufacture of such medicaments, whose process comprises bringing one or more compounds of the formula [1] and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragées or hard gelatine capsules, the hexacyclic compounds of the present invention may be admixed with pharmaceutically inert, inorganic or organic excipients (pharmaceutically acceptable carriers). Examples of suitable excipients for tablets, dragées or hard gelatine capsules include lactose, maize starch or derivatives thereof, talc or stearic acid or salts thereof. Suitable excipients for use with soft gelatine capsules include, for example, vegetable oils, waxes, fats, semi-solid or liquid polyols etc.; according to the nature of the active ingredients it may however be the case that no excipient is needed at all for soft gelatine capsules. For the preparation of solutions and syrups, excipients which may be used include for example water, polyols, saccharose, invert sugar and glucose. For injectable solutions, excipients which may be used include for example water, alcohols, polyols, glycerine, and vegetable oils. For suppositories, and local or percutaneous application, excipients which may be used include for example natural or hardened oils, waxes, fats and semi-solid or liquid polyols.

The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents.

In summary, a pharmaceutical formulation for oral administration may be granule, tablet, sugar coated tablet, capsule, pill, suspension or emulsion, which for parenteral injection, for example, intravenously, intramuscularly or subcutaneously, may be used in the form of a sterile aqueous solution which may contain other substances, for example, salts or glucose to make the solution isotonic. The anti-tumor agent can also be administered in the form of a suppository or pessary, or they may be applied topically in the form of a lotion, solution, cream, ointment or dusting powder.

The daily dosage level of the hexacyclic compounds of the present invention is from 5 to 2,000 mg/m$^2$ when administered by either the oral or parenteral route. Thus tablets or capsules can contain from 5 mg to 1,000 mg of active compound for single administration or two or more at a time as appropriate. In any event the actual dosage can be weight and response of the particular patient.

The following examples illustrate the preferred methods for the preparation of the hexacyclic compounds of the present invention, which are not intended to limit the scope of the invention thereto.

EXAMPLES

Reference Example 1

Preparation of (20RS)-10-methyl-9-nitrocamptothecin 20-acetate (20RS)-10-Methylcamptothecin (18.1 mg, 0.05 mmol) was dissolved in sulfuric acid (0.2 ml) and potassium nitrate (6.1 mg, 0.06 mmol) was added to the solution. After stirring for 2 hr. at room temperature, the mixture was poured into water and extracted with dichloromethane. The organic layer was concentrated under reduced pressure to give (20RS)-10-methyl-9-nitrocamptothecin (18.1 mg, 89%) as an off-white solid;

¹H NMR (270 MHz) δ (DMSO-d₆) 0.88 (t, J=7.3 Hz, 3H), 1.75–2.00 (m, 2H), 2.57 (s, 3H), 5.28 (s, 1H), 5.44 (s, 2H), 6.56 (s, 1H), 7.37 (s, 1H), 7.94 (d, J=8.9 Hz, 1H), 8.35 (d, J=8.9 Hz, 1H), 8.53 (s, 1H): MS (ES) m/z 408 (M⁺+1).

(20RS)-10-Methyl-9-nitrocamptothecin (15.9 mg, 0.039 mmol) was suspended in acetic acid (2 ml) and acetyl chloride (0.4 ml) was added to the suspension. After stirring at 70° C. for 1.5 hr., methanol was added to the mixture in an ice-bath. The residue obtained by concentration of the mixture was purified by silica gel column chromatography (dichloromethane/acetone=30/1-10/1) to give the product (11.4 mg, 65%) as a colorless solid.

¹H NMR (270 MHz) δ (CDCl₃) 0.99 (t, J=7.6 Hz, 3H), 2.02–2.39 (m, 5H), 2.62 (s, 3H), 5.31 (s, 2H), 5.41 (d, J=17.5 Hz, 1H), 5.68 (d, J=17.5 Hz, 1H), 7.21 (s, 1H), 7.74 (d, J=8.9 Hz, 1H), 8.28 (d, J=8.9 Hz, 1H), 8.33 (s, 1H); MS (ES) m/z 450 (M⁺+1).

Reference Example 2.1

Preparation of (20S)-9-nitrocamptothecin-N-oxide 20-acetate

To a solution of 9-nitrocamptothecin 20-acetate (8.62 g, 19.8 mmol) in trifluoroacetic acid (65 ml) was added urea-hydrogen peroxide (3.11 g, 33.1 mmol) at room temperature. After stirring for 4 hr. at room temperature, the mixture was concentrated under reduce pressure to approximately a half volume and poured into an ice-water mixture. The generated precipitate was collected by filtration, washed with distilled water, and dried in vacuo to obtain the titled compound (8.35 g, 93% yield).

¹H NMR (270 MHz) δ (CDCl₃) 0.98 (t, J=7.6 Hz, 3H), 2.08–2.33 (m, 2H), 2.23 (s, 3H), 5.38 (s, 2H), 5.40 (d. J=17.7 Hz, 1H), 5.67 (d, J=17.7 Hz, 1H), 7.96 (s, 1H), 7.96 (dd, J=7.6 and 7.8 Hz, 1H), 8.67 (s, 1H), 9.16 (d, J=7.6 Hz, 1H); MS m/z (ES) 452 (M⁺+1).

Reference Example 2.2

Preparation of (20RS)-10-methyl-9-nitrocamptothecin-N-oxide 20-acetate

This compound was prepared from (20RS)-10-methyl-9-nitrocamptothecin 20-acetate of Reference Example 1 according to a manner analogous to those of Reference Example 2.1.

¹H NMR (270 MHz) δ (CDCl₃) 0.97 (t, J=7.4 Hz, 3H), 2.03–2.38 (m, 5H), 2.61 (s, 3H), 5.31 (s, 2H), 5.38 (d, J=17.4 Hz, 1H), 5.64 (d, J=17.4 Hz, 1H), 7.74 (s, 1H), 7.77 (d, J=9.1 Hz, 1H), 7.93 (s, 1H), 8.84 (d, J=9.1 Hz, 1H); MS (ES) m/z 466 (M⁺+1).

Reference Example 3.1

Preparation of (20S)-7-chloro-9-nitrocamptothecin 20-acetate

To a solution of (20S)-9-nitrocamptothecin-N-oxide 20-acetate (10.88 g, 24.1 mmol) of Reference Example 2.1 in N,N-dimethylformamide (196 ml) was added oxalyl chloride (4.2 ml, 48.2 mmol) at 0° C., and the mixture was stirred at 15° C. for 3 hr. The mixture was poured into ice-water (500 ml), and extracted with ethyl acetate (500 ml×1, 250 ml×2). The organic layer was dried over anhydrous sodium sulfate, and concentrated under reduced pressure. The residue was purified by silica gel column chromatography (ethyl acetate/hexane=1/1) to give the titled compound (5.54 g, 49%) as a yellow solid.

¹H NMR (270 MHz) δ (CDCl₃) 0.99 (t, J=7.6 Hz, 3H), 2.07–2.33 (m, 2H), 2.23 (s, 3H), 5.33 (s, 2H), 5.41 (d, J=17.8 Hz, 1H), 5.69 (d, J=17.8 Hz, 1H), 7.20 (s, 1H), 7.87–7.95 (m, 2H), 8.44 (dd, J=2.3 and 7.6 Hz, 1H); MS m/z (ES) 470 (M⁺+1).

Reference Example 3.2

Preparation of (20RS)-7-chloro-10-methyl-9-nitrocamptothecin 20-acetate

This compound was prepared from (20RS)-10-methyl-9-nitrocamptothecin-N-oxide 20-acetate of Reference Example 2.2 according to a manner analogous to those of Reference Example 3.1.

¹H NMR (270 MHz) δ (CDCl₃) 0.98 (t, J=7.4 Hz, 3H), 2.02–2.36 (m, 5H), 2.55 (s, 3H), 5.30 (s, 2H), 5.40 (d, J=17.5 Hz, 1H), 5.68 (d, J=17.5 Hz, 1H), 7.17 (s, 1H), 7.78 (d, J=8.6 Hz, 1H), 8.29 (d, J=8.6 Hz, 1H); MS (ES) m/z 484 (M⁺+1).

Reference Example 4.1

Preparation of (20S)-9-nitro-7-(pentylamino)camptothecin 20-acetate

To a suspension of (20S)-7-chloro-9-nitrocamptothecin 20-acetate (2.58 g, 5.49 mmol) of Reference Example 3.1 in 1,4-dioxane (29 ml) was added n-amylamine (2.55 ml, 21.96 mmol) and the mixture was stirred at 80° C. for 2 hr, and then concentrated under reduced pressure. The resulting residue was purified by silica gel column chromatography (dichloromethane/acetone=30/1-20/1) to give the titled compound (1.80 g, 63%) as a brown oil.

¹H NMR (270 MHz) δ (CDCl₃) 0.86–1.01 (m, 6H), 1.22–1.59 (m, 4H), 1.60–1.78 (m, 2H), 2.03–2.37 (m, 5H), 3.57–3.68 (m, 2H), 5.02 (br, 1H), 5.40 (d, J=17.2 Hz, 1H), 5.47 (s, 2H), 5.67 (d, J=17.2 Hz, 1H), 7.13 (s, 1H), 7.66 (dd, J=2.0, 7.9 Hz, 1H), 7.71 (t, J=7.9 Hz, 1H), 8.23 (dd, J=2.0, 7.9 Hz, 1H); MS (ES) m/z 521 (M⁺+1).

Reference Example 4.2

Preparation of (20S)-9-nitro-7-[2-(morpholinyl)ethylamino]camptothecin 20-acetate This compound was prepared from (20S)-7-chloro-9-nitrocamptothecin 20-acetate of Reference Example 3.1 and 4-(2-aminoethyl)morpholine according to a manner analogous to those of Reference Example 4.1.

¹H NMR (400 MHz) δ (CDCl₃) 0.99 (t, J=7.6 Hz, 3H), 2.12–2.18 (m, 2H), 2.22 (s, 3H), 2.25–2.30 (m, 1H), 2.56 (m, 4H), 2.71 (t, J=5.6 Hz, 2H), 3.74–3.78 (m, 2H), 3.84 (t, J=4.6 Hz, 4H), 5.40 (d, J=17.4 Hz, 1H), 5.49 (d, J=18.4 Hz, 1H), 5.51 (d, J=18.4 Hz, 1H), 5.66 (d, J=17.4 Hz, 1H), 7.13 (s, 1H), 7.67–7.73 (m, 2H), 8.20 (dd, J=2.4 and 8.0 Hz, 1H); MS (ES) m/z 564(M⁺+1).

Reference Example 4.3

Preparation of (20S)-7-[3-(dimethylamino)propylamino]-9-nitrocamptothecin 20-acetate This compound was prepared from (20S)-7-chloro-9-nitrocamptothecin 20-acetate of Reference Example 3.1 and N,N-dimethyl 1,3-diaminopropane according to a manner analogous to those of Reference Example 4.1.

¹H NMR (270 MHz) δ (CDCl₃) 0.97 (t, J=7.5 Hz, 3H), 1.82–1.88 (m, 2H). 2.07–2.32 (m, 2H), 2.18 (s, 3H), 2.22 (s,

6H), 2.47 (t, J=5.7 Hz, 2H), 3.79–3.84 (m, 2H), 5.40 (d, J=17.2 Hz, 1H), 5.50 (s, 2H), 5.60 (d, J=17.2 Hz, 1H), 7.09 (brt, 1H), 7.13 (s, 1H), 7.67 (dd, J=7.6 and 8.6 Hz, 1H), 7.83 (dd, J=dd, J=1.3 and 7.6 Hz, 1H), 8.20 (dd, J=1.3 and 8.6 Hz, 1H); MS (ES) m/z 536 (M$^+$+1).

Reference Example 4.4

Preparation of (20S)-9-nitro-7-(propylamino)camptothecin 20-acetate

This compound was prepared from (20S)-7-chloro-9-nitrocamptothecin 20-acetate of Reference Example 3.1 and propylamine according to a manner analogous to those of Reference Example 4.1.

$^1$H NMR (270 MHz) δ (CDCl$_3$) 0.97 (t, J=7.6 Hz, 3H), 1.07 (t, J=7.2 Hz, 3H), 1.67–1.80 (m, 2H), 2.12–2.30 (m, 2H), 2.22 (s, 3H), 3.58–3.66 (m, 2H), 5.04 (brs, 1H), 5.40 (d, J=17.2 Hz, 1H), 5.46 (s, 2H), 5.67 (d, J=17.2 Hz, 1H), 7.14 (s, 1H), 7.64–7.74 (m, 2H), 8.23 (dd, J=1.3 and 7.9 Hz, 1H); MS (ES) m/z 493 (M$^+$+1)

Reference Example 4.5

Preparation of (20S)-7-benzylamino-9-nitrocamptothecin 20-acetate

This compound was prepared from (20S)-7-chloro-9-nitrocamptothecin 20-acetate of Reference Example 3.1 and benzylamine according to a manner analogous to those of Reference Example 4.1.

MS (ES) m/z 541 (M$^+$+1).

Reference Example 4.6

Preparation of (20S)-9-nitro-7-(phenethylamino)camptothecin 20-acetate

This compound was prepared from (20S)-7-chloro-9-nitrocamptothecin 20-acetate of Reference Example 3.1 and phenethylamine according to a manner analogous to those of Reference Example 4.1.

$^1$H NMR (400 MHz) δ (CDCl$_3$) 0.97 (t, J=7.4 Hz, 3H), 2.10–2.30 (m, 2H), 2.22 (s, 3H), 3.00 (t, J=6.6 Hz, 2H), 3.94 (m, 2H), 4.93 (m, 1H), 5.40 (d, J=17.0 Hz, 1H), 5.46 (s, 2H), 5.67 (d, J=17.0 Hz, 1H), 7.12 (s, 1H), 7.25–7.33 (δ, 3H), 7.36–7.39 (m, 2H), 7.66–7.71 (m, 2H), 8.21 (dd, J=3.0 and 7.4 Hz, 1H); MS (ES) m/z 555 (M$^+$+1).

Reference Example 4.7

Preparation of (20S)-9-nitro-7-(3-phenylpropylamino)camptothecin 20-acetate

This compound was prepared from (20S)-7-chloro-9-nitrocamptothecin 20-acetate of Reference Example 3.1 and 3-phenylpropylamine according to a manner analogous to those of Reference Example 4.1.

$^1$H NMR (270 MHz) δ (CDCl$_3$) 0.97 (t, J=7.4 Hz, 3H), 2.02 (m, 2H), 2.10–2.29 (m, 2H), 2.21 (s, 3H), 2.78 (t, J=7.4 Hz, 2H), 3.65 (m, 2H), 5.05 (m, 1H), 5.39 (s, 2H), 5.39 (d, J=17.3 Hz, 1H), 5.67 (d, J=17.3 Hz, 1H), 7.13 (s, 1H), 7.20–7.34 (δ, 5H), 7.65–7.75 (m, 2H), 8.24 (dd, J=2.3 and 7.9 Hz, 1H); MS (ES) m/z 569 (M$^+$+1).

Reference Example 4.8

Preparation of (20S)-9-nitro-7-[2-(pyridin-2-yl)ethylamino]camptothecin 20-acetate This compound was prepared from (20S)-7-chloro-9-nitrocamptothecin 20-acetate of Reference Example 3.1 and 2-(2-aminoethyl)pyridine according to a manner analogous to those of Reference Example 4.1.

$^1$H NMR (270 MHz) δ (CDCl$_3$) 0.97 (t, J=7.4 Hz, 3H), 2.10–2.32 (m, 2H), 2.22 (s, 3H), 3.16 (t, J=5.9 Hz, 2H), 4.09 (m, 2H), 5.40 (d, J=17.2 Hz, 1H), 5.52 (s, 2H), 5.68 (d, J=17.2 Hz, 1H), 6.88 (m, 1H), 7.13 (s, 1H), 7.19 (δ, 2H), 7.63–7.78 (m, 3H), 8.20 (dd, J=1.3 and 8.3 Hz, 1H), 8.61 (dd, J=1.8 and 5.8 Hz, 1H); MS (ES) m/z 556 (M$^+$+1).

Reference Example 4.9

Preparation of (20S)-9-nitro-7-[2-(pyridin-3-yl)ethylamino]camptothecin 20-acetate This compound was prepared from (20S)-7-chloro-9-nitrocamptothecin 20-acetate of Reference Example 3.1 and 3-(2-aminoethyl)pyridine according to a manner analogous to those of Reference Example 4.1.

$^1$H NMR (270 MHz) δ (CDCl$_3$) 0.97 (t, J=7.4 Hz, 3H), 2.09–2.32 (m, 2H), 2.22 (s, 3H), 3.02 (t, J=6.8 Hz, 2H), 3.94 (m, 2H), 4.96 (m, 1H), 5.39 (d, J=17.3 Hz, 1H), 5.46 (s, 2H), 5.67 (d, J=17.3 Hz, 1H), 7.13 (s, 1H), 7.32 (dd, J=4.8 and 7.4 Hz, 1H), 7.60–7.74 (m, 3H), 8.24 (dd, J=2.0 and 7.6 Hz, 1H), 8.50–8.58 (m, 2H); MS (ES) m/z 556 (M$^+$+1).

Reference Example 4.10

Preparation of (20S)-7-(3-methylbutylamino)-9-nitrocamptothecin 20-acetate

This compound was prepared from (20S)-7-chloro-9-nitrocamptothecin 20-acetate of Reference Example 3.1 and isoamylamine according to a manner analogous to those of Reference Example 4.1.

$^1$H NMR (270 MHz) δ (CDCl$_3$) 0.97 (t, J=7.6 Hz, 3H), 0.99 (d, J=6.6 Hz, 6H), 1.55 (m, 2H), 1.74 (m, 1H), 2.10–2.30 (m, 2H), 2.22 (s, 3H), 3.66 (dt, J=5.0 and 7.1 Hz, 2H), 4.98 (m, 1H), 5.40 (d, J=17.2 Hz, 1H), 5.49 (s, 2H), 5.68 (d, J=17.2 Hz, 1H), 7.14 (s, 1H), 7.65–7.75 (m, 2H), 8.24 (d, J=6.9 Hz, 1H); MS (ES) m/z 521 (M$^+$+1).

Reference Example 4.11

Preparation of (20S)-7-heptylamino-9-nitrocamptothecin 20-acetate

This compound was prepared from (20S)-7-chloro-9-nitrocamptothecin 20-acetate of Reference Example 3.1 and heptylamine according to a manner analogous to those of Reference Example 4.1.

$^1$H NMR (270 MHz) δ (CDCl$_3$) 0.85–1.00 (m, 6H), 1.22–1.52 (m, 8H), 1.59–1.69 (m, 2H), 2.14–2.28 (m, 5H), 3.64 (q, J=6.9 Hz, 2H), 5.00–5.03 (m, 1H), 5.40 (d, J=17.2 Hz, 1H), 5.47 (s, 2H), 5.67 (d, J=17.2 Hz, 1H), 7.13 (s, 1H), 7.66 (dd, J=2.0, 7.9 Hz, 1H), 7.71 (t, J=7.9 Hz, 1H), 8.23 (dd, J=2.0, 7.9 Hz, 1H); MS (ES) m/z 549 (M$^+$+1).

Reference Example 4.12

Preparation of
(20S)-7-methylamino-9-nitrocamptothecin
20-acetate

This compound was prepared from (20S)-7-chloro-9-nitrocamptothecin 20-acetate of Reference Example 3.1 and methylamine according to a manner analogous to those of Reference Example 4.1.

$^1$H NMR (270 MHz) δ (CDCl$_3$) 0.97 (t, J=5.1 Hz, 3H), 2.12–2.30 (m, 5H), 3.37 (d, J=3.2 Hz, 3H), 5.16 (br, 1H), 5.40 (d, J=11.6 Hz, 1H), 5.56 (s, 2H), 5.67 (d, J=11.6 Hz, 1H), 7.14 (s, 1H), 7.72 (m, 2H), 8.25 (m, 1H); MS (ES) m/z 465 (M$^+$+1).

Reference Example 4.13

Preparation of
(20S)-7-(2-methylpropylamino)-9-nitrocamptothecin
20-acetate

This compound was prepared from (20S)-7-chloro-9-nitrocamptothecin 20-acetate of Reference Example 3.1 and isobutylamine according to a manner analogous to those of Reference Example 4.1.

$^1$H NMR (270 MHz) δ (CDCl$_3$) 0.97 (t, J=7.6 Hz, 3H), 1.06 (d, J=6.6 Hz, 6H), 1.81–2.01 (m, 1H), 2.05–2.36 (m, 5H), 3.39–3.52 (m, 2H), 5.08 (br, 1H), 5.40 (d, J=17.2 Hz, 1H), 5.47 (s, 2H), 5.67 (d, J=17.2 Hz, 1H), 7.13 (s, 1H), 7.65 (dd, J=1.7, 7.8 Hz, 1H), 7.71 (t, J=7.8 Hz, 1H), 8.23 (dd, J=1.7, 7.8 Hz, 1H); MS (ES) m/z 507 (M$^+$+1).

Reference Example 4.14

Preparation of
(20S)-7-hexylamino-9-nitrocamptothecin 20-acetate

This compound was prepared from (20S)-7-chloro-9-nitrocamptothecin 20-acetate of Reference Example 3.1 and hexylamine according to a manner analogous to those of Reference Example 4.1.

$^1$H NMR (270 MHz) δ (CDCl$_3$) 0.87–1.03 (m, 6H), 1.24–1.59 (m, 6H), 1.60–1.78 (m, 2H), 2.05–2.37 (m, 5H), 3.58–3.70 (m, 2H), 5.02 (br, 1H), 5.40 (d, J=17.5 Hz, 1H), 5.47 (s, 2H), 5.67 (d, J=17.5 Hz, 1H), 7.13 (s, 1H), 7.66 (dd, J=2.0, 7.8 Hz, 1H), 7.71 (t, J=7.8 Hz, 1H), 8.23 (dd, J=2.0, 7.8 Hz, 1H); MS (ES) m/z 535 (M$^+$+1).

Reference Example 4.15

Preparation of
(20S)-7-butylamino-9-nitrocamptothecin 20-acetate

This compound was prepared from (20S)-7-chloro-9-nitrocamptothecin 20-acetate of Reference Example 3.1 and butylamine according to a manner analogous to those of Reference Example 4.1.

$^1$H NMR (270 MHz) δ (CDCl$_3$) 0.97 (t, J=7.6 Hz, 3H), 1.00 (t, J=7.3 Hz, 3H), 1.43–1.52 (m, 2H), 1.63–1.71 (m, 2H), 2.13–2.32 (m, 2H), 2.22 (s, 3H), 3.62–3.69 (m, 2H), 5.02 (brt, 1H), 5.40 (d, J=17.2 Hz, 1H), 5.47 (s, 2H), 5.66 (d, J=17.2 Hz, 1H), 7.14 (s, 1H), 7.65–7.74 (m, 2H), 8.23 (dd, J=1.6 and 7.9 Hz, 1H); MS m/z (ES) 507 (M$^+$+1).

Reference Example 4.16

Preparation of
(20S)-7-ethylamino-9-nitrocamptothecin 20-acetate

This compound was prepared from (20S)-7-chloro-9-nitrocamptothecin 20-acetate of Reference Example 3.1 and ethylamine according to a manner analogous to those of Reference Example 4.1.

$^1$H NMR (270 MHz) δ (CDCl$_3$) 0.97 (t, J=7.6 Hz, 3H), 1.36 (t, J=7.1 Hz, 3H), 2.12–2.30 (m, 5H), 3.70 (q, J=7.1 Hz, 1H), 3.72 (q, J=7.1 Hz, 1H), 4.96 (br, 1H), 5.40 (d, J=17.3 Hz, 1H), 5.46 (s, 2H), 5.67 (d, J=17.3 Hz, 1H), 7.13 (s, 1H), 7.67 (dd, J=2.6, 7.3 Hz, 1H), 7.71 (t, J=7.3 Hz, 1H), 8.23 (dd, J=2.6, 7.3 Hz, 1H); MS (ES) m/z 479 (M$^+$+1).

Reference Example 4.17

Preparation of (20S)-7-[2-(4-methoxyphenyl)ethylamino]-9-nitrocamptothecin 20-acetate This compound was prepared from (20S)-7-chloro-9-nitrocamptothecin 20-acetate of Reference Example 3.1 and 4-methoxyphenethylamine according to a manner analogous to those of Reference Example 4.1.

$^1$H NMR (270 MHz) δ (CDCl$_3$) 0.96 (t, J=7.6 Hz, 3H), 2.02–2.37 (m, 5H), 2.94 (t, J=6.3 Hz, 2H), 3.81 (s, 3H), 3.89 (q, J=6.3 Hz, 2H), 4.91 (br, 1H), 5.39 (d, J=17.2 Hz, 1H), 5.46 (s, 2H), 5.67 (d, J=17.2 Hz, 1H), 6.85–7.93 (m, 2H), 7.12 (s, 1H), 7.13–7.21 (m, 2H), 7.64–7.73 (m, 2H), 8.17–8.25 (m, 1H); MS (ES) m/z 585 (M$^+$+1).

Reference Example 4.18

Preparation of (20S)-7-[2-(4-chlorophenyl)ethylamino]-9-nitrocamptothecin 20-acetate This compound was prepared from (20S)-7-chloro-9-nitrocamptothecin 20-acetate of Reference Example 3.1 and 4-chlorophenethylamine according to a manner analogous to those of Reference Example 4.1.

$^1$H NMR (270 MHz) δ (CDCl$_3$) 0.97 (t, J=7.6 Hz, 3H), 2.02–2.37 (m, 5H), 2.97 (t, J=6.3 Hz, 2H), 3.89 (q, J=6.3 Hz, 2H), 4.90 (br, 1H), 5.39 (d, J=17.2 Hz, 1H), 5.45 (s, 2H), 5.66 (d, J=17.2 Hz, 1H), 7.17–7.38 (m, 5H), 7.65–7.70 (m, 2H), 8.20–8.24 (m, 1H); MS (ES) m/z 589 (M$^+$+1).

Reference Example 4.19

Preparation of (20S)-7-[2-(4-fluorophenyl)ethylamino]-9-nitrocamptothecin 20-acetate This compound was prepared from (20S)-7-chloro-9-nitrocamptothecin 20-acetate of Reference Example 3.1 and 4-fluorophenethylamine according to a manner analogous to those of Reference Example 4.1.

$^1$H NMR (270 MHz) δ (CDCl$_3$) 0.97 (t, J=7.4 Hz, 3H), 2.03–2.38 (m, 5H), 2.97 (t, J=6.6 Hz, 2H), 3.91 (q, J=6.6 Hz, 2H), 4.91 (br, 1H), 5.39 (d, J=17.2 Hz, 1H), 5.46 (s, 2H), 5.67 (d, J=17.2 Hz, 1H), 6.91–7.27 (m, 5H), 7.66–7.73 (m, 2H), 8.21–8.24 (m, 1H, H-10); MS (ES) m/z 573 (M$^+$+1).

Reference Example 4.20

Preparation of
(20S)-7-(1-methylethylamino)-9-nitrocamptothecin
20-acetate

This compound was prepared from (20S)-7-chloro-9-nitrocamptothecin 20-acetate of Reference Example 3.1 and isopropylamine according to a manner analogous to those of Reference Example 4.1.

$^1$H NMR (270 MHz) δ (CDCl$_3$) 0.97 (t, J=7.6 Hz, 3H), 1.32 (dd, J=2.0, 6.3 Hz, 6H), 2.05–2.37 (m, 5H), 3.97–4.15 (m, 1H), 4.92 (d, J=7.9 Hz, 1H), 5.32 (s, 2H), 5.40 (d, J=17.2 Hz, 1H), 5.68 (d, J=17.2 Hz, 1H), 7.14 (s, 1H), 7.66 (dd, J=1.7, 8.3 Hz, 1H), 7.72 (dd, J=7.6, 8.3 Hz, 1H), 8.23 (dd, J=1.7, 8.3 Hz, 1H); MS (ES) m/z 493 (M$^+$+1).

Reference Example 4.21

Preparation of (20S)-7-(3,3-dimethylbutylamino)-9-nitrocamptothecin 20-acetate

This compound was prepared from (20S)-7-chloro-9-nitrocamptothecin 20-acetate of Reference Example 3.1 and 3,3-dimethylbutylamine according to a manner analogous to those of Reference Example 4.1.

$^1$H NMR (270 MHz) δ (CDCl$_3$) 0.97 (t, J=7.6 Hz, 3H), 1.01 (s, 9H), 1.54–1.63 (m, 2H), 2.04–2.37 (m, 5H), 3.56–3.70 (m, 2H), 4.91 (t, J=5.0 Hz, 1H), 5.40 (d, J=17.2 Hz, 1H), 5.48 (s, 2H), 5.67 (d, J=17.2 Hz, 1H), 7.14 (s, 1H), 7.67–7.74 (m, 2H), 8.23 (dd, J=2.8, 7.1 Hz, 1H); MS (ES) m/z 535 (M$^+$+1).

Reference Example 4.22

Preparation of
(20RS)-10-methyl-9-nitro-7-pentylaminocamptothecin
20-acetate

This compound was prepared from (20RS)-7-chloro-10-methyl-9-nitrocamptothecin 20-acetate of Reference Example 3.2 and pentylamine according to a manner analogous to those of Reference Example 4.1.

$^1$H NMR (270 MHz) δ (CDCl$_3$) 0.85–1.00 (m, 6H), 1.25–1.53 (m, 4H), 1.54–1.75 (m, 2H), 2.05–2.35 (m, 5H), 2.42 (s, 3H), 3.57–3.70 (m, 2H), 4.89–5.00 (m, 1H), 5.39 (d, J=17.2 Hz, 1H), 5.45 (s, 2H), 5.67 (d, J=17.2 Hz, 1H), 7.11 (s, 1H), 7.57 (d, J=8.9 Hz, 1H), 8.05 (d, J=8.9 Hz, 1H); MS (ES) m/z 535 (M$^+$+1).

Reference Example 4.23

Preparation of
(20S)-7-(2-hydroxyethylamino)-9-nitrocamptothecin
20-acetate

This compound was prepared from (20S)-7-chloro-9-nitrocamptothecin 20-acetate of Reference Example 3.1 and ethanolamine according to a manner analogous to those of Reference Example 4.1.

$^1$H NMR (270 MHz) δ (CDCl$_3$) 0.97 (t, J=7.6 Hz, 3H), 2.02–2.37 (m, 6H), 2.57 (br, 1H), 3.70–3.84 (m, 2H), 3.85–4.01 (m, 2H), 5.38 (d, J=17.5 Hz, 1H), 5.44 (s, 2H), 5.65 (d, J=17.5 Hz, 1H), 7.14 (s, 1H), 7.59–7.75 (m, 2H), 8.17–8.25 (m, 1H); MS (ES) m/z 495 (M$^+$+1).

Reference Example 5.1

Preparation of
(20S)-9-amino-7-(butylamino)camptothecin
20-acetate (20S)-7-butylamino-9-nitrocamptothecin 20-acetate (156 mg, 0.31 mmol) of Reference Example 4.15 was dissolved into MeOH (10 ml) and 1N HCl aqueous solution (2 ml). 5% Pd—C (15 mg) was added and the hydrogenation was carried out under H$_2$ atmosphere using a balloon at room temperature for 1 hr. After removing Pd—C by filtration, the filtrate was concentrated under reduced pressure to obtain the product (137 mg, 87% yield).

$^1$H NMR (270 MHz) δ (CDCl$_3$) 0.95 (t, J=7.6 Hz, 3H), 1.01 (t, J=7.3 Hz, 3H), 1.48–1.60 (m, 2H), 1.68–1.78 (m, 2H), 2.10–2.31 (m, 2H), 2.20 (s, 3H), 3.60–3.67 (m, 2H), 3.90 (brs, 2H), 5.39 (d, J=17.0 Hz, 1H), 5.41 (s, 2H), 5.66 (d, J=17.0 Hz, 1H), 6.85 (d, J=7.3 Hz, 1H), 7.11 (s, 1H), 7.45 (dd, J=7.3 and 8.3 Hz, 1H), 7.64 (d, J=8.3 Hz, 1H), 8.77 (brs, 1H); MS (ES) m/z 477 (M$^+$+1).

Reference Example 5.2

Preparation of (20S)-9-amino-7-[2-(morpholinyl)ethylamino]camptothecin 20-acetate This compound was prepared from (20S)-7-[2-(morpholinyl)ethylamino]-9-nitrocamptothecin 20-acetate of Reference Example 4.2 according to a manner analogous to those of Example 5.1.

$^1$H NMR (400 MHz) δ (CDCl$_3$) 0.96 (t, J=8.4 Hz, 3H), 2.09–2.27 (m, 2H), 2.21 (s, 3H), 2.53–2.55 (m, 4H), 2.69–2.72 (m, 2H), 3.71–3.76 (m, 6H), 4.47 (brs, 2H), 5.32 (d, J=17.6 Hz, 1H), 5.35 (d, J=17.6 Hz, 1H), 5.39 (d, J=17.2 Hz, 1H), 5.65 (d, J=17.2 Hz, 1H), 6.79 (d, J=8.0 Hz, 1H), 7.12 (s, 1H), 7.45 (dd, J=7.6 and 8.0 Hz, 1H), 7.57 (d, J=7.6 Hz, 1H), 8.37 (brt, 1H); MS (ES) m/z 534 (M$^+$+1).

Reference Example 5.3

Preparation of (20S)-9-amino-7-[3-(dimethylamino)propylamino]camptothecin 20-acetate hydrochloride This compound was prepared from (20S)-7-[3-(dimethylamino)propylamino]-9-nitrocamptothecin 20-acetate of Reference Example 4.3 according to a manner analogous to those of Example 5.1.

$^1$H NMR (270 MHz) δ (D2O) 0.88 (t, 3H), 2.01–2.27 (m, 4H), 2.18 (s, 3H), 2.85 (s, 6H), 3.26–3.32 (m, 2H), 3.87 (t, J=7.3 Hz, 2H), 5.44 (d, J=17.0 Hz, 1H), 5.49 (s, 2H), 5.61 (d, J=17.0 Hz, 1H), 7.10 (d, J=8.0 Hz, 1H), 7.40 (d, J=7.6 Hz, 1H), 7.62 (dd, J=7.6 and 8.0 Hz, 1H); MS (ES) m/z 506 (M$^+$+1).

Reference Example 5.4

Preparation of
(20S)-9-amino-7-(propylamino)camptothecin
20-acetate

This compound was prepared from (20S)-9-nitro-7-(propylamino)camptothecin 20-acetate of Reference Example 4.4 according to a manner analogous to those of Reference Example 5.1.

$^1$H NMR (270 MHz) δ (CDCl$_3$) 0.95 (t, J=7.6 Hz, 3H), 1.09)t, J=7.3 Hz, 3H), 1.69–1.83 (m, 2H), 2.06–2.31 (m,

2H), 2.23 (s, 3H), 3.53–3.60 (m, 2H), 3.93 (brs, 2H), 5.35 (s, 2H), 5.38 (d, J=17.5 Hz, 1H), 5.59 (d, J=17.5 Hz, 1H), 6.82 (d, J=7.3 Hz, 1H), 7.10 (s, 1H), 7.43 (dd, J=7.3 and 8.6 Hz, 1H), 7.62 (d, J=8.6 Hz, 1H), 8.79 (brt, 1H); MS (ES) m/z 463 (M$^+$+1).

Reference Example 5.5

Preparation of
(20S)-9-amino-7-(phenethylamino)camptothecin
20-acetate

This compound was prepared from (20S)-9-nitro-7-(phenethylamino)camptothecin 20-acetate of Reference Example 4.6 according to a manner analogous to those of Reference Example 5.1.
$^1$H NMR (400 MHz) δ (CDCl$_3$) 0.95 (t, J=7.6 Hz, 3H), 2.10–2.30 (m, 2H), 2.20 (s, 3H), 3.05 (t, J=6.4 Hz, 2H), 3.47 (brs, 2H), 3.97 (m, 2H), 5.40 (d, J=17.2 Hz, 1H), 5.43 (s, 2H), 5.67 (d, J=17.2 Hz, 1H), 6.75 (d, J=7.2 Hz, 1H), 7.00 (s, 1H), 7.26–7.34 (m, 5H), 7.42 (dd, J=7.2 and 8.8 Hz, 1H), 7.61 (d, J=8.8 Hz, 1H), 8.68 (brs, 1H); MS (ES) m/z 525 (M$^+$+1).

Reference Example 5.6

Preparation of
(20S)-9-amino-7-(3-phenylpropylamino)camptothecin
20-acetate

This compound was prepared from (20S)-9-nitro-7-(3-phenylpropylamino)-camptothecin 20-acetate of Reference Example 4.7 according to a manner analogous to those of Reference Example 5.1.
$^1$H NMR (270 MHz) δ (CDCl$_3$) 0.94(t, J=7.6 Hz, 3H), 2.07 (m, 2H), 2.02–2.31 (m, 2H), 2.19 (s, 3H), 2.82 (t, J=7.6 Hz, 2H), 3.65 (dt, J=5.3 and 6.6 Hz, 2H), 3.81 (brs, 2H), 5.34 (s, 2H), 5.39 (d, J=17.2 Hz, 1H), 5.66 (d, J=17.2 Hz, 1H), 6.84 (d, J=6.9 Hz, 1H), 7.11 (s, 1H), 7.17–7.33 (m, 5H), 7.44 (dd, J=7.4 and 8.4 Hz, 1H), 7.64 (d, J=8.6 Hz, 1H), 8.84 (m, 1H); MS (ES) m/z 539 (M$^+$+1).

Reference Example 5.7

Preparation of (20S)-9-amino-7-[2-(pyridin-2-yl)ethylamino]camptothecin 20-acetate This compound was prepared from (20S)-9-nitro-7-[2-(pyridin-2-yl)ethylamino]camptothecin 20-acetate of Reference Example 4.8 according to a manner analogous to those of Reference Example 5.1.
MS (ES) m/z 526 (M$^+$+1).

Reference Example 5.8

Preparation of (20S)-9-amino-7-[2-(pyridin-3-yl)ethylamino]camptothecin 20-acetate Hydrochloride This compound was prepared from (20S)-9-nitro-7-[2-(pyridin-3-yl)ethylamino]camptothecin 20-acetate of Reference Example 4.9 according to a manner analogous to those of Reference Example 5.1.
$^1$H NMR (270 MHz) δ (CDCl$_3$) 0.94 (t, J=7.3 Hz, 3H), 2.05 (m, 2H), 3.37 (m, 2H), 4.26 (t, J=6.9 Hz, 2H), 5.52 (m, 2H), 5.61 (s, 2H), 7.13 (d, J=7.4 Hz, 1H), 7.69 (d, J=7.4 and 8.4 Hz, 1H), 7.85 (d, J=8.4 Hz, 1H), 8.06 (dd, J=5.4 and 7.9 Hz, 1H), 8.30 (s, 1H), 8.62 (d, J=7.9 Hz, 1H), 8.86 (d, J=5.4 Hz, 1H), 9.01 (s, 1H); MS(ES) m/z 526 (M$^+$+1).

Reference Example 5.9

Preparation of
(20S)-9-amino-7-(benzylamino)camptothecin
20-acetate hydrochloride This compound was prepared from (20S)-7-(benzylamino)-9-nitrocamptothecin 20-acetate of Reference Example 4.5 according to a manner analogous to those of Reference Example 5.1.
MS (ES) m/z 511 (M$^+$+1).

Reference Example 5.10

Preparation of
(20S)-9-amino-7-(heptylamino)camptothecin
20-acetate

This compound was prepared from (20S)-7-heptylamino-9-nitrocamptothecin 20-acetate of Reference Example 4.11 according to a manner analogous to those of Reference Example 5.1.
$^1$H NMR (270 MHz) δ (CDCl$_3$) 0.87–0.97 (m, 6H), 1.31–1.51 (m, 8H), 1.68–1.79 (m, 2H), 2.13–2.30 (m, 5H), 3.62 (q, J=6.9 Hz, 2H), 3.91 (br, 2H), 5.39 (d, J=17.2 Hz, 1H), 5.40 (s, 2H), 5.66 (d, J=17.2 Hz, 1H), 6.84 (d, J=7.6 Hz, 1H), 7.11 (s, 1H), 7.44 (dd, J=7.3, 8.6 Hz, 1H), 7.63 (d, J=8.6 Hz, 1H), 8.76 (br, 1H); MS (ES) m/z 519 (M$^+$+1).

Reference Example 5.11

Preparation of
(20S)-9-amino-7-(methylamino)camptothecin
20-acetate

This compound was prepared from (20S)-7-methylamino-9-nitrocamptothecin 20-acetate of Reference Example 4.12 according to a manner analogous to those of Reference Example 5.1.
S (ES) m/z 435 (M$^+$+1).

Reference Example 5.12

Preparation of
(20S)-9-amino-7-(2-methylpropylamino)camptothecin
20-acetate hydrochloride This compound was prepared from (20S)-7-(2-methylpropylamino)-9-nitrocamptothecin 20-acetate of Reference Example 4.13 according to a manner analogous to those of Reference Example 5.1.
MS (ES) m/z 477 (M$^+$+1).

Reference Example 5.13

Preparation of
(20S)-9-amino-7-hexylaminocamptothecin
20-acetate hydrochloride

This compound was prepared from (20S)-7-hexylamino-9-nitrocamptothecin 20-acetate of Reference Example 4.14 according to a manner analogous to those of Reference Example 5.1.
MS (ES) m/z 505 (M$^+$+1).

Reference Example 5.14

Preparation of (20S)-9-amino-7-(pentylamino)camptothecin 20-acetate hydrochloride This compound was prepared from (20S)-9-nitro-7-(pentylamino)camptothecin 20-acetate of Reference Example 4.1 according to a manner analogous to those of Reference Example 5.1.

MS (ES) m/z 491 ($M^+$+1).

Reference Example 5.15

Preparation of (20S)-9-amino-7-(ethylamino)camptothecin 20-acetate hydrochloride This compound was prepared from (20S)-7-ethylamino-9-nitrocamptothecin 20-acetate of Reference Example 4.16 according to a manner analogous to those of Reference Example 5.1.

MS (ES) m/z 449 ($M^+$+1).

Reference Example 5.16

Preparation of (20S)-9-amino-7-[2-(4-methoxyphenyl)ethylamino]camptothecin 20-acetate hydrochloride This compound was prepared from (20S)-7-[2-(4-methoxyphenyl)ethylamino]-9-nitrocamptothecin 20-acetate of Reference Example 4.17 according to a manner analogous to those of Reference Example 5.1.

MS (ES) m/z 555 ($M^+$+1).

Reference Example 5.17

Preparation of (20S)-9-amino-7-[2-(4-chlorophenyl)ethylamino]camptothecin 20-acetate hydrochloride This compound was prepared from (20S)-7-[2-(4-chlorophenyl)ethylamino]-9-nitrocamptothecin 20-acetate of Reference Example 4.18 according to a manner analogous to those of Reference Example 5.1.

MS (ES) m/z 559 ($M^+$+1).

Reference Example 5.18

Preparation of (20S)-9-amino-7-[2-(4-fluorophenyl)ethylamino]camptothecin 20-acetate hydrochloride This compound was prepared from (20S)-7-[2-(4-fluorophenyl)ethylamino]-9-nitrocamptothecin 20-acetate of Reference Example 4.19 according to a manner analogous to those of Reference Example 5.1.

MS (ES) m/z 543 ($M^+$+1).

Reference Example 5.19

Preparation of (20S)-9-amino-7-(1-methylethylamino)camptothecin 20-acetate Hydrochloride This compound was prepared from (20S)-7-(1-methylethylamino)-9-nitrocamptothecin 20-acetate of Reference Example 4.20 according to a manner analogous to those of Reference Example 5.1.

MS (ES) m/z 463 ($M^+$+1).

Reference Example 5.20

Preparation of (20S)-9-amino-7-(3,3-dimethylbutylamino)camptothecin 20-acetate hydrochloride This compound was prepared from (20S)-7-(3,3-dimethylbutylamino)-9-nitrocamptothecin 20-acetate of Reference Example 4.21 according to a manner analogous to those of Reference Example 5.1.

MS (ES) m/z 505 ($M^+$+1).

Reference Example 5.21

Preparation of (20S)-9-amino-7-(3-methylbutylamino)camptothecin 20-acetate hydrochloride This compound was prepared from (20S)-7-(3-methylbutylamino)-9-nitrocamptothecin 20-acetate according of Reference Example 4.10 to a manner analogous to those of Reference Example 5.1.

MS (ES) m/z 491 ($M^+$+1).

Reference Example 5.22

Preparation of (20RS)-9-amino-10-methyl-7-(pentylamino)camptothecin 20-acetate Hydrochloride This compound was prepared from (20RS)-10-methyl-9-nitro-7-(pentylamino)camptothecin 20-acetate of Reference Example 4.22 according to a manner analogous to those of Reference Example 5.1.

MS (ES) m/z 505 ($M^+$+1).

Reference Example 5.23

Preparation of (20S)-9-amino-7-(2-hydroxyethylamino)camptothecin 20-acetate hydrochloride This compound was prepared from (20S)-7-(2-hydroxyethylamino)-9-nitrocamptothecin 20-acetate of Reference Example 4.23 according to a manner analogous to those of Reference Example 5.1.

MS (ES) m/z 465 ($M^+$+1).

Example 1.1

Preparation of (9S)-1-butyl-9-ethyl-9-hydroxy-1H,12H-pyrano[3″,4″:6′,7′]indolizino[1′,2′:6,5]pyrido[4,3,2-de]quinazoline-2,10,13 (3H,9H,15H)-trione The preparation method comprises of the following two steps via compound (a).

(a) (9S)-9-acetoxy-1-butyl-9-ethyl-1H,12H-pyrano[3″,4″:6′,7′]indolizino[1′,2′:6,5]pyrido[4,3,2-de]quinazoline-2,10,13(3H,9H,15H)-trione (20S)-9-amino-7-(butylamino)camptothecin 20-acetate hydrochloride (123 mg, 0.24 mmol) of Reference Example 5.1 was dissolved into dry $CH_2Cl_2$ (5 ml) and cooled in an ice-bath. DIEA (390 μl, 2.3 mmol) and triphosgene (67 mg, 0.23 mmol) were added successively and the mixture was stirred for 1 hr. in the ice-bath. The reaction mixture was quenched with aqueous 1N HCl solution at 0° C., and extracted with $CH_2Cl_2$ (20 ml). The $CH_2Cl_2$ layer was washed with brine, dried over $MgSO_4$, and evaporated under reduced pressure. The residue obtained was purified by column chromatography (dichloromethane/acetone=15/1-7/1) to give a pure product (70 mg, 56%).

$^1$H NMR (270 MHz) δ (CDCl$_3$) 0.98 (t, J=7.7 Hz, 3H), 1.00 (t, J=7.3 Hz, 3H), 1.43–1.59 (m, 2H), 1.66–1.77 (m, 2H), 2.07–2.35 (m, 2H), 2.23 (s, 3H), 4.12–4.18 (m, 2H), 5.36 (s, 2H), 5.40 (d, J=17.4 Hz, 1H), 5.68 (d, J=17.4 Hz, 1H), 6.76 (dd, J=1.5 and 6.7 Hz, 1H), 7.16 (s, 1H), 7.56–7.67 (m, 2H), 9.24 (s, 1H); MS (ES) m/z 503(M$^+$+1).

(b) (9S)-1-butyl-9-ethyl-9-hydroxy-1H,12H-pyrano[3'',4'':6',7']indolizino[1',2':6,5]pyrido[4,3,2-de]quinazoline-2,10,13(3H,9H,15H)-trione To a solution of (9S)-9-acetoxy-1-butyl-9-ethyl-1H,12H-pyrano[3'',4'':6',7']indolizino[1',2':6,5]pyrido[4,3,2-de]quinazoline-2,10,13(3H,9H,15H)-trione (11.5 mg, 0.023 mmol) in MeOH (3 ml) cooled in an ice-bath was added anhydrous hydrazine (100 μl). The mixture was warmed to room temperature and stirred for 1 hr. Aqueous 1 N HCl solution was added dropwise to acidify the reaction mixture and the mixture was stirred for 1 hr. at room temperature. After concentrated under reduced pressure, the obtaining residue was extracted with $CH_2Cl_2$ (20 ml×3). The combined $CH_2Cl_2$ solution was washed with brine, dried over $MgSO_4$ and evaporated. The residue was purified by column chromatography (dichloromethane/methanol=30/1) to give pure product (6.1 mg, 58%).

$^1$H NMR (400 MHz) δ (DMSO) 0.87 (t, J=7.2 Hz, 3H), 0.96 (t, J=7.6 Hz, 3H), 1.39–1.47 (m, 2H), 1.64–1.70 (m, 2H), 1.81–1.91 (m, 2H), 4.03–4.07 (m, 2H), 5.42 (s, 2H), 5.43 (s, 2H), 6.51 (s, 1H), 6.77 (d, J=7.2 Hz, 1H), 7.24 (s, 1H), 7.41 (d, J=7.6 Hz, 1H), 7.61 (dd, J=7.2 and 7.6 Hz, 1H), 11.15 (brs, 1H); MS (ES) m/z 461(M$^+$+1).

Example 1.2

Preparation of (9S)-9-ethyl-9-hydroxy-1-[2-(4-morpholino)ethyl]-1H,12H-pyrano[3'',4'':6',7']indolizino[1',2':6,5]pyrido[4,3,2-de]quinazoline-2,10,13(3H,9H,15H)-trione hydrochloride This compound was prepared from (20S)-9-amino-7-(2-morpholinoethyl)-aminocamptothecin 20-acetate of Reference Example 5.2 according to a manner analogous to those of Example 1.1 in two steps via compound (a).

(a) (9S)-9-acetoxy-9-ethyl-1-[2-(4-morpholino)ethyl]-1H,12H-pyrano[3'',4'':6',7']indolizino[1',2':6,5]pyrido[4,3,2-de]quinazoline-2,10,13(3H,9H,15H)-trione $^1$H NMR (270 MHz) δ (CDCl$_3$) 0.98 (t, J=7.4 Hz, 3H), 2.11–2.35 (m, 2H), 2.24 (s, 3H), 2.53–2.57 (m, 4H), 2.66 (t, J=6.6 Hz, 2H), 3.68 (t, J=4.6 Hz, 4H), 4.24–4.40 (m, 2H), 5.41 (d, J=17.5 Hz, 1H), 5.44 (s, 2H), 5.68 (d, J=17.5 Hz, 1H), 6.74 (dd, J=2.0 and 6.3 Hz, 1H), 7.16 (s, 1H), 7.58–7.67 (m, 2H), 8.68 (brs, 1H); MS (ES) m/z 560 (M$^+$+1).

(b) (9S)-9-ethyl-9-hydroxy-1-[2-(4-morpholino)ethyl]-1H,12H-pyrano[3'',4'':6',7']indolizino[1',2':6,5]pyrido[4,3,2-de]quinazoline-2,10,13(3H,9H,15H)-trione hydrochloride $^1$H NMR (270 MHz) δ (DMSO-d$_6$) 0.87 (t, J=7.2 Hz, 3H), 1.84–1.90 (m, 2H), 2.44–2.52 (m, 4H), 2.60–2.65 (m, 2H), 3.55–3.58 (m, 4H), 4.20 (m, 2H), 5.42 (s, 2H), 5.49 (s, 2H), 6.49 (s, 1H), 6.78 (d, J=7.3 Hz, 1H), 7.25 (s, 1H), 7.42 (d, J=8.6 Hz, 1H), 7.61 (dd, J=7.3 and 8.6 Hz, 1H), 11.12 (brs, 1H); MS (ES) m/z 518 (M$^+$+1).

Example 1.3

Preparation of (9S)-9-ethyl-1-[3-(dimethylamino)propyl]-9-hydroxy-1H,12H-pyrano[3'',4'':6',7']indolizino[1',2':6,5]pyrido[4,3,2-de]quinazoline-2,10,13(3H,9H,15H)-trione hydrochloride This compound was prepared from (20S)-9-amino-7-[3-(dimethylamino)-propylamino]camptothecin 20-acetate of Reference Example 5.3 according to a manner analogous to those of Example 1.1 in two steps via compound (a).

(a) (9S)-9-acetoxy-9-ethyl-1-[3-(dimethylamino)propyl]-1H,12H-pyrano[3'',4'':6',7']indolizino[1',2':6,5]pyrido[4,3,2-de]quinazoline-2,10,13(3H,9H,15H)-trione $^1$H NMR (270 MHz) δ (CDCl$_3$) 0.88 (t, J=7.6 Hz, 3H), 1.84–1.95 (m, 2H), 2.07–2.34 (m, 2H), 2.23 (s, 9H), 2.46 (t, J=6.8 Hz, 2H), 4.21 (t, J=7.5 Hz, 2H), 5.40 (d, J=17.2 Hz, 1H), 5.46 (s, 2H), 5.68 (d, J=17.2 Hz, 1H), 6.74 (dd, J=1.8 and 6.8 Hz, 1H), 7.15 (s, 1H), 7.55–7.65 (m, 2H); MS (ES) m/z 532 (M$^+$+1).

(b) (9S)-9-ethyl-1-[3-(dimethylamino)propyl]-9-hydroxy-1H,12H-pyrano[3'',4'':6',7']indolizino[1',2':6,5]pyrido[4,3,2-de]quinazoline-2,10,13(3H,9H,15H)-trione hydrochloride $^1$H NMR (270 MHz) δ (DMSO-d$_6$) 0.88 (t, J=7.6 Hz, 3H), 1.80–1.94 (m, 2H), 2.08–2.19 (m, 2H), 2.73 (s, 6H), 3.14–3.20 (m, 2H), 4.13–4.19 (m, 2H), 5.43 (s, 2H), 5.47 (s, 2H), 6.53 (s, 1H), 6.82 (dd, J=1.0 and 7.6 Hz, 1H), 7.44 (dd, J=1.0 and 8.2 Hz, 1H), 7.63 (dd, J=7.6 and 8.2 Hz, 1H), 10.28 (s, 1H), 11.23 (s, 1H); MS (ES) m/z 490 (M$^+$+1).

Example 1.4

Preparation of (9S)-9-ethyl-9-hydroxy-1-propyl-1H,12H-pyrano[3'',4'':6',7']indolizino[1',2':6,5]pyrido[4,3,2-de]quinazoline-2,10,13(3H,9H,15H)-trione This compound was prepared from (20S)-9-amino-7-(propylamino)camptothecin 20-acetate of Reference Example 5.4 according to a manner analogous to those of Example 1.1 in two steps via compound (a).

(a) (9S)-9-acetoxy-9-ethyl-1-propyl-1H,12H-pyrano[3'',4'':6',7']indolizino[1',2':6,5]pyrido[4,3,2-de]quinazoline-2,10,13(3H,9H,15H)-trione $^1$H NMR (270 MHz) δ (CD$_3$OD) 0.98 (t, J=7.6 Hz, 3H), 1.05 (t, J=7.3 Hz, 3H), 1.71–1.80 (m, 2H), 2.10–2.24 (m, 2H), 2.19 (s, 3H), 5.36 (d, J=17.2 Hz, 1H), 5.44 (s, 2H), 5.56

(d, J=17.2 Hz, 1H), 6.76 (d, J=7.6 Hz, 1H), 7.25 (s, 1H), 7.43 (d, J=8.6 Hz, 1H), 7.59 (dd, J=7.6 and 8.6 Hz, 1H); MS (ES) m/z 489 (M$^+$+1).

(b) (9S)-9-ethyl-9-hydroxy-1-propyl-1H,12H-pyrano[3″,4″:6′,7′]indolizino[1′,2′:6,5]pyrido[4,3,2-de]quinazoline-2,10,13(3H,9H,15H)-trione $^1$H NMR (270 MHz) δ (DMSO-d$_6$) 0.88 (t, J=7.3 Hz, 3H), 0.98 (t, J=7.3 Hz, 3H), 1.66–1.75 (m, 2H), 1.82–1.90 (m, 2H), 3.97–4.03 (m, 2H), 5.41 (s, 2H), 5.42 (s, 2H), 6.49 (s, 1H), 6.76 (dd, J=1.0 and 7.6 Hz, 1H), 7.24 (s, 1H), 7.41 (dd, J=1.0 and 8.2 Hz, 1H), 7.60 (dd, J=7.6 and 8.2 Hz, 1H), 11.13 (s, 1H); MS (ES) m/z 447 (M$^+$+1).

Example 1.5

Preparation of (9S)-1-benzyl-9-ethyl-9-hydroxy-1H,12H-pyrano[3″,4″:6′,7′]indolizino[1′,2′:6,5]pyrido[4,3,2-de]quinazoline-2,10,13(3H,9H,15H)-trione This compound was prepared from (20S)-9-amino-7-(benzylamino)camptothecin 20-acetate of Reference Example 5.9 according to a manner analogous to those of Example 1.1 in two steps via compound (a).

(a) (9S)-9-acetoxy-1-benzyl-9-ethyl-1H,12H-pyrano[3″,4″:6′,7′]indolizino[1′,2′:6,5]pyrido[4,3,2-de]quinazoline-2,10,13(3H,9H,15H)-trione $^1$H NMR (270 MHz) δ (CDCl$_3$) 0.94 (t, J=7.3 Hz, 3H), 2.00–2.33 (m, 2H), 2.20 (s, 3H), 5.16 (s, 2H), 5.32 (d, J=17.2 Hz, 1H), 5.47 (s, 2H), 5.59 (d, J=17.2 Hz, 1H), 6.77 (m, 1H), 7.10 (s, 1H), 7.15–7.40 (m, 5H), 7.50–7.78 (m, 2H), 9.34 (brs, 1H); MS (ES) m/z 537 (M$^+$+1).

(b) (9S)-1-benzyl-9-ethyl-9-hydroxy-1H,12H-pyrano[3″,4″:6′,7′]indolizino[1′,2′:6,5]pyrido[4,3,2-de]quinazoline-2,10,13 (3H,9H,15H)-trione $^1$H NMR (270 MHz) δ (DMSO-d$_6$) 0.84 (t, J=7.3 Hz, 3H), 1.82 (q, J=7.3 Hz, 2H), 5.12 (s, 2H), 5.33 (s, 2H), 5.42 (s, 2H), 6.47 (s, 1H), 6.87 (d, J=7.6 Hz, 1H), 7.21 (s, 1H), 7.28–7.40 (m, 5H), 7.48 (d, J=8.6 Hz, 1H), 7.68 (dd, J=7.6 and 8.6 Hz, 1H), 11.33 (brs, 1H); MS (ES) m/z 495 (M$^+$+1).

Example 1.6

Preparation of (9S)-9-ethyl-9-hydroxy-1-phenethyl-1H,12H-pyrano[3″,4″:6′,7′]indolizino[1′,2′:6,5]pyrido[4,3,2-de]quinazoline-2,10,13(3H,9H,15H)-trione This compound was prepared from (20S)-9-amino-7-(phenethylamino)camptothecin 20-acetate of Reference Example 5.5 according to a manner analogous to those of Example 1.1 in two steps via compound (a).

(a) (9S)-9-acetoxy-9-ethyl-1-phenethyl-1H,12H-pyrano[3″,4″:6′,7′]indolizino[1′,2′:6,5]pyrido[4,3,2-de]quinazoline-2,10,13(3H,9H,15H)-trione $^1$H NMR (400 MHz) δ (CDCl$_3$) 0.98 (t, J=7.6 Hz, 3H), 2.11–2.33 (m, 2H), 2.23 (s, 3H), 3.05 (t, J=7.8 Hz, 2H), 4.35–4.41 (m, 2H), 5.41 (d, J=17.2 Hz, 1H), 5.44(s, 2H), 5.69 (d, J=17.2 Hz, 1H), 6.72 (dd, J=2.0 and 6.6 Hz, 1H), 7.16 (s, 1H), 7.22–7.36 (m, 5H), 7.60–7.68 (m, 2H), 8.08 (brs, 1H); MS (ES) m/z 551 (M$^+$+1).

(b) (9S)-9-ethyl-9-hydroxy-1-phenethyl-1H,12H-pyrano[3″,4″:6′,7′]indolizino[1′,2′:6,5]pyrido[4,3,2-de]quinazoline-2,10,13(3H,9H,15H)-trione $^1$H NMR (400 MHz) δ (DMSO-d$_6$) 0.88 (t, J=7.4 Hz, 3H), 1.74–1.92 (m, 2H), 3.03 (t, J=8.2 Hz, 2H), 4.24–4.32 (m, 2H), 5.43 (s, 2H), 5.53 (s, 2H), 6.53 (s, 1H), 6.77 (dd, J=1.2 and 7.4 Hz, 1H), 7.25 (s, 1H), 7.28 (m, 1H), 7.31–7.38 (m, 4H), 7.42 (dd, J=1.2 and 8.8 Hz, 1H), 7.61 (dd, J=7.4 and 8.8 Hz, 1H), 11.17 (brs, 1H); MS (ES) m/z 509 (M$^+$+1).

Example 1.7

Preparation of (9S)-9-ethyl-9-hydroxy-1-(3-phenyl-propyl)-1H,12H-pyrano[3′,4″:6′,7′]indolizino[1′,2′:6,5]pyrido[4,3,2-de]quinazoline-2,10,13(3H,9H,15H)-trione This compound was prepared from (20S)-9-amino-7-(3-phenylpropylamino)-camptothecin 20-acetate of Reference Example 5.6 according to a manner analogous to those of Example 1.1 in two steps via compound (a).

(a) (9S)-9-acetoxy-9-ethyl-1-(3-phenyl-propyl)-1H,12H-pyrano[3″,4″:6′,7′]indolizino[1′,2′:6,5]pyrido[4,3,2-de]quinazoline-2,10,13(3H,9H,15H)-trione $^1$H NMR (270 MHz) δ (CDCl$_3$) 0.98 (t, J=7.4 Hz, 3H), 2.10 (m, 2H), 2.10–2.32 (m, 2H), 2.23 (s, 3H), 2.83 (t, J=7.8 Hz, 2H), 4.21 (m, 2H), 5.31 (s, 2H), 5.41 (d, J=17.2 Hz, 1H), 5.68 (d, J=17.2 Hz, 1H), 6.72 (dd, J=1.8 and 6.8 Hz, 1H), 7.12–7.28 (m, 5H), 7.15 (s, 1H), 7.59 (dd, J=1.8 and 8.7 Hz, 1H), 7.63 (dd, J=6.8 and 8.7 Hz, 1H), 8.92 (brs, 1H); MS (ES) m/z 565 (M$^+$+1).

(b) (9S)-9-ethyl-9-hydroxy-1-(3-phenyl-propyl)-1H,12H-pyrano[3″,4″:6′,7′]indolizino[1′,2′:6,5]pyrido[4,3,2-de]quinazoline-2,10,13(3H,9H,15H)-trione $^1$H NMR (270 MHz) δ (DMSO-d$_6$) 0.88 (t, J=7.3 Hz, 3H), 1.79–1.91 (m, 2H), 1.94–2.12 (m, 2H), 2.74 (t, J=7.9 Hz, 2H), 4.13 (t, J=7.6 Hz, 2H), 5.43 (s, 2H), 5.47 (s, 2H), 6.49 (s, 1H), 6.77 (dd, J=1.0 and 7.6 Hz, 1H), 7.16 (m, 1H), 7.20–7.31 (m, 4H), 7.42 (dd, J=1.0 and 8.6 Hz, 1H), 7.61 (dd, J=7.6 and 8.6 Hz, 1H); MS (ES) m/z 523 (M$^+$+1).

Example 1.8

Preparation of (9S)-9-ethyl-9-hydroxy-1-[2-(pyridin-2-yl)ethyl]-1H,12H-pyrano[3″,4″:6′,7′]indolizino[1′,2′:6,5]pyrido[4,3,2-de]quinazoline-2,10,13(3H,9H,15H)-trione hydrochloride This compound was prepared from (20S)-9-amino-7-[2-(pyridin-2-yl)ethylamino]camptothecin 20-acetate of Reference Example 5.7 according to a manner analogous to those of Example 1.1 in two steps via compound (a).

(a) (9S)-9-acetoxy-9-ethyl-1-[2-(pyridin-2-yl)ethyl]-1H,12H-pyrano[3″,4″:6′,7′]indolizino[1′,2′:6,5]pyrido[4,3,2-de]quinazoline-2,10,13(3H,9H,15H)-trione ¹H NMR (270 MHz) δ (CDCl₃) 0.97 (t, J=7.6 Hz, 3H), 2.10–2.32 (m, 2H), 2.22 (s, 3H), 3.21 (t, J=7.9 Hz, 2H), 4.57 (m, 2H), 5.41 (d, J=17.2 Hz, 1H), 5.69 (d, J=17.2 Hz, 1H), 5.73 (dd, J=18.8 Hz, 1H), 5.83 (dd, J=18.8 Hz, 1H), 6.73 (dd, J=2.3 and 6.3 Hz, 1H), 7.13–7.27 (m, 3H), 7.58–7.66 (m, 3H), 8.43 (brs, 1H), 8.60 (d, J=4.6 Hz, 1H); MS (ES) m/z 552 (M⁺+1).

(b) (9S)-9-ethyl-9-hydroxy-1-[2-(pyridin-2-yl)ethyl]-1H,12H-pyrano[3″,4″:6′,7′]indolizino[1′,2′:6,5]pyrido[4,3,2-de]quinazoline-2,10,13(3H,9H,15H)-trione hydrochloride ¹H NMR (270 MHz) δ (DMSO-d₆) 0.87 (t, J=7.3 Hz, 3H), 1.84–1.88 (m, 2H), 3.18 (m, 2H), 4.45 (m, 2H), 5.42 (s, 2H), 5.61 (s, 2H), 6.50 (d, J=7.3 Hz, 1H), 6.80 (d, J=7.3 Hz, 1H), 7.26 (s, 1H), 7.27 (m, 1H), 7.36 (d, J=7.6 Hz, 1H), 7.45 (d, J=7.9 Hz, 1H), 7.64 (dd, J=7.3 and 7.6 Hz, 1H), 7.74 (ddd, J=2.0 and 7.6 and 7.9 Hz, 1H), 8.52 (m, 1H), 11.18 (brs, 1H); MS (ES) m/z 510 (M⁺+1).

Example 1.9

Preparation of (9S)-9-ethyl-9-hydroxy-1-[2-(pyridin-3-yl)ethyl]-1H,12H-pyrano[3″,4″:6′,7′]indolizino[1′,2′:6,5]pyrido[4,3,2-de]quinazoline-2,10,13(3H,9H,15H)-trione hydrochloride This compound was prepared from (20S)-9-amino-7-[2-(pyridin-3-yl)ethylamino]camptothecin 20-acetate of Reference Example 5.8 according to a manner analogous to those of Example 1.1 in two steps via compound (a).

(a) (9S)-9-acetoxy-9-ethyl-1-[2-(pyridin-3-yl)ethyl]-1H,12H-pyrano[3″,4″:6′,7′]indolizino[1′,2′:6,5]pyrido[4,3,2-de]quinazoline-2,10,13(3H,9H,15H)-trione ¹H NMR (270 MHz) δ (CDCl₃) 0.98 (t, J=7.4 Hz, 3H), 2.160–2.27 (m, 2H), 2.23 (s, 3H), 3.07 (t, J=7.3 Hz, 2H), 4.42 (m, 2H), 5.40 (d, J=17.2 Hz, 1H), 5.44 (s, 2H), 5.68 (d, J=17.2 Hz, 1H), 6.72 (dd, J=2.6 and 5.9 Hz, 1H), 7.17 (s, 1H), 7.28 (m, 1H), 7.59–7.70 (m, 3H), 8.13 (s, 1H), 8.52 (m, 2H); MS (ES) m/z 552 (M⁺+1).

(b) (9S)-9-ethyl-9-hydroxy-1-[2-(pyridin-3-yl)ethyl]-1H,12H-pyrano[3″,4″:6′,7′]indolizino[1′,2′:6,5]pyrido[4,3,2-de]quinazoline-2,10,13(3H,9H,15H)-trione hydrochloride ¹H NMR (270 MHz) δ (DMSO-d₆) 0.88 (t, J=7.3 Hz, 3H), 1.86 (q, J=7.3 Hz, 1H), 1.87 (q, J=7.3 Hz, 1H), 3.07 (t, J=7.6 Hz, 2H), 4.32 (m, 2H), 5.43 (s, 2H), 5.55 (s, 2H), 6.50 (s, 1H), 6.79 (d, J=7.6 Hz, 1H), 7.28 (s, 1H), 7.36 (dd, J=4.6 and 7.6 Hz, 1H), 7.46 (d, J=8.4 Hz, 1H), 7.64 (dd, J=7.8 and 8.4 Hz, 1H), 7.74 (d, J=7.8 Hz, 1H), 8.46 (d, J=4.6 Hz, 1H), 8.52 (s, 1H), 11.14 (brs, 1H); MS (ES) m/z 510 (M⁺+1).

Example 1.10

Preparation of (9S)-9-ethyl-9-hydroxy-1-(3-methylbutyl)-1H,12H-pyrano[3″,4″:6′,7′]indolizino[1′,2′:6,5]pyrido[4,3,2-de]quinazoline-2,10,13(3H,9H,15H)-trione This compound was prepared from (20S)-9-amino-7-(3-methylbutylamino)-camptothecin 20-acetate of Reference Example 5.21 according to a manner analogous to those of Example 1.1 in two steps via compound (a).

(a) (9S)-9-acetoxy-9-ethyl-1-(3-methylbutyl)-1H,12H-pyrano[3″,4″:6′,7′]indolizino[1′,2′:6,5]pyrido[4,3,2-de]quinazoline-2,10,13(3H,9H,15H)-trione ¹H NMR (270 MHz) δ (CDCl₃) 0.98 (t, J=7.6 Hz, 3H), 1.05 (d, J=6.6 Hz, 6H), 1.65 (m, 2H), 1.84 (m, 1H), 2.07–2.35 (m, 211), 2.23 (s, 3H), 4.18 (m, 2H), 536 (d, J=18.5 Hz, 1H), 5.40 (d, J=17.2 Hz, 1H), 5.43 (d, J=18.5 Hz, 1H), 5.68 (d, J=17.2 Hz, 1H), 6.73 (dd, J=2.0 and 6.8 Hz, 1H), 7.16 (s, 1H), 7.59 (dd, J=2.0 and 8.6 Hz, 1H), 7.64 (m, 1H), 8.66 (brs, 1H); MS (ES) m/z 517 (M⁺+1).

(b) (9S)-9-ethyl-9-hydroxy-1-(3-methylbutyl)-1H,12H-pyrano[3″,4″:6′,7′]indolizino[1′,2′:6,5]pyrido[4,3,2-de]quinazoline-2,10,13(3H,9H,15H)-trione ¹H NMR (270 MHz) δ (DMSO-d₆) 0.88 (t, J=7.3 Hz, 3H), 1.00 (d, J=6.6 Hz, 6H), 1.58–1.82 (m, 3H), 1.86 (q, J=7.3 Hz, 1H), 1.87 (q, J=7.3 Hz, 1H), 4.06 (t, J=7.9 Hz, 2H), 5.41 (s, 2H), 5.43 (s, 2H), 6.49 (s, 1H), 6.76 (dd, J=1.0 and 7.6 Hz, 1H), 7.24 (s, 1H), 7.40 (dd, J=1.0 and 8.6 Hz, 1H), 7.60 (dd, J=7.6 and 8.6 Hz, 1H), 11.13 (brs, 1H); MS (ES) m/z 475 (M⁺+1).

Example 1.11

Preparation of (9S)-9-ethyl-1-heptyl-9-hydroxy-1H,12H-pyrano[3″,4″:6′,7′]indolizino[1′,2′:6,5]pyrido[4,3,2-de]quinazoline-2,10,13(3H,9H,15H)-trione This compound was prepared from (20S)-9-amino-7-(heptylamino)camptothecin 20-acetate according of Reference Example 5.10 to a manner analogous to those of Example 1.1 in two steps via compound (a).

(a) (9S)-9-acetoxy-9-ethyl-1-heptyl-1H,12H-pyrano[3″,4″:6′,7′]indolizino[1′,2′:6,5]pyrido[4,3,2-de]quinazoline-2,10,13(3H,9H,15H)-trione ¹H NMR (270 MHz) δ (CDCl₃) 0.86 (t, J=6.6 Hz, 3H), 0.98 (t, J=7.4 Hz, 3H), 1.26–1.33 (m, 6H), 1.43–1.49 (m, 2H), 1.70–1.76 (m, 2H), 2.10–2.32 (m, 5H), 4.14–4.16 (m, 2H), 5.37 (s, 2H), 5.40 (d, J=17.1 Hz, 1H), 5.68 (d, J=17.1 Hz, 1H), 6.74 (dd, J=1.7, 6.6 Hz, 1H), 7.15 (s, 1H), 7.57–7.66 (m, 2H), 8.70 (br, 1H); MS (ES) m/z 545 (M⁺+1).

(b) (9S)-9-ethyl-1-heptyl-9-hydroxy-1H,12H-pyrano[3″,4″:6′,7′]indolizino[1′,2′:6,5]pyrido[4,3,2-de]quinazoline-2,10,13(3H,9H,15H)-trione ¹H NMR (270 MHz) δ (DMSO-d₆) 0.85–0.90 (m, 6H), 1.27–1.36 (m, 8H), 1.69–1.88 (m, 4H), 4.05 (m, 2H), 5.42 (s, 4H), 6.50 (br, 1H), 6.78 (d, J=7.6 Hz, 1H), 7.25 (s, 1H), 7.42 (d, J=7.6 Hz, 1H), 7.61 (t, J=7.6 Hz, 1H), 11.14 (s, 1H); MS (ES) m/z 503 (M⁺+1).

Example 1.12

Preparation of (9S)-9-ethyl-9-hydroxy-1-(2-methylpropyl)-1H,12H-pyrano[3″,4″:6′,7′]indolizino[1′,2′:6,5]pyrido[4,3,2-de]quinazoline-2,10,13(3H,9H,15H)-trione This compound was prepared from (20S)-9-amino-7-(2-methylpropylamino)-camptothecin 20-acetate of Reference Example 5.12 according to a manner analogous to those of Example 1.1 in two steps via compound (a).

(a) (9S)-9-acetoxy-9-ethyl-1-(2-methylpropyl)-1H, 12H-pyrano[3",4":6',7']indolizino[1',2':6,5]pyrido[4, 3,2-de]quinazoline-2,10,13(3H,9H,15H)-trione $^1$H NMR (270 MHz) δ (DMSO-d$_6$) 0.88–0.94 (m, 10H), 2.02–2.25 (m, 5H), 3.96 (d, J=7.9 Hz, 2H), 5.38 (s, 2H), 5.47 (s, 2H), 6.81 (d, J=7.9 Hz, 1H), 6.94 (s, 1H), 7.45 (d, J=7.9 Hz, 1H), 7.63 (t, J=7.9 Hz, 1H), 11.15 (br, 1H); MS (ES) m/z 503 (M$^+$+1).

(b) (9S)-9-ethyl-9-hydroxy-1-(2-methylpropyl)-1H, 12H-pyrano[3",4":6',7']indolizino[1',2':6,5]pyrido[4, 3,2-de]quinazoline-2,10,13(3H,9H,15H)-trione $^1$H NMR (270 MHz) δ (DMSO-d$_6$) 0.87 (t, J=7.3 Hz, 3H), 0.94 (d, J=6.6 Hz, 6H), 1.74–2.11 (m, 3H), 3.93–3.98 (m, 2H), 5.37 (s, 2H), 5.42 (s, 2H), 6.48 (s, 1H), 6.80 (d, J=7.6 Hz, 1H), 7.26 (s, 1H), 7.44 (d, J=7.6 Hz, 1H), 7.63 (t, J=7.6 Hz, 1H), 11.15 (br, 1H); MS (ES) m/z 461 (M$^+$+1).

Example 1.13

Preparation of (9S)-9-ethyl-1-hexyl-9-hydroxy-1H, 12H-pyrano[3",4":6',7']indolizino[1',2':6,5]pyrido[4, 3,2-de]quinazoline-2,10,13(3H,9H,15H)-trione This compound was prepared from (20S)-9-amino-7-(hexylamino)camptothecin 20-acetate of Reference Example 5.13 according to a manner analogous to those of Example 1.1 in two steps via compound (a).

(a) (9S)-9-acetoxy-9-ethyl-1-hexyl-1H,12H-pyrano [3",4":6',7']indolizino[1',2':6,5]pyrido-4,3,2-de] quinazoline-2,10,13(3H,9H,15H)-trione $^1$H NMR (270 MHz) δ (CDCl$_3$) 0.89 (t, J=7.1 Hz, 3H), 0.98 (t, J=7.6 Hz, 3H), 1.32–1.37 (m, 4H), 1.43–1.56 (m, 2H), 1.68–1.76 (m, 2H), 2.12–2.30 (m, 5H), 4.08–4.18 (m, 2H), 5.36 (s, 2H), 5.40 (d, J=17.5 Hz, 1H), 5.68 (d, J=17.5 Hz, 1H), 6.74 (dd, J=1.7, 6.6 Hz, 1H), 7.15 (s, 1H), 7.57–7.66 (m, 2H), 8.74 (br, 1H); MS (ES) m/z 531 (M$^+$+1).

(b) (9S)-9-ethyl-1-hexyl-9-hydroxy-1H,12H-pyrano [3",4":6',7']indolizino[1',2':6,5]pyrido[4,3,2-de] quinazoline-2,10,13(3H,9H,15H)-trione $^1$H NMR (270 MHz) δ (DMSO-d$_6$) 0.85–0.90 (m, 6H), 1.23–1.50 (m, 6H), 1.68–1.90 (m, 4H), 4.05 (m, 2H), 5.42 (s, 2H), 5.43 (s, 2H), 6.49 (s, 1H), 6.78 (d, J=8.0 Hz, 1H), 7.25 (s, 1H), 7.42 (d, J=8.0 Hz, 1H), 7.62 (t, J=8.0 Hz, 1H), 11.14 (br, 1H); MS (ES) m/z 489 (M$^+$+1).

Example 1.14

Preparation of (9S)-9-ethyl-9-hydroxy-1-pentyl-1H, 12H-pyrano[3",4":6',7']indolizino[1',2':6,5]pyrido[4, 3,2-de]quinazoline-2,10,13(3H,9H,15H)-trione This compound was prepared from (20S)-9-amino-7-(pentylamino)camptothecin 20-acetate of Reference Example 5.14 according to a manner analogous to those of Example 1.1 in two steps via compound (a).

(a) (9S)-9-acetoxy-9-ethyl-1-pentyl-1H,12H-pyrano [3",4":6',7']indolizino[1',2':6,5]pyrido[4,3,2-de] quinazoline-2,10,13(3H,9H,15H)-trione $^1$H NMR (270 MHz) δ (CDCl$_3$) 0.92 (t, J=6.9 Hz, 3H), 0.98 (t, J=7.6 Hz, 3H), 1.29–1.53 (m, 4H), 1.65–1.76 (m, 2H), 2.12–2.30 (m, 5H), 3.75–4.17 (m, 2H), 5.36 (s, 2H), 5.40 (d, J=17.5 Hz, 1H), 5.68 (d, J=17.5 Hz, 1H), 6.75 (dd, J=1.7, 6.9 Hz, 1H), 7.15 (s, 1H), 7.58 (dd, J=1.7, 6.9 Hz, 1H), 7.64 (dd, J=6.9, 8.6 Hz, 1H), 8.88 (br, 1H); MS (ES) m/z 517 (M$^+$+1).

(b) (9S)-9-ethyl-9-hydroxy-1-pentyl-1H,12H-pyrano [3",4":6',7']indolizino[1',2':6,5-]pyrido[4,3,2-de] quinazoline-2,10,13(3H,9H,15H)-trione $^1$H NMR (270 MHz) δ (DMSO-d$_6$) 0.85–0.93 (m, 6H), 1.36–1.38 (m, 4H), 1.69–1.88 (m, 4H), 4.05 (m, 2H), 5.43 (s, 4H), 6.49 (s, 1H), 6.78 (d, J=8.0 Hz, 1H), 7.25 (s, 1H), 7.42 (d, J=8.0 Hz, 1H), 7.61 (t, J=8.0 Hz, 1H), 11.13 (br, 1H); MS (ES) m/z 475 (M$^+$+1).

Example 1.15

Preparation of (9S)-1,9-diethyl-9-hydroxy-1H,12H-pyrano[3",4':6',7']indolizino[1',2':6,5]pyrido[4,3,2-de]quinazoline-2,10,13(3H,9H,15H)-trione This compound was prepared from (20S)-9-amino-7-(ethylamino)camptothecin 20-acetate of Reference Example 5.15 according to a manner analogous to those of Example 1.1 in two steps via compound (a).

(a) (9S)-9-acetoxy-1,9-diethyl-1H,12H-pyrano[3", 4":6',7']indolizino[1',2':6,5]pyrido[4,3,2-de]quinazo-line-2,10,13 (3H,9H,15H)-trione $^1$H NMR (270 MHz) δ (CDCl$_3$) 0.98 (t, J=7.6 Hz, 3H), 1.41 (t, J=7.3 Hz, 3H), 2.03–2.38 (m, 5H), 4.23 (q, J=7.3 Hz, 2H), 5.40 (d, J=17.2 Hz, 1H), 5.41 (s, 2H), 5.67 (d, J=17.2 Hz, 1H), 6.73 (dd, J=2.0, 6.6 Hz, 1H), 7.15 (s, 1H), 7.59 (dd, J=2.0, 8.6 Hz, 1H), 7.64 (dd, J=6.6, 8.6 Hz, 1H), 8.51 (br, 1H); MS (ES) m/z 475 (M$^+$+1).

(b) (9S)-1,9-diethyl-9-hydroxy-1H,12H-pyrano[3", 4":6',7']indolizino[1',2':6,5]pyrido[4,3,2-de]quinazo-line-2,10,13(3H,9H,15H)-trione $^1$H NMR (270 MHz) δ (DMSO-d$_6$) 0.87 (t, J=7.4 Hz, 3H), 1.30 (t, J=6.9 Hz, 3H), 1.84–1.88 (m, 2H), 4.09–4.12 (m, 2H), 5.42 (s, 2H), 5.46 (s, 2H), 6.49 (br, 1H), 6.78 (d, J=7.6 Hz, 1H), 7.25 (s, 1H), 7.42 (d, J=8.3 Hz, 1H), 7.61 (dd, J=7.6, 8.3 Hz, 1H), 11.12 (br, 1H); MS (ES) m/z 433 (M$^+$+1).

Example 1.16

Preparation of (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-2,10, 13(3H,9H,15H)-trione This compound was prepared from (20S)-9-amino-7-[2-(4-methoxyphenyl)-ethylamino]camptothecin 20-acetate of Reference Example 5.16 according to a manner analogous to those of Example 1.1 in two steps via compound (a).

(a) (9S)-9-acetoxy-9-ethyl-1-[2-(4-methoxyphenyl) ethyl]-1H,12H-pyrano[3",4":6',7']indolizino[1',2':6, 5]pyrido[4,3,2-de]quinazoline-2,10,13(3H,9H,15H)-trione $^1$H NMR (270 MHz) δ (CDCl$_3$) 0.99 (t, J=7.4 Hz, 3H), 2.03–2.38 (m, 5H), 2.98 (t, J=7.9 Hz, 2H), 3.72 (s, 3H), 4.23–4.50 (m, 2H), 5.42 (d, J=17.2 Hz, 1H), 5.44 (s, 2H), 5.69 (d, J=17.2 Hz, 1H), 6.74 (dd, J=2.0, 6.6 Hz, 1H), 6.83 (d, J=8.6 Hz, 2H), 7.16 (s, 1H), 7.22 (d, J=8.6 Hz, 2H), 7.60 (dd, J=2.0, 8.6 Hz, 1H), 7.65 (dd, J=6.6, 8.6 Hz, 1H), 8.52 (br, 1H); MS (ES) m/z 581 (M$^+$+1).

(b) (9S)-9-ethyl-9-hydroxy-1-[2-(4-methoxyphenyl) ethyl]-1H,12H-pyrano[3",4":6',7']indolizino[1',2':6, 5]pyrido[4,3,2-de]quinazoline-2,10,13(3H,9H,15H)-trione $^1$H NMR (270 MHz) δ (DMSO-d$_6$) 0.88 (t, J=7.3 Hz, 3H), 1.77–1.95 (m, 2H), 2.93–2.99 (m, 2H), 3.74 (s, 3H), 4.15–4.31 (m, 2H), 5.43 (s, 2H), 5.54 (s, 2H), 6.49 (s, 1H), 6.79 (d, J=8.0 Hz, 1H), 6.90 (d, J=8.9 Hz, 2H), 7.25 (d, J=8.9 Hz, 2H), 7.26 (s, 1H), 7.44 (d, J=8.0 Hz, 1H), 7.63 (t, J=8.0 Hz, 1H), 11.15 (br, 1H); MS (ES) m/z 539 (M$^+$+1).

Example 1.17

Preparation of (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-2,10,13(3H,9H,15H)-trione This compound was prepared from (20S)-9-amino-7-[2-(4-chlorophenyl)-ethylamino]camptothecin 20-acetate of Reference Example 5.17 according to a manner analogous to those of Example 1.1 in two steps via compound (a).

(a) (9S)-9-acetoxy-1-[2-(4-chlorophenyl)ethyl]-9-ethyl-1H,12H-pyrano[3",4":6',7']indolizino[1',2':6,5]pyrido[4,3,2-de]quinazoline-2,10,13(3H,9H,15H)-trione $^1$H NMR (270 MHz) δ (CDCl$_3$) 0.99 (t, J=7.4 Hz, 3H), 2.03–2.38 (m, 5H), 2.99 (t, J=7.9 Hz, 2H), 4.23–4.52 (m, 2H), 5.42 (d, J=17.2 Hz, 1H), 5.45 (s, 2H), 5.70 (d, J=17.2 Hz, 1H), 6.76 (dd, J=2.0, 6.6 Hz, 1H), 7.14–7.32 (m, 5H), 7.62 (dd, J=2.0, 8.6 Hz, 1H), 7.66 (dd, J=6.6, 8.6 Hz, 1H), 8.97 (br, 1H); MS (ES) m/z 585 (M$^+$+1).

(b) (9S)-1-[2-(4-chlorophenyl)ethyl]-9-ethyl-9-hydroxy-1H,12H-pyrano[3",4":6',7']indolizino[1',2':6, 5]pyrido[4,3,2-de]quinazoline-2,10,13(3H,9H,15H)-trione $^1$H NMR (270 MHz) δ (DMSO-d$_6$) 0.88 (t, J=7.3 Hz, 3H), 1.85–1.89 (m, 2H), 3.00–3.06 (m, 2H), 4.28–4.30 (m, 2H), 5.43 (s, 2H), 5.53 (s, 2H), 6.52 (s, 1H), 6.79 (d, J=7.6 Hz, 1H), 7.27 (s, 1H), 7.34 (d, J=8.6 Hz, 2H), 7.40 (d, J=8.6 Hz, 2H), 7.45 (d, J=8.6 Hz, 1H), 7.63 (dd, J=7.6, 8.6 Hz, 1H), 11.16 (br, 1H); MS (ES) m/z 543 (M$^+$+1).

Example 1.18

Preparation of (9S)-9-ethyl-1-[2-(4-fluorophenyl) ethyl]-9-hydroxy-1H,12H-pyrano[3",4":6',7']indolizino[1',2':6,5]pyrido[4,3,2-de]quinazoline-2,10, 13(3H,9H,15H)-trione This compound was prepared from (20S)-9-amino-7-[2-(4-fluorophenyl)ethylamino]camptothecin 20-acetate of Reference Example 5.18 according to a manner analogous to those of Example 1.1 in two steps via compound (a).

(a) (9S)-9-acetoxy-9-ethyl-1-[2-(4 fluorophenyl) ethyl]-H,12H-pyrano[3",4":6',7']indolizino[1',2':6,5] pyrido[4,3,2-de]quinazoline-2,10,13(3H,9H,15H)-trione $^1$H NMR (270 MHz) δ (CDCl$_3$) 0.99 (t, J=7.4 Hz, 3H), 2.03–2.38 (m, 5H), 3.00 (t, J=7.8 Hz, 2H), 4.21–4.55 (m, 2H), 5.42 (d, J=17.2 Hz, 1H), 5.44 (s, 2H), 5.70 (d, J=17.2 Hz, 1H), 6.77 (dd, J=2.0, 6.6 Hz, 1H), 6.94–7.01 (m, 2H), 7.18 (s, 1H), 7.21–7.33 (m, 2H), 7.61 (dd, J=2.0, 8.6 Hz, 1H), 7.66 (dd, J=6.6, 8.6 Hz, 1H), 8.89 (br, 1H); MS (ES) m/z 569 (M$^+$+1).

(b) (9S)-9-ethyl-1-[2-(4-fluorophenyl)ethyl]-9-hydroxy-1H,12H-pyrano[3",4":6',7']indolizino[1',2':6, 5]pyrido[4,3,2-de]quinazoline-2,10,13(3H,9H,15H)-trione $^1$H NMR (270 MHz) δ (DMSO-d$_6$) 0.88 (t, J=7.3 Hz, 3H), 1.85–1.91 (m, 2H), 3.00–3.06 (m, 2H), 4.27–4.29 (m, 2H), 5.43 (s, 2H), 5.54 (s, 2H), 6.52 (s, 1H), 6.79 (d, J=7.8 Hz, 1H), 7.16 (t, J=8.9 Hz, 2H), 7.27 (s, 1H), 7.36 (dd, J=5.6, 8.9 Hz, 2H), 7.45 (d, J=7.8 Hz, 1H), 7.63 (t, J=7.8 Hz, 1H), 11.16 (br, 1H); MS (ES) m/z 527 (M$^+$+1).

Example 1.19

Preparation of (9S)-9-ethyl-9-hydroxy-1-(1-methylethyl)-1H,12H-pyrano[3",4":6',7']indolizino[1',2':6, 5]pyrido[4,3,2-de]quinazoline-2,10,13(3H,9H,15H)-trione This compound was prepared from (20S)-9-amino-7-(1-methylethylamino)camptothecin 20-acetate according of Reference Example 5.19 to a manner analogous to those of Example 1.1 in two steps via compound (a).

(a) (9S)-9-acetoxy-9-ethyl-1-(1-methylethyl)-1H, 12H-pyrano[3",4":6',7']indolizino[1',2':6,5]pyrido[4, 3,2-de]quinazoline-2,10,13 (3H,9H,15H)-trione $^1$H NMR (270 MHz) δ (CDCl$_3$) 0.97 (t, J=7.4 Hz, 3H), 1.76 (d, J=6.6 Hz, 6H), 2.09–2.35 (m, 5H), 4.40–4.58 (m, 1H), 5.40 (d, J=17.2 Hz, 1H), 5.42 (s, 2H), 5.68 (d, J=17.2 Hz, 1H), 6.71 (dd, J=1.5, 7.1 Hz, 1H), 7.15 (s, 1H), 7.57 (dd, J=1.5, 8.6 Hz, 1H), 7.63 (dd, J=7.1, 8.6 Hz, 1H), 8.79 (br, 1H); MS (ES) m/z 489 (M$^+$+1).

(b) (9S)-9-ethyl-9-hydroxy-1-(1-methylethyl)-1H, 12H-pyrano[3",4":6',7']indolizino[1',2':6,5]pyrido[4, 3,2-de]quinazoline-2,10,13 (3H,9H,15H)-trione $^1$H NMR (270 MHz) δ (DMSO-d$_6$) 0.87 (t, J=7.3 Hz, 3H), 1.64 (d, J=6.6 Hz, 6H), 1.82–1.94 (m, 2H), 4.43–4.53 (m, 1H), 5.42 (s, 2H), 5.48 (s, 2H), 6.50 (s, 1H), 6.74 (d, J=7.9 Hz, 1H), 7.25 (s, 1H), 7.40 (d, J=7.9 Hz, 1H), 7.60 (t, J=7.9 Hz, 1H), 10.95 (br, 1H); MS (ES) m/z 447 (M$^+$+1).

Example 1.20

Preparation of (9S)-1-(3,3-dimethylbutyl)-9-ethyl-9-hydroxy-1H,12H-pyrano[3",4":6',7']indolizino[1',2': 6,5]pyrido[4,3,2-de]quinazoline-2,10,13(3H,9H, 15H)-trione This compound was prepared from (20S)-9-amino-7-(3, 3-dimetylbutylamino)-camptothecin 20-acetate of Reference Example 5.20 according to a manner analogous to those of Example 1.1 in two steps via compound (a).

(a) (9S)-9-acetoxy-1-(3,3-dimethylbutyl)-9-ethyl-1H,12H-pyrano[3",4":6',7']indolizino[1',2':6,5]pyrido[4,3,2-de]quinazoline-2,10,13(3H,9H,15H)-trione $^1$H NMR (270 MHz) δ (CDCl$_3$) 0.98 (t, J=7.4 Hz, 3H), 1.12 (s, 9H), 1.55–1.73 (m, 2H), 2.02–2.37 (m, 5H), 4.05–4.29 (m, 2H), 5.40 (d, J=17.2 Hz, 1H), 5.42 (s, 2H), 5.67 (d, J=17.2 Hz, 1H), 6.73 (dd, J=2.0, 6.6 Hz, 1H), 7.15 (s, 1H), 7.58 (dd, J=2.0, 8.6 Hz, 1H), 7.63 (dd, J=6.6, 8.6 Hz, 1H), 9.08 (br, 1H); MS (ES) m/z 531 (M$^+$+1).

(b) (9S)-1-(3,3-dimethylbutyl)-9-ethyl-9-hydroxy-1H,12H-pyrano[3",4":6',7']indolizino[1',2':6,5]pyrido[4,3,2-de]quinazoline-2,10,13(3H,9H,15H)-trione $^1$H NMR (270 MHz) δ (DMSO-d$_6$) 0.88 (t, J=7.3 Hz, 3H), 1.04 (s, 9H), 1.59–1.66 (m, 2H), 1.79–1.90 (m, 2H), 4.04 (m, 2H), 5.41 (s, 2H), 5.48 (S, 2H), 6.49 (s, 1H), 6.76 (dd, J=1.0, 7.6 Hz, 1H), 7.23 (s, 1H), 7.40 (dd, J=1.0, 8.6 Hz, 1H), 7.60 (dd, J=7.6, 8.6 Hz, 1H), 11.11 (br, 1H); MS (ES) m/z 489 (M$^+$+1).

Examples 2.1

Preparation of (9S)-1-butyl-9-ethyl-9-hydroxy-1H,12H-pyrano[3",4":6',7']indolizino[1',2':6,5]pyrido[4,3,2-de]quinazoline-10,13(9H,15H)-dione The preparation method comprises of the following two steps via compound (a).

(a) (9S)-9-acetoxy-1-butyl-9-ethyl-1H,12H-pyrano[3",4":6',7']indolizino[1',2':6,5]pyrido[4,3,2-de]quinazoline-10,13(9H,15H)-dione To a solution of (20S)-9-amino-7-(butylamino)camptothecin 20-acetate hydrochloride (14.9 mg, 0.029 mmol) of Reference Example 5.1 in dry CH$_2$Cl$_2$ (5 ml) were added trimethyl orthoformate (100 μl) and p-toluenesulfonic acid monohydrate (5 mg). The mixture was heated to reflux for 1 hr. in an oil bath. After cooling to room temperature, the mixture was washed with aqueous 1% NaHCO$_3$ solution and brine successively, dried over MgSO$_4$ and concentrated under reduced pressure. The obtaining residue was purified by column chromatography (eluent: dichloromethane/methanol=20/1) to give pure product (12.6 mg, 89%).

$^1$H NMR (400 MHz) δ (CDCl$_3$) 0.96 (t, J=7.6 Hz, 3H), 1.01 (t, J=7.4 Hz, 3H), 1.49–1.58 (m, 2H), 1.74–1.82 (m, 2H), 2.09–2.17 (m, 2H), 2.21 (s, 3H), 2.24–2.31 (m, 1H), 3.84 (t, J=7.4 Hz, 2H), 5.22 (d, J=17.8 Hz, 1H), 5.25 (d, J=17.8 Hz, 1H), 5.39 (d, J=17.2 Hz, 1H), 5.65 (d, J=17.2 Hz, 1H), 7.10 (s, 1H), 7.16 (d, J=7.2 Hz, 1H), 7.40 (s, 1H), 7.62 (d, J=8.4 Hz, 1H), 7.68 (dd, J=7.2 and 8.4 Hz, 1H); MS (ES) m/z 487(M$^+$+1).

(b) (9S)-1-butyl-9-ethyl-9-hydroxy-1H,12H-pyrano[3",4":6',7']indolizino[1',2':6,5]pyrido[4,3,2-de]quinazoline-10,13(9H,15H)-dione To a solution of (9S)-9-acetoxy-1-butyl-9-ethyl-1H,12H-pyrano[3",4":6',7']indolizino[1',2':6,5]pyrido[4,3,2-de]quinazoline-10,13(9H,15H)-dione (6.1 mg, 0.013 mmol) in MeOH (2 ml) cooled in an ice-bath was added anhydrous hydrazine (100 μl) and the mixture was stirred for 1 hr. at room temperature. Aqueous 1 N HCl solution was added dropwise to acidify the reaction mixture, and the mixture was stirred for 1 hr. at room temperature. After concentrated under reduced pressure, the residue was extracted with CH$_2$Cl$_2$ (30 ml) and the CH$_2$Cl$_2$ solution was washed with brine, dried over MgSO$_4$ and evaporated. The residue was purified by column chromatography (dichloromethane/methanol=20/1) to give pure product (3.9 mg, 70%).

$^1$H NMR (400 MHz) δ (DMDO-d$_6$) 1.02 (t, J=7.2 Hz, 6H), 1.50–1.59 (m, 2H), 1.76–1.93 (m, 4H), 3.82 (t, J=7.2 Hz, 2H), 3.88 (brs, 1H), 5.21 (s, 2H), 5.27 (d, J=16.2 Hz, 1H), 5.70 (d, J=16.2 Hz, 1H), 7.11 (dd, J=1.6 and 7.4 Hz, 1H), 7.37 (s, 1H), 7.51 (s, 1H), 7.59–7.67 (m, 2H); MS (ES) m/z 445(M$^+$+1).

Example 2.2

Preparation of (9S)-9-ethyl-9-hydroxy-1-[2-(4-morpholino)ethyl]-1H,12H-pyrano[3",4":6',7']indolizino[1',2':6,5]pyrido[4,3,2-de]quinazoline-10,13(9H,15H)dione hydrochloride This compound was prepared from (20S)-9-amino-7-[2-(4-morpholino)-ethylamino]camptothecin 20-acetate of Reference Example 5.2 according to a manner analogous to those of Example 2.1 in two steps via compound (a).

(a) (9S)-9-acetoxy-9-ethyl-1-[2-(4-morpholino)ethyl]-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.6 Hz, 3H), 2.09–2.34 (m, 2H), 2.21 (s, 3H), 2.53 (t, J=4.6 Hz, 4H), 2.71 (t, J=5.6 Hz, 2H), 3.70 (t, J=4.6 Hz, 4H), 3.91 (t, J=5.6 Hz, 2H), 5.21 (s, 2H), 5.38 (d, J=17.5 Hz, 1H), 5.65 (d, J=17.5 Hz, 1H), 7.09 (s, 1H), 7.17 (dd, J=1.5 and 7.3 Hz, 1H), 7.41 (s, 1H), 7.60–7.71 (m, 2H); MS (ES) m/z 544 (M$^+$+1).

(b) (9S)-9-ethyl-9-hydroxy-1-[2-(4-morpholino)ethyl]-1H,12H-pyrano[3",4":6',7']indolizino[1',2':6,5]pyrido[4,3,2-de]quinazoline-10,13(9H,15H)dione hydrochloride $^1$H NMR (270 MHz) δ (DMSO-d$_6$) 0.87 (t, J=7.3 Hz, 3H), 1.81–1.91 (m, 2H), 2.45–2.55 (m, 4H), 2.68–2.72 (m, 2H), 3.56 (t, J=4.3 Hz, 4H), 4.05–4.10 (m, 2H), 5.31 (s, 2H), 5.41 (s, 2H), 6.48 (s, 1H), 7.00 (d, J=7.6 Hz, 1H), 7.50 (d, J=8.2 Hz, 1H), 7.63 (dd, J=7.6 and 8.2 Hz, 1H), 7.71 (s, 1H); MS (ES) m/z 502 (M$^+$+1).

Example 2.3

Preparation of (9S)-9-ethyl-9-hydroxy-1-propyl-1H,12H-pyrano[3",4":6',7']indolizino[1',2':6,5]pyrido[4,3,2-de]quinazoline-10,13(9H,15H)-dione This compound was prepared from (20S)-9-amino-7-(propylamino)camptothecin 20-acetate of Reference Example 5.4 according to a manner analogous to those of Example 2.1 in two steps via compound (a).

(a) (9S)-9-acetoxy-9-ethyl-1-propyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.3 Hz, 3H), 1.12 (t, J=7.3 Hz, 3H), 1.77–1.91 (m, 2H), 2.08–2.31 (m, 2H), 2.21 (s, 3H), 3.81 (t, J=7.3 Hz, 2H), 5.23 (s, 2H), 5.38 (d, J=17.4 Hz, 1H), 5.65 (d, J=17.4 Hz, 1H), 7.09 (s, 1H), 7.17 (dd, J=1.7 and 7.3 Hz, 1H), 7.42 (s, 1H), 7.60–7.71 (m, 2H); MS (ES) m/z 473 (M$^+$+1).

(b) (9S)-9-ethyl-9-hydroxy-1-propyl-1H,12H-pyrano[3",4":6',7']indolizino[1',2':6,5]pyrido[4,3,2-de]quinazoline-10,13(9H,15H)-dione $^1$H NMR (270 MHz) δ (DMSO) 0.87 (t, J=7.3 Hz, 3H), 0.98 (t, J=7.3 Hz, 3H), 1.75–1.87 (m, 4H), 3.87–3.93 (m, 2H), 5.31 (s, 2H), 5.41 (s, 2H), 6.48 (s, 1H), 7.01 (dd, J=1.0 and 7.3 Hz, 1H), 7.19 (s, 1H), 7.49 (dd, J=1.0 and 8.6 Hz, 1H), 7.65 (dd, J=7.3 and 8.6 Hz, 1H), 7.83 (s, 1H); MS (ES) m/z 431 (M$^+$+1).

Example 2.4

Preparation of (9S)-1-benzyl-9-ethyl-9-hydroxy-1H,12H-pyrano[3",4":6',7']indolizino[1',2':6,5]pyrido[4,3,2-de]quinazoline-10,13(9H,15H)-dione This compound was prepared from (20S)-9-amino-7-(benzylamino)camptothecin 20-acetate of Reference Example 5.9 according to a manner analogous to those of Example 2.1 in two steps via compound (a).

(a) (9S)-9-acetoxy-1-benzyl-9-ethyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.92 (t, J=7.6 Hz, 3H), 2.01–2.29 (m, 2H), 2.18 (s, 3H), 5.02 (s, 2H), 5.12 (s, 2H), 5.31 (d, J=17.2 Hz, 1H), 5.57 (d, J=17.2H, 1H), 7.05 (s, 1H), 7.22 (dd, J=1.5 and 7.1 Hz, 1H), 7.31–7.46 (m, 5H), 7.46 (s, 1H), 7.66 (dd, J=1.5 and 8.6 Hz, 1H), 7.72 (dd, J=7.1 and 8.6 Hz, 1H); MS (ES) m/z 521 (M$^+$+1).

(b) (9S)-1-benzyl-9-ethyl-9-hydroxy-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.83 (t, J=7.4 Hz, 3H), 1.73–1.87 (m, 2H), 4.95 (d, J=18.5 Hz, 1H), 5.03 (d. J=18.5 Hz, 1H), 5.32 (s, 2H), 5.36(s, 2H), 6.45 (s, 1H), 7.09 (dd, J=1.0 and 7.6 Hz, 1H), 7.14 (s, 1H), 7.30–7.46 (m, 5H), 7.53 (dd, J=1.0 and 8.3 Hz, 1H), 7.70 (dd, J=7.6 and 8.3 Hz, 1H), 7.91 (s, 1H); MS (ES) m/z 479 (M$^+$+1).

Example 2.5

Preparation of (9S)-9-ethyl-9-hydroxy-1-phenethyl-1H,12H-pyrano[3",4":6',7']indolizino[1',2':6,5]pyrido[4,3,2-de]quinazoline-10,13(9H,15H)-dione This compound was prepared from (20S)-9-amino-7-(phenethylamino)camptothecin 20-acetate of Reference Example 5.5 according to a manner analogous to those of Example 2.1 in two steps via compound (a).

(a) (9S)-9-acetoxy-9-ethyl-1-phenethyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.97 (t, J=7.6 Hz, 3H), 2.10–2.32 (m, 2H), 2.22 (s, 3H), 3.08 (t, J=6.6 Hz, 2H), 4.09 (t, J=6.6 Hz, 2H), 5.30 (s, 2H), 5.40 (d, J=17.2 Hz, 1H), 5.67 (d, J=17.2H, 1H), 6.92 (s, 1H), 7.11–7.38 (m, 7H), 7.63–7.71 (m, 2H); MS (ES) m/z 535 (M$^+$+1).

(b) (9S)-9-ethyl-9-hydroxy-1-phenethyl-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.88 (t, J=7.4 Hz, 3H), 1.84–1.87 (m, 2H), 3.12 (m, 2H), 4.19 (m, 2H), 5.43 (s, 4H), 6.49 (s, 1H), 6.97 (dd, J=1.1 and 7.4 Hz, 1H), 7.21 (s, 1H), 7.27–7.35 (m, 5H), 7.50 (dd, J=1.1 and 8.6 Hz, 1H), 7.59 (s, 1H), 7.64 (dd, J=7.4 and 8.6 Hz, 1H); MS (ES) m/z 493 (M$^+$+1).

Example 2.6

Preparation of (9S)-2,9-diethyl-9-hydroxy-1-phenethyl-1H,12H-pyrano[3",4":6',7']indolizino[1',2':6,5]pyrido[4,3,2-de]quinazoline-10,13(9H,15H)-dione This compound was prepared from (20S)-9-amino-7-(phenethylamino)camptothecin 20-acetate of Reference Example 5.5 and triethyl orthopropionate according to a manner analogous to those of Example 2.1 in two steps via compound (a).

(a) (9S)-9-acetoxy-2,9-diethyl-1-phenethyl-1H,12H-pyrano[3",4":6',7']indolizino[1',2':6,5]-pyrido[4,3,2-de]quinazoline-10,13(9H,15H)-dione $^1$H NMR (270 MHz) δ (CDCl$_3$) 0.97 (t, J=7.6 Hz, 3H), 1.24 (t, J=7.3 Hz, 3H), 2.13–2.32 (m, 2H), 2.22 (s, 3H), 2.43 (q, J=7.3 Hz, 2H), 3.01 (t, J=6.9 Hz, 2H), 4.19 (t, J=6.9 Hz, 2H), 5.33 (s, 2H), 5.40 (d, J=17.2 Hz, 1H), 5.67 (d, J=17.2H, 1H), 7.13 (s, 1H), 7.14–7.37 (m, 6H), 7.62 (dd, J=1.3 and 8.6 Hz, 1H), 7.71 (dd, J=7.3 and 8.6 Hz, 1H); MS (ES) m/z 563 (M$^+$+1).

(b) (9S)-2,9-diethyl-9-hydroxy-1-phenethyl-1H,12H-pyrano[3",4":6',7']indolizino[1',2':6,5]-pyrido[4,3,2-de]quinazoline-10,13(9H,15H)-dione $^1$H NMR (270 MHz) δ (DMSO-d$_6$) 0.88 (t, J=7.3 Hz, 3H), 1.17 (t, J=7.3 Hz, 3H), 1.86 (m, 2H), 2.64 (q, J=7.3 Hz, 2H), 3.09 (t, J=7.6 Hz, 2H), 4.21 (t, J=7.6 Hz, 2H), 5.43 (s, 2H), 5.45 (s, 2H), 6.51 (s, 1H), 7.01 (dd, J=1.0 and 7.6 Hz, 1H), 7.22 (s, 1H), 7.25–7.36 (m, 5H), 7.50 (dd, J=1.0 and 8.6 Hz, 1H), 7.66 (dd, J=7.6 and 8.6 Hz, 1H); MS (ES) m/z 521 (M$^+$+1).

Example 2.7

Preparation of (9S)-9-ethyl-9-hydroxy-1-(3-phenylpropyl)-1H,12H-pyrano[3",4":6',7']indolizino[1',2':6,5]pyrido[4,3,2-de]quinazoline-10,13(9H,15H)-dione This compound was prepared from (20S)-9-amino-7-(3-phenylpropylamino)camptothecin 20-acetate of Reference Example 5.6 according to a manner analogous to those of Example 2.1 in two steps via compound (a).

(a) (9S)-9-acetoxy-9-ethyl-1-(3-phenylpropyl)-1H, 12H-pyrano[3",4":6',7']indolizino[1',2':6,5]pyrido[4, 3,2-de]quinazoline-10,13 (9H,15H)-dione $^1$H NMR (270 MHz) δ (CDCl$_3$) 0.96 (t, J=7.4 Hz, 3H), 2.05–2.34 (m, 4H), 2.23 (s, 3H), 2.83 (t, J=7.6 Hz, 2H), 3.84 (t, J=7.1 Hz, 2H), 5.16 (d, J=18.5 Hz, 1H), 5.22 (d, J=18.5 Hz, 1H), 5.39 (d, J=17.2 Hz, 1H), 5.66 (d, J=17.2 Hz, 1H), 7.09 (s, 1H), 7.15–7.32 (m, 6H), 7.34 (s, 1H), 7.62 (dd, J=1.7 and 8.6 Hz, 1H), 7.68 (dd, J=6.9 and 8.6 Hz, 1H); MS (ES) m/z 549 (M$^+$+1).

(b) (9S)-9-ethyl-9-hydroxy-1-(3-phenylpropyl)-1H, 12H-pyrano[3",4":6',7']indolizino[1',2':6,5]pyrido[4, 3,2-de]quinazoline-10,13(9H,15H)-dione $^1$H NMR (270 MHz) δ (DMSO-d$_6$) 0.87 (t, J=7.3 Hz, 3H), 1.85 (q, J=7.3 Hz, 1H), 1.86 (q, J=7.3 Hz, 1H), 2.11 (m, 2H), 2.74 (t, J=7.9 Hz, 2H), 4.00 (t, J=6.9 Hz, 2H), 5.33 (s, 2H), 5.41 (s, 2H), 6.48 (brs, 1H), 6.99 (dd, J=1.0 and 7.3 Hz, 1H), 7.18 (m, 1H), 7.19 (s, 1H), 7.27–7.30 (m, 4H), 7.48 (dd, J=1.0 and 8.4 Hz, 1H), 7.63 (dd, J=7.3 and 8.4 Hz, 1H), 7.82 (s, 1H); MS (ES) m/z 507 (M$^+$+1).

Example 2.8

Preparation of (9S)-9-ethyl-9-hydroxy-1-(3-methylbutyl)-1H,12H-pyrano[3",4":6',7']indolizino[1',2':6, 5]pyrido[4,3,2-de]quinazoline-10,13(9H,15H)-dione This compound was prepared from (20S)-9-amino-7-(3-methylbutylamino)-camptothecin 20-acetate of Reference Example 5.21 according to a manner analogous to those of Example 2.1 in two steps via compound (a).

(a) (9S)-9-acetoxy-9-ethyl-1-(3-methylbutyl)-1H, 12H-pyrano[3",4":6',7']indolizino[1',2':6,5]pyrido[4, 3,2-de]quinazoline-10,13(9H,15H)-dione $^1$H NMR (270 MHz) δ (CDCl$_3$) 0.96 (t, J=7.4 Hz, 3H), 1.04 (d, J=6.6 Hz, 6H), 1.85 (m, 1H), 2.09–2.31 (m, 2H), 2.21 (s, 3H), 3.85 (t, J=7.6 Hz, 2H), 5.24 (s, 2H), 5.39 (d, J=17.2 Hz, 1H), 5.66 (d, J=17.2H, 1H), 7.10 (s, 1H), 7.16 (dd, J=1.5 and 7.1 Hz, 1H), 7.40 (s, 1H), 7.62 (dd, J=1.5 and 8.4 Hz, 1H), 7.68 (dd, J=7.1 and 8.4 Hz, 1H); MS (ES) m/z 501 (M$^+$+1).

(b) (9S)-9-ethyl-9-hydroxy-1-(3-methylbutyl)-1H, 12H-pyrano[3",4":6',7']indolizino[1',2':6,5]pyrido[4, 3,2-de]quinazoline-10,13(9H,15H)-dione $^1$H NMR (270 MHz) δ (DMSO-d$_6$) 0.87 (t, J=7.4 Hz, 3H), 1.00 (d, J=5.9 Hz, 6H), 1.66–1.78 (m, 3H), 1.85 (q, J=7.4 Hz, 1H), 1.86 (q, J=7.4 Hz, 1H), 3.94 (t, J=7.3 Hz, 2H), 5.32 (s, 2H), 5.40 (s, 2H), 6.48 (s, 1H), 6.98 (dd, J=1.0 and 7.6 Hz, 1H), 7.17 (s, 1H), 7.46 (dd, J=1.0 and 8.3 Hz, 1H), 7.63 (dd, J=7.6 and 8.3 Hz, 1H), 7.82 (s, 1H); MS (ES) m/z 459 (M$^+$+1).

Example 2.9

Preparation of (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H, 15H)-dione This compound was prepared from (20S)-9-amino-7-(3-methylbutylamino)-camptothecin 20-acetate of Reference Example 5.21 and triethyl orthopropionate according to a manner analogous to those of Example 2.1 in two steps via compound (a).

(a) (9S)-9-acetoxy-2,9-diethyl-1-(3-methylbutyl)-1H,12H-pyrano[3",4":6',7']indolizino[1',2':6,5]pyrido[4,3,2-de]quinazoline-10,13 (9H,15H)-dione $^1$H NMR (270 MHz) δ (CDCl$_3$) 0.96 (t, J=7.4 Hz, 3H), 1.05 (d, J=6.6 Hz, 6H), 1.39 (t, J=7.3 Hz, 3H), 1.53–1.70 (m, 2H), 1.84 (m, 1H), 2.07–2.31 (m, 2H), 2.21 (s, 3H), 2.70 (q, J=7.3 Hz, 2H), 3.91 (m, 2H), 5.26 (s, 2H), 5.39 (d, J=17.2 Hz, 1H), 5.66 (d, J=17.2H, 1H), 7.10 (s, 1H), 7.13 (dd, J=1.3 and 7.3 Hz, 1H), 7.57 (dd, J=1.3 and 8.6 Hz, 1H), 7.66 (dd, J=7.3 and 8.6 Hz, 1H); MS (ES) m/z 529 (M$^+$+1).

(b) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13 (9H,15H)-dione $^1$H NMR (270 MHz) δ (DMSO-d$_6$) 0.87 (t, J=7.3 Hz, 3H), 1.01 (d, J=6.3 Hz, 6H), 1.25 (t, J=7.1 Hz, 3H), 1.69 (m, 1H), 1.78–1.87 (m, 2H), 2.74–2.79 (m, 2H), 3.97 (m, 2H), 5.41 (s, 4H), 1H), 6.52 (s, 1H), 6.99 (dd, J=1.0 and 7.6 Hz, 1H), 7.19 (s, 1H), 7.45 (dd, J=1.0 and 8.6 Hz, 1H), 7.63 (dd, J=7.6 and 8.6 Hz, 1H); MS (ES) m/z 487 (M$^+$+1).

Example 2.10

Preparation of (9S)-2,9-diethyl-9-hydroxy-1-(2-methylpropyl)-1H,12H-pyrano[3",4":6',7']indolizino[1',2':6,5]pyrido[4,3,2-de]quinazoline-10,13(9H, 15H)-dione This compound was prepared from (20S)-9-amino-7-(2-methylpropylamino)-camptothecin 20-acetate of Reference Example 5.12 and triethyl orthopropionate according to a manner analogous to those of Example 2.1 in two steps via compound (a).

(a) (9S)-9-acetoxy-2,9-diethyl-1-(2-methylpropyl)-1H,12H-pyrano[3",4":6',7']indolizino[1',2':6,5]pyrido[4,3,2-de]quinazoline-10,13 (9H,15H)-dione $^1$H NMR (270 MHz) δ (CDCl$_3$) 0.96 (t, J=7.4 Hz, 3H), 1.00 (m, 6H), 1.37 (t, J=7.4 Hz, 3H), 2.00 (m, 1H), 2.01–2.31 (m, 2H), 2.23 (s, 3H), 2.76 (q, J=7.4 Hz, 2H), 3.78 (m, 2H), 5.15 (m, 2H), 5.39 (d, J=17.0 Hz, 1H), 5.66 (d, J=17.0H, 1H), 7.10 (s, 1H), 7.17 (d, J=7.6 Hz, 1H), 7.61 (d, J=7.3 Hz, 1H), 7.69 (dd, J=7.3 and 7.6 Hz, 1H); MS (ES) m/z 515 (M$^+$+1).

(b) (9S)-2,9-diethyl-9-hydroxy-1-(2-methylpropyl)-1H,12H-pyrano[3",4":6',7']indolizino[1',2':6,5]-pyrido[,3,2-de]quinazoline-10,13 (9H,15H)-dione $^1$H NMR (400 MHz) δ (DMSO-d$_6$, 99.5° C.) 0.89 (t, J=7.6 Hz, 3H), 0.94 (d, J=6.4 Hz, 6H), 1.26 (t, J=7.0 Hz, 3H), 1.88 (m, 2H), 2.05 (m, 1H), 2.76 (q, J=7.0 Hz, 2H), 3.85 (d, J=7.6 Hz, 2H), 5.23 (s, 2H), 5.34 (d, J=16.6 Hz, 1H), 5.42 (d, J=16.6 Hz, 1H), 6.12 (brs, 1H), 7.01 (d, J=7.2 Hz, 1H), 7.22 (s, 1H), 7.48 (d, J=8.8 Hz, 1H), 7.64 (dd, J=7.2 and 8.8 Hz, 1H); MS (ES) m/z 473 (M$^+$+1).

Example 2.11

Preparation of (9S)-9-ethyl-1-heptyl-9-hydroxy-1H, 12H-pyrano[3",4":6',7']indolizino[1',2':6,5]pyrido[4, 3,2-de]quinazoline-10,13(9H,15H)-dione This compound was prepared from (20S)-9-amino-7-(heptylamino)camptothecin 20-acetate of Reference Example 5.10 according to a manner analogous to those of Example 2.1 in two steps via compound (a).

(a) (9S)-9-acetoxy-9-ethyl-1-heptyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.87 (t, J=6.6 Hz, 3H), 0.96 (t, J=7.6 Hz, 3H), 1.26–1.54 (m, 8H), 1.73–1.84 (m, 2H), 2.11–2.30 (m, 5H), 3.83 (t, J=7.1 Hz, 2H), 5.23 (s, 2H), 5.39 (d, J=17.2 Hz, 1H), 5.65 (d, J=.17.2 Hz, 1H), 7.09 (s, 1H), 7.17 (dd, J=1.5, 7.1 Hz, 1H), 7.40 (s, 1H), 7.60–7.71 (m, 2H); MS (ES) m/z 529 (M$^+$+1).

(b) (9S)-9-ethyl-1-heptyl-9-hydroxy-1H,12H-pyrano[3",4":6',7']indolizino[1',2':6,5]pyrido[4,3,2-de]quinazoline-10,13 (9H,15H)-dione $^1$H NMR (270 MHz) δ (CDCl$_3$) 0.83 (t, J=6.6 Hz, 3H), 1.03 (t, J=7.4 Hz, 3H), 1.26–1.52 (m, 8H), 1.59–1.93 (m, 4H), 3.78 (s, 1H), 3.82 (t, J=7.3 Hz, 2H), 5.22 (s, 2H), 5.28 (d, J=16.2 Hz, 1H), 5.72 (d, J=16.2 Hz, 1H), 7.13 (dd, J=2.0, 6.6 Hz, 1H), 7.38 (s, 1H), 7.56 (s, 1H), 7.59–7.69 (m, 2H); MS (ES) m/z 487 (M$^+$+1).

Example 2.12

Preparation of (9S)-9-ethyl-9-hydroxy-1-methyl-1H,12H-pyrano[3",4":6',7']indolizino[1',2':6,5]pyrido[4,3,2-de]quinazoline-10,13(9H,15H)-dione This compound was prepared from (20S)-9-amino-7-(methylamino)camptothecin 20-acetate of Reference Example 5.11 according to a manner analogous to those of Example 2.1 in two steps via compound (a).

(a) (9S)-9-acetoxy-9-ethyl-1-methyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.3 Hz, 3H), 2.14–2.28 (m, 5H), 3.71 (s, 3H), 5.38 (d, J=17.3 Hz, 1H), 5.44 (s, 2H), 5.65 (d, J=17.3 Hz, 1H), 7.08 (s, 1H), 7.15 (dd, J=1.7, 6.9 Hz, 1H), 7.37 (s, 1H), 7.61 (dd, J=1.7, 8.6 Hz, 1H), 7.67 (dd, J=6.9, 8.6 Hz, 1H); MS (ES) m/z 445 (M$^+$+1).

(b) (9S)-9-ethyl-9-hydroxy-1-methyl-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 1.81–1.88 (m, 2H), 3.74 (s, 3H), 5.41 (s, 2H), 5.54 (s, 2H), 6.46 (s, 1H), 6.97 (d, J=7.6 Hz, 1H), 7.18 (s, 1H), 7.45 (d, J=7.6 Hz, 1H), 7.62 (t, J=7.6 Hz, 1H), 7.75 (s, 1H); MS (ES) m/z 403 (M$^+$+1).

Example 2.13

Preparation of (9S)-9-ethyl-9-hydroxy-1-(2-methyl-propyl)-1H,12H-pyrano[3",4":6',7']indolizino[1',2':6,5]pyrido[4,3,2-de]quinazoline-10,13(9H,15H)-dione This compound was prepared from (20S)-9-amino-7-(2-methylpropylamino)-camptothecin 20-acetate of Reference Example 5.12 according to a manner analogous to those of Example 2.1 in two steps via compound (a).

(a) (9S)-9-acetoxy-9-ethyl-1-(2-methylpropyl)-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.6 Hz, 3H), 1.11 (d, J=6.6 Hz, 6H), 2.00–2.31 (m, 6H), 3.63 (d, J=7.6 Hz, 2H), 5.20 (s, 2H), 5.38 (d, J=17.2 Hz, 1H), 5.65 (d, J=17.2 Hz, 1H), 7.09 (s, 1H), 7.17 (dd, J=1.7, 6.9 Hz, 1H), 7.38 (s, 1H), 7.63 (dd, J=1.7, 8.6 Hz, 1H), 7.69 (dd, J=6.9, 8.6 Hz, 1H); MS (ES) m/z 487 (M$^+$+1).

(b) (9S)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 0.99 (d, J=6.6 Hz, 6H), 1.71–2.00 (m, 2H), 2.01–2.18 (m, 1H), 3.76 (d, J=7.3 Hz, 2H), 5.27 (s, 2H), 5.40 (s, 2H), 6.47 (s, 1H), 7.01 (dd, J=1.0, 7.6 Hz, 1H), 7.18 (s, 1H), 7.48 (dd, J=1.0, 8.6 Hz, 1H), 7.64 (dd, J=7.6, 8.6 Hz, 1H), 7.79 (s, 1H); MS (ES) m/z 445 (M$^+$+1).

Example 2.14

Preparation of (9S)-9-ethyl-1-hexyl-9-hydroxy-1H,12H-pyrano[3",4":6',7']indolizino[1',2':6,5]pyrido[4,3,2-de]quinazoline-10,13(9H,15H)-dione This compound was prepared from (20S)-9-amino-7-(hexylamino)camptothecin 20-acetate of Reference Example 5.13 according to a manner analogous to those of Example 2.1 in two steps via compound (a).

(a) (9S)-9-acetoxy-9-ethyl-1-hexyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.87–0.99 (m, 6H), 1.26–1.37 (m, 4H), 1.49–1.61 (m, 2H), 1.73–1.84 (m, 2H), 2.11–2.29 (m, 5H), 3.83 (t, J=7.3 Hz, 2H), 5.23 (s, 2H), 5.38 (d, J=17.2 Hz, 1H), 5.65 (d, J=17.2 Hz, 1H), 7.09 (s, 1H), 7.16 (dd, J=1.7, 7.1 Hz, 1H), 7.40 (s, 1H), 7.62 (dd, J=1.7, 8.6 Hz, 1H), 7.68 (dd, J=7.1, 8.6 Hz, 1H); MS (ES) m/z 515 (M$^+$+1).

(b) (9S)-9-ethyl-1-hexyl-9-hydroxy-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.84–0.90 (m, 6H), 1.23–1.45 (m, 6H), 1.68–1.96 (m, 4H), 3.84–3.96 (m, 2H), 5.29 (s, 2H), 5.40 (s, 2H), 6.46 (s, 1H), 6.99 (dd, J=1.0, 7.6 Hz, 1H), 7.18 (s, 1H), 7.47 (dd, J=1.0, 8.6 Hz, 1H), 7.64 (dd, J=7.6, 8.6 Hz, 1H), 7.86 (s, 1H); MS (ES) m/z 473 (M$^+$+1).

Example 2.15

Preparation of (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione This compound was prepared from (20S)-9-amino-7-(pentylamino)camptothecin 20-acetate of Reference Example 5.14 according to a manner analogous to those of Example 2.1 in two steps via compound (a).

(a) (9S)-9-acetoxy-9-ethyl-1-pentyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.91–0.99 (m, 6H), 1.26–1.58 (m, 4H), 1.74–1.82 (m, 2H), 2.09–2.31 (m, 5H), 3.83 (t, J=7.3 Hz, 2H), 5.23 (s, 2H), 5.39 (d, J=17.2 Hz, 1H), 5.65 (d, J=17.2 Hz, 1H), 7.09 (s, 1H), 7.17 (dd, J=1.5, 6.9 Hz, 1H), 7.40 (s, 1H), 7.62 (dd, J=1.5, 8.6 Hz, 1H), 7.68 (dd, J=6.9, 8.6 Hz, 1H);

(b) (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.85–0.92 (m, 6H), 1.35–1.38 (m, 4H), 1.75–1.93 (m, 4H), 3.89–3.94 (m, 2H), 5.29 (s, 2H), 5.40 (s, 2H), 6.46 (s, 1H), 6.99 (dd, J=1.0, 7.4 Hz, 1H), 7.18 (s, 1H), 7.47 (dd, J=1.0, 8.6 Hz, 1H), 7.62 (dd, J=7.4, 8.6 Hz, 1H), 7.86 (s, 1H); MS (ES) m/z 459 (M$^+$+1).

Example 2.16

Preparation of (9S)-1,9-diethyl-9-hydroxy-1H,12H-pyrano[3",4":6',7']indolizino[1',2':6,5]pyrido[4,3,2-de]quinazoline-10,13(9H,15H)-dione This compound was prepared from (20S)-9-amino-7-(ethylamino)camptothecin 20-acetate of Reference Example 5.15 according to a manner analogous to those of Example 2.1 in two steps via compound (a).

(a) (9S)-9-acetoxy-1,9-diethyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.6 Hz, 3H), 1.49 (t, J=7.3 Hz, 3H), 2.11–2.29 (m, 5H), 3.92 (q, J=7.3 Hz, 2H), 5.26 (s, 2H), 5.38 (d, J=17.3 Hz, 1H), 5.66 (d, J=17.3 Hz, 1H), 7.10 (s, 1H), 7.17 (dd, J=1.3, 6.9 Hz, 1H), 7.43 (s, 1H), 7.62 (dd, J=1.3, 8.6 Hz, 1H), 7.68 (dd, J=6.9, 8.6 Hz, 1H); MS (ES) m/z 459 (M$^+$+1).

(b) (9S)-1,9-diethyl-9-hydroxy-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 1.39 (t, J=7.3 Hz, 3H), 1.81–1.90 (m, 2H), 3.94–4.02 (m, 2H), 5.33 (s, 2H), 5.41 (s, 2H), 6.46 (s, 1H), 6.99 (d, J=7.6 Hz, 1H), 7.19 (s, 1H), 7.47 (d, J=7.6 Hz, 1H), 7.63 (t, J=7.6 Hz, 1H), 7.82 (s, 1H); MS (ES) m/z 417 (M$^+$+1).

Example 2.17

Preparation of (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-10,13(9H,15H)-dione This compound was prepared from (20S)-9-amino-7-[2-(4-methoxyphenyl)ethylamino]camptothecin 20-acetate of Reference Example 5.16 according to a manner analogous to those of Example 2.1 in two steps via compound (a).

(a) (9S)-9-acetoxy-9-ethyl-1-[2-(4-methoxyphenyl)ethyl]-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.97 (t, J=7.6 Hz, 3H), 2.12–2.30 (m, 5H), 3.01 (t, J=6.3 Hz, 2H), 3.78 (s, 3H), 4.04 (t, J=6.3 Hz, 2H), 5.29 (s, 2H), 5.40 (d, J=17.2 Hz, 1H), 5.67 (d, J=17.2 Hz, 1H), 6.82 (m, 2H), 6.93 (s, 1H), 7.05–7.13 (m, 4H), 7.63 (dd, J=1.7, 8.6 Hz, 1H), 7.68 (dd, J=6.9, 8.6 Hz, 1H); MS (ES) m/z 565 (M$^+$+1).

(b) (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.88 (t, J=7.3 Hz, 3H), 1.77–1.95 (m, 2H), 3.04 (t, J=7.3 Hz, 2H), 3.73 (s, 3H), 4.14 (t, J=7.3 Hz, 2H), 5.42 (s, 4H), 6.47 (s, 1H), 6.89 (d, J=8.6 Hz, 2H), 6.97 (dd, J=1.0, 7.6 Hz, 1H), 7.21 (s, 1H), 7.26 (d, J=8.6 Hz, 2H), 7.49 (dd, J=1.0, 8.6 Hz, 1H), 7.57 (s, 1H), 7.63 (dd, J=7.6, 8.6 Hz, 1H); MS (ES) m/z 523 (M$^+$+1).

Example 2.18

Preparation of (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-10,13(9H,15H)-dione This compound was prepared from (20S)-9-amino-7-[2-(4-chlorophenyl)ethylamino]camptothecin 20-acetate of Reference Example 5.17 according to a manner analogous to those of Example 2.1 in two steps via compound (a).

(a) (9S)-9-acetoxy-1-[2-(4-chlorophenyl)ethyl]-9-ethyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.97 (t, J=7.6 Hz, 3H), 2.10–2.32 (m, 5H), 3.05 (t, J=6.6 Hz, 2H), 4.07 (t, J=6.6 Hz, 2H), 5.28 (s, 2H), 5.39 (d, J=17.2 Hz, 1H), 5.66 (d, J=17.2 Hz, 1H), 6.93 (s, 1H), 7.09–7.15 (m, 4H), 7.31 (d, J=8.6 Hz, 2H), 7.64 (dd, J=2.0, 6.6 Hz, 1H), 7.69 (dd, J=6.6, 8.3 Hz, 1H); MS (ES) m/z 569 (M$^+$+1).

(b) (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 1.77–1.95 (m, 2H), 3.12 (t, J=7.4 Hz, 2H), 4.19 (t, J=7.4 Hz, 2H), 5.42 (s, 4H), 6.49 (s, 1H), 6.98 (dd, J=1.0, 7.4 Hz, 1H), 7.21 (s, 1H), 7.36–7.43 (m, 4H), 7.50 (dd, J=1.0, 8.6 Hz, 1H), 7.56 (s, 1H), 7.64 (dd, J=7.4, 8.6 Hz, 1H); MS (ES) m/z 527 (M$^+$+1).

Example 2.19

Preparation of (9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-10,13(9H,15H)-dione This compound was prepared from (20S)-9-amino-7-[2-(4-fluorophenyl)-ethylamino]camptothecin 20-acetate of Reference Example 5.18 according to a manner analogous to those of Example 2.1 in two steps via compound (a).

(a) (9S)-9-acetoxy-9-ethyl-1-[2-(4-fluorophenyl) ethyl]-1H,12H-pyrano[3",4":6',7']indolizino[1',2':6, 5]pyrido[4,3,2-de]quinazoline-10,13(9H,15H)-dione $^1$H NMR (270 MHz) δ (CDCl$_3$) 0.97 (t, J=7.6 Hz, 3H), 2.07–2.35 (m, 5H), 3.05 (t, J=6.6 Hz, 2H), 4.06 (t, J=6.6 Hz, 2H), 5.29 (s, 2H), 5.39 (d, J=17.2 Hz, 1H), 5.66 (d, J=17.2 Hz, 1H), 6.92 (s, 1H), 6.97–7.17 (m, 6H), 7.64 (dd, J=2.0, 8.2 Hz, 1H), 7.69 (dd, J=6.6, 8.2 Hz, 1H); MS (ES) m/z 553 (M$^+$+1).

(b) (9S)-9-ethyl-1-[2-(4-fluorophenyl)ethyl]-9-hydroxy-1H,12H-pyrano[3",4":6',7']indolizino[1',2':6, 5]pyrido[4,3,2-de]quinazoline-10,13(9H,15H)-dione $^1$H NMR (270 MHz) δ (CDCl$_3$) 1.03 (t, J=7.3 Hz, 3H), 1.81–1.96 (m, 2H), 3.07 (t, J=6.5 Hz, 2H), 3.93 (br, 1H), 4.05 (t, J=6.5 Hz, 2H), 5.26 (s, 2H), 5.28 (d, J=16.3 Hz, 1H), 5.72 (d, J=16.3 Hz, 1H), 6.89 (s, 1H), 7.00–7.19 (m, 5H), 7.54 (s, 1H), 7.60–7.68 (m, 2H); MS (ES) m/z 511 (M$^+$+1).

Example 2.20

Preparation of (9S)-9-ethyl-1-[2-(4-fluorophenyl) ethyl]-9-hydroxy-2-methyl-1H,12H-pyrano[3",4":6', 7']indolizino[1',2':6,5]pyrido[4,3,2-de]quinazoline-10,13(9H,15H)-dione This compound was prepared from (20S)-9-amino-7-[2-(4-fluorophenyl)-ethylamino]camptothecin 20-acetate of Reference Example 5.18 and trimethyl orthoacetate according to a manner analogous to those of Example 2.1 in two steps via compound (a).

(a) (9S)-9-acetoxy-9-ethyl-1-[2-(4-fluorophenyl) ethyl]-2-methyl-1H,12H-pyrano[3",4":6',7']indolizino[1',2':6,5]pyrido[4,3,2-de]quinazoline-10,13 (9H,15H)-dione $^1$H NMR (270 MHz) δ (CDCl$_3$) 0.97 (t, J=7.6 Hz, 3H), 2.10–2.32 (m, 8H), 3.00 (t, J=6.9 Hz, 2H), 4.17 (t, J=6.9 Hz, 2H), 5.31 (s, 2H), 5.40 (d, J=17.2 Hz, 1H), 5.66 (d, J=17.2 Hz, 1H), 6.97–7.18, (m, 6H), 7.63 (dd, J=1.3, 8.6 Hz, 1H), 7.70 (dd, J=7.3, 8.6 Hz, 1H); MS (ES) m/z 567 (M$^+$+1).

(b) (9S)-9-ethyl-1-[2-(4-fluorophenyl)ethyl]-9-hydroxy-2-methyl-1H,12H-pyrano[3",4":6',7']indolizino[1',2':6,5]pyrido[4,3,2-de]quinazoline-10,13 (9H,15H)-dione $^1$H NMR (270 MHz) δ (CDCl$_3$) 1.04 (t, J=7.4 Hz, 3H), 1.78–2.00 (m, 2H), 2.18 (s, 3H), 3.02 (t, J=7.0 Hz, 2H), 3.74 (s, 1H), 4.18 (t, J=7.0 Hz, 2H), 5.30 (d, J=16.5 Hz, 1H), 5.32 (s, 2H), 5.74 (d, J=16.5 Hz, 1H), 6.96–7.20 (m, 5H), 7.57 (s, 1H), 7.63–7.73 (m, 2H); MS (ES) m/z 525 (M$^+$+1).

Example 2.21

Preparation of (9S)-9-ethyl-9-hydroxy-1-(1-methylethyl)-1H,12H-pyrano[3",4":6',7']indolizino[1',2':6, 5]pyrido[4,3,2-de]quinazoline-10,13(9H,15H)-dione This compound was prepared from (20S)-9-amino-7-(1-methylethylamino)camptothecin 20-acetate of Reference Example 5.19 according to a manner analogous to those of Example 2.1 in two steps via compound (a).

(a) (9S)-9-acetoxy-9-ethyl-1-(1-methylethyl)-1H, 12H-pyrano[3",4":6',7']indolizino[1',2':6,5]pyrido[4, 3,2-de]quinazoline-10,13(9H,15H)-dione $^1$H NMR (270 MHz) δ (CDCl$_3$) 0.96 (t, J=7.6 Hz, 3H), 1.59–1.63 (m, 6H), 2.09–2.31 (m, 5H), 4.40–4.44 (m, 1H), 5.27 (s, 2H), 5.39 (d, J=17.2 Hz, 1H), 5.66 (d, J=17.2 Hz, 1H), 7.10 (s, 1H), 7.17 (dd, J=1.3, 6.9 Hz, 1H), 7.59–7.71 (m, 3H); MS (ES) m/z 473 (M$^+$+1).

(b) (9S)-9-ethyl-9-hydroxy-1-(1-methylethyl)-1H, 12H-pyrano[3",4":6',7']indolizino[1',2':6,5]pyrido[4, 3,2-de]quinazoline-10,13(9H,15H)-dione $^1$H NMR (270 MHz) δ (DMSO-d$_6$) 0.87 (t, J=7.3 Hz, 3H), 1.54 (d, J=6.6 Hz, 6H), 1.81–1.90 (m, 2H), 4.34–4.53 (m, 1H), 5.37 (s, 2H), 5.41 (s, 2H), 6.48 (s, 1H), 7.00 (dd, J=1.0, 7.6 Hz, 1H), 7.19 (s, 1H), 7.47 (dd, J=1.0, 8.3 Hz, 1H), 7.64 (dd, J=7.6, 8.3 Hz, 1H), 7.99 (s, 1H); MS (ES) m/z 431 (M$^+$+1).

Example 2.22

Preparation of (9S)-1-(3,3-dimethylbutyl)-9-ethyl-9-hydroxy-1H,12H-pyrano[3",4":6',7']indolizino[1',2': 6,5]pyrido[4,3,2-de]quinazoline-10,13(9H,15H)-dione This compound was prepared from (20S)-9-amino-7-(3, 3-dimethylbutylamino)camptothecin 20-acetate of Reference Example 5.20 according to a manner analogous to those of Example 2.1 in two steps via compound (a).

(a) (9S)-9-acetoxy-1-(3,3-dimethylbutyl)-9-ethyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.6 Hz, 3H), 1.11 (s, 9H), 1.64–1.73 (m, 2H), 2.09 (m, 5H), 3.83 (m, 2H), 5.28 (s, 2H), 5.38 (d, J=17.2 Hz, 1H), 5.65 (d, J=17.2 Hz, 1H), 7.09 (s, 1H), 7.15 (d, J=7.3 Hz, 1H), 7.38 (s, 1H), 7.60–7.70 (m, 2H); MS (ES) m/z 515 (M$^+$+1).

(b) (9S)-1-(3,3-dimethylbutyl)-9-ethyl-9-hydroxy-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 1.02 (t, J=7.3 Hz, 3H), 1.11 (s, 9H), 1.68–1.80 (m, 2H), 1.81–1.96 (m, 2H), 3.73–3.92 (m, 3H), 5.24 (s, 2H), 5.26 (d, J=16.3 Hz, 1H), 5.70 (d, J=16.3 Hz, 1H), 7.10 (dd, J=1.8, 6.9 Hz, 1H), 7.34 (s, 1H), 7.50 (s, 1H), 7.59 (dd, J=1.8, 8.6 Hz, 1H), 7.64 (dd, J=6.9, 8.6 Hz, 1H); MS (ES) m/z 473 (M$^+$+1).

Example 2.23

Preparation of (9S)-9-ethyl-9-hydroxy-2-methoxy-1-(3-methylbutyl)-1H,12H-pyrano[3",4":6',7']indolizino[1',2':6,5]pyrido[4,3,2-de]quinazoline-10,13 (9H,15H)-dione This compound was prepared from (20S)-9-amino-7-(3-methylbutylamino)camptothecin 20-acetate of Reference Example 5.21 and tetramethyl orthocarbonate according to a manner analogous to those of Example 2.1 in two steps via compound (a).

(a) (9S)-9-acetoxy-9-ethyl-2-methoxy-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.4 Hz, 3H), 1.03 (d, J=6.3 Hz, 6H), 1.57 (m, 2H), 1.72–1.84 (m, 1H), 2.07–2.34 (m, 5H), 3.99–4.12 (m, 5H), 5.31 (s, 2H), 5.39 (d, J=17.2 Hz, 1H), 5.66 (d, J=17.2 Hz, 1H), 7.03 (dd, J=1.3, 8.6 Hz, 1H), 7.11 (s, 1H), 7.52 (dd, J=1.3, 8.6 Hz, 1H), 7.64 (dd, J=7.6, 8.6 Hz, 1H); MS (ES) m/z 531 (M$^+$+1).

(b) (9S)-9-ethyl-9-hydroxy-2-methoxy-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 0.99 (d, J=6.3 Hz, 6H), 1.54–1.91 (m, 5H), 3.95–4.07 (m, 5H), 5.41 (s, 4H), 6.50 (s, 1H), 6.92 (dd, J=1.0, 7.6 Hz, 1H), 7.21 (s, 1H), 7.42 (dd, J=1.0, 8.6 Hz, 1H), 7.62 (dd, J=7.6, 8.6 Hz, 1H); MS (ES) m/z 489 (M$^+$+1).

Example 2.24

Preparation of (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione This compound was prepared from (20S)-9-amino-7-(3-methylbutylamino)camptothecin 20-acetate of Reference Example 5.21 and triethyl orthopropionate according to a manner analogous to those of Example 2.1 in two steps via compound (a).

(a) (9S)-9-acetoxy-2,9-diethyl-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.6 Hz, 3H), 1.05 (d, J=6.6 Hz, 6H), 1.40 (t, J=7.4 Hz, 3H), 1.59–1.65 (m, 2H), 1.85–1.89 (m, 1H), 2.09–2.32 (m, 5H), 2.71 (q, J=7.4 Hz, 2H), 3.92–3.98 (m, 2H), 5.28 (s, 2H), 5.39 (d, J=17.2 Hz, 1H), 5.66 (d, J=17.2 Hz, 1H), 7.10 (s, 1H), 7.14 (dd, J=1.3, 7.3 Hz, 1H), 7.58 (dd, J=1.3, 8.3 Hz, 1H), 7.67 (dd, J=7.3, 8.3 Hz, 1H); MS (ES) m/z 529 (M$^+$+1).

(b) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.1 Hz, 3H), 1.01 (d, J=6.6 Hz, 6H), 1.25 (t, J=7.1 Hz, 3H), 1.67–1.87 (m, 5H), 2.72–2.75 (m, 2H), 3.86–4.00 (m, 2H), 5.37 (s, 2H), 5.41 (s, 2H), 6.49 (s, 1H), 6.97 (d, J=7.9 Hz, 1H), 7.18 (s, 1H), 7.45 (d, J=7.9 Hz, 1H), 7.63 (d, J=7.9 Hz, 1H); MS (ES) m/z 487 (M$^+$+1).

Example 2.25

Preparation of (9RS)-9-ethyl-9-hydroxy-4-methyl-1-pentyl-1H,12H-pyrano[3",4":6',7']indolizino[1',2':6,5]pyrido[4,3,2-de]quinazoline-10,13(9H,15H)-dione This compound was prepared from (20RS)-9-amino-10-methyl-7-(pentylamino)-camptothecin 20-acetate of Reference Example 5.22 according to a manner analogous to those of Example 2.1 in two steps via compound (a).

(a) (9RS)-9-acetoxy-9-ethyl-4-methyl-1-pentyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.85–1.00 (m, 6H), 1.30–1.56 (m, 4H), 1.68–1.87 (m, 2H), 2.02–2.34 (m, 5H), 2.45 (s, 3H), 3.82 (t, J=7.3 Hz, 2H), 5.21 (s, 2H), 5.38 (d, J=17.2 Hz, 1H), 5.65 (d, J=17.2 Hz, 1H), 7.07 (s, 1H), 7.42 (s, 1H), 7.56 (d, J=8.7 Hz, 1H), 7.60 (d, J=8.7 Hz, 1H); MS (ES) m/z 515 (M$^+$+1).

(b) (9RS)-9-ethyl-9-hydroxy-4-methyl-1-pentyl-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.86–0.95 (m, 6H), 1.29–1.43 (m, 4H), 1.65–1.93 (m, 4H), 2.28 (s, 3H), 3.80–3.95 (m, 2H), 5.27 (s, 2H), 5.40 (s, 2H), 6.47 (s, 1H), 7.15 (s, 1H), 7.41 (d, J=8.7 Hz, 1H), 7.56 (d, J=8.7 Hz, 1H), 7.82 (s, 1H); MS (ES) m/z 473 (M$^+$+1).

Example 2.26

Preparation of (9S)-9-ethyl-9-hydroxy-1-(2-hydroxyethyl)-1H,12H-pyrano[3",4":6',7']indolizino[1',2':6,5]pyrido[4,3,2-de]quinazoline-10,13(9H,15H)-dione This compound was prepared from (20S)-9-amino-7-(2-hydroxyethylamino)camptothecin 20-acetate of Reference Example 5.23 according to a manner analogous to those of Example 2.1 in two steps via compound (a).

(a) (9S)-9-acetoxy-9-ethyl-1-(2-hydroxyethyl)-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.97 (t, J=7.6 Hz, 3H), 2.02–2.30 (m, 6H), 3.94–4.05 (m, 4H), 5.21 (s, 2H), 5.35 (d, J=17.2 Hz, 1H), 5.63 (d, J=17.2 Hz, 1H), 7.02–7.09 (m, 2H), 7.44 (s, 1H), 7.50–7.65 (m, 2H); MS (ES) m/z 475 (M$^+$+1).

(b) (9S)-9-ethyl-9-hydroxy-1-(2-hydroxyethyl)-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.86 (t, J=7.3 Hz, 3H), 1.74–1.92 (m, 2H), 3.70–3.81 (m, 2H), 3.97–4.06 (m, 2H), 5.24 (t, J=5.3 Hz, 1H), 5.32 (s, 2H), 5.41 (s, 2H), 6.49 (s, 1H), 7.01 (dd, J=1.0, 7.4 Hz, 1H), 7.19 (s, 1H), 7.48 (dd, J=1.0, 8.6 Hz, 1H), 7.64 (dd, J=7.4, 8.6 Hz, 1H), 7.73 (s, 1H); MS (ES) m/z 433 (M$^+$+1).

Example 2.27

Preparation of (9S)-9-ethyl-9-hydroxy-1-(2-hydroxyethyl)-2-methyl-1H,12H-pyrano[3",4":6',7']indolizino[1',2':6,5]pyrido[4,3,2-de]quinazoline-10,13(9H,15H)-dione This compound was prepared from (20S)-9-amino-7-(2-hydroxyethylamino)camptothecin 20-acetate of Reference Example 5.23 and trimethyl orthoacetate according to a manner analogous to those of Example 2.1 in two steps via compound (a).

(a) (9S)-9-acetoxy-9-ethyl-1-(2-hydroxyethyl)-2-methyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.6 Hz, 3H), 2.06–2.30 (m, 5H), 2.54 (s, 3H), 3.92–4.01 (m, 2H), 4.12–4.21 (m, 2H), 5.23–5.31 (m, 3H), 5.36 (d, J=17.0 Hz, 1H), 5.63 (d, J=17.0 Hz, 1H), 7.07 (dd, J=1.3, 7.3 Hz, 1H), 7.10 (s, 1H), 7.54–7.67 (m, 2H); MS (ES) m/z 489 (M$^+$+1).

(b) (9S)-9-ethyl-9-hydroxy-1-(2-hydroxyethyl)-2-methyl-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 1.74–1.94 (m, 2H), 2.80 (s, 3H), 3.68–3.82 (m, 2H), 4.04–4.18 (m, 2H), 5.25 (t, J=5.4 Hz, 1H), 5.33 (s, 2H), 5.41 (s, 2H), 6.49 (s, 1H), 6.96 (dd, J=1.0, 7.6 Hz, 1H), 7.19 (s, 1H), 7.45 (dd, J=1.0, 8.6 Hz, 1H), 7.63 (dd, J=7.6, 8.6 Hz, 1H); MS (ES) m/z 447 (M$^+$+1).

Example 2.28

Preparation of (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)-dione This compound was prepared from (20S)-9-amino-7-(pentylamino)camptothecin 20-acetate of Reference Example 5.14 and trimethyl orthoacetate according to a manner analogous to those of Example 2.1 in two steps via compound (a).

(a) (9S)-9-acetoxy-9-ethyl-2-methyl-1-pentyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.94 (t, J=6.9 Hz, 3H), 0.97 (t, J=7.3 Hz, 3H), 1.30–1.56 (m, 4H), 1.65–1.89 (m, 2H), 2.05–2.35 (m, 2H), 2.21 (s, 3H), 2.49 (s, 3H), 3.79–4.01 (m, 2H), 5.24 (brs, 2H), 5.39 and 5.66 (q, J=17.2 Hz, 1H×2), 7.04–7.12 (m, 1H), 7.08 (s, 1H), 7.52–7.71 (m, 2H); MS (ES) m/z 515 (M$^+$+1).

(b) (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 0.91 (t, J=7.3 Hz, 3H), 1.30–1.60 (m, 4H), 1.66–1.94 (m, 4H), 2.45 (d, J=2.6 Hz, 3H), 3.93 (br, 2H), 5.23–5.44 (m, 2H), 5.41 (brs, 2H), 6.50 (brs, 1H), 6.89–7.00 (m, 1H), 7.19 (d, J=2.3 Hz, 1H), 7.38–7.49 (m, 1H), 7.62 (dt, J=3.6 and 7.9 Hz, 1H); MS (FAB) m/z 473 (M$^+$+1).

Example 2.29

Preparation of (9S)-2,9-diethyl-9-hydroxy-1-pentyl-1H,12H-pyrano[3",4":6',7']indolizino[1',2':6,5]pyrido[4,3,2-de]quinazoline-10,13(9H,15H)-dione This compound was prepared from (20S)-9-amino-7-(pentylamino)camptothecin 20-acetate of Reference Example 5.14 and triethyl orthopropionate according to a manner analogous to those of Example 2.1 in two steps via compound (a).

(a) (9S)-9-acetoxy-2,9-diethyl-1-pentyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.93 (t, J=6.9 Hz, 3H), 0.96 (t, J=7.6 Hz, 3H), 1.23–1.56 (m, 4H), 1.38 (t, J=7.3 Hz, 3H), 1.65–1.93 (m, 2H), 2.05–2.38 (m, 2H), 2.21 (s, 3H), 2.71 (q, J=7.3 Hz, 2H), 3.81–3.98 (m, 2H), 5.24 (brs, 2H), 5.39 and 5.66 (q, J=17.2 Hz, 1H×2), 7.10 (s, 1H), 7.13 (dd, J=1.0 and 7.4 Hz, 1H), 7.52–7.61 (m, 1H), 7.67 (dd, J=7.4 and 8.4 Hz, 1H); MS (ES) m/z 529 (M$^+$+1).

(b) (9S)-2,9-diethyl-9-hydroxy-1-pentyl-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.88 (t, J=7.3 Hz, 3H), 0.91 (t, J=6.9 Hz, 3H), 1.19–1.29 (m, 3H), 1.31–1.48 (m, 4H), 1.67–1.94 (m, 4H), 2.68–2.82 (m, 2H), 3.92 (br, 2H), 5.24–5.42 (m, 2H), 5.42 (brs, 2H), 6.50 (brs, 1H), 6.92–7.01 (m, 1H), 7.19 (d, J=1.3 Hz, 1H), 7.41–7.49 (m, 1H), 7.58–7.69 (m, 1H); MS (FAB) m/z 487 (M$^+$+1).

Example 2.30

Preparation of (9S)-9-ethyl-9-hydroxy-1-pentyl-2-propyl-1H,12H-pyrano[3",4":6',7']indolizino[1',2':6,5]pyrido[4,3,2-de]quinazoline-10,13(9H,15H)-dione This compound was prepared from (20S)-9-amino-7-(pentylamino)camptothecin 20-acetate of Reference Example 5.14 and trimethyl orthobutyrate according to a manner analogous to those of Example 2.1 in two steps via compound (a).

(a) (9S)-9-acetoxy-9-ethyl-1-pentyl-2-propyl-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.89–1.01 (m, 6H), 1.11 (t, J=7.4 Hz, 3H), 1.28–1.57 (m, 4H), 1.65–1.80 (m, 2H), 1.86 (hext. J=7.4 Hz, 2H), 2.03–2.36 (m, 2H), 2.21 (s, 3H), 2.64 (t, J=7.4 Hz, 2H), 3.96 (t, I=7.9 Hz, 2H), 5.24 (brs, 2H), 5.39 and 5.66 (q, J=17.2 Hz, 1H×2), 7.10 (s, 1H), 7.12 (dd, J=1.2 and 7.4 Hz, 1H), 7.52–7.61 (m, 1H), 7.66 (t, J=7.4 Hz, 1H); MS (ES) m/z 543 (M$^+$+1).

(b) (9S)-9-ethyl-9-hydroxy-1-pentyl-2-propyl-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.88 (t, J=7.4 Hz, 3H), 0.91 (t, J=7.4 Hz, 3H), 1.04 (t, J=7.4 Hz, 3H), 1.31–1.49 (m, 4H), 1.68–1.94 (m, 6H), 2.65–2.76 (m, 2H), 3.88–4.02 (m, 2H), 5.35 (brs, 2H), 5.42 (s, 2H), 6.51 (br, 1H), 6.97–7.05 (m, 1H), 7.23 (d, J=4.3 Hz, 1H), 7.48 (d, J=8.4 Hz, 1H), 7.66 (dt, J=1.6 and 8.4 Hz, 11); MS (FAB) m/z 501 (M$^+$+1).

Example 3.1

Preparation of (9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione The preparation method comprises of the following two steps via compound (a).

(a) (9S)-9-acetoxy-2-acetoxymethyl-9-ethyl-1-pentyl-1H,12H-pyrano[3",4":6',7']indolizino[1',2':6,5]pyrido[4,3,2-de]quinazoline-10,13(9H,15H)-dione To a solution of (20S)-9-amino-7-(pentylamino)camptothecin 20-acetate hydrochloride (1.61 g mg, 3.07 mmol) of Reference Example 5.14 in dry dichloromethane (120 ml) cooled in an ice-bath were added acetoxyacetyl chloride (4.3 ml) and diisopropylethylamine (1.07 ml) successively. After the addition, the mixture was warmed to room temperature and stirred for overnight. Water (50 ml) was added and the mixture was extracted with dichloromethane (100 ml). The dichloromethane layer was washed with brine, dried over $MgSO_4$ and concentrated under reduced pressure. The obtaining residue was purified by column chromatography (eluent: ethyl acetate/hexane=8/1) to give pure product (1.72, 98%).

$^1$H NMR (400 MHz) δ (CDCl$_3$) 0.91 (t, J=7.3 Hz, 3H), 0.97 (t, J=7.5 Hz, 3H), 1.31–1.48 (m, 4H), 1.70–1.82 (m, 2H), 2.08–2.30 (m, 2H), 2.22 (s, 3H), 2.25 (s, 3H), 3.86 (t, J=7.9 Hz, 2H), 5.04 (s, 2H), 5.26 (s, 2H), 5.39 (d, J=17.1 Hz, 1H), 5.66 (d, J=17.1 Hz, 1H), 7.13 (s, 1H), 7.19 (dd, J=2.0 and 6.6 Hz, 1H), 7.63–7.73 (m, 2H); MS (ES) m/z 573(M$^+$+1).

(b) (9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione To a solution of (9S)-9-acetoxy-2-acetoxymethyl-9-ethyl-1-pentyl-1H,12H-pyrano[3",4":6'7']indolizino[1'2':6,5]pyrido[4,3,2-de]quinazoline-10,13(9H,15H)-dione (34 mg, 0.059 mmol) in methanol (3 ml) cooled in an ice-bath was added anhydrous hydrazine (100 μl) and the mixture was stirred for 2 hr. at room temperature. Aqueous 1 N hydrochloric acid solution (5 ml) was added dropwise to acidify the reaction mixture, and the mixture was stirred for 1 hr. at room temperature. The mixture was extracted with dichloromethane (50 ml) and the dichloromethane layer was washed with brine, dried over MgSO$_4$ and evaporated. The residue was purified by column chromatography (dichloromethane/methanol=25/1) to give pure product (19 mg, 65%).

$^1$H NMR (400 MHz) δ (DMSO-d$_6$) 0.87 (t, J=7.6 Hz, 3H), 0.90 (t, J=6.9 Hz, 3H), 1.32–1.45 (m, 4H), 1.74–1.90 (m, 4H), 4.04 (m, 2H), 4.43 (d, J=5.6 Hz, 2H), 5.36 (s, 2H), 5.41 (s, 2H), 5.79 (t, J=5.6 Hz, 1H), 6.50 (s, 1H), 7.03 (dd, J=1.0 and 7.3 Hz, 1H), 7.20 (s, 1H), 7.50 (dd, J=1.0 and 8.6 Hz, 1H), 7.66 (dd, J=7.3 and 8.6 Hz, 1H); MS (ES) m/z 489(M$^+$+1).

Example 3.2

Preparation of (9S)-9-ethyl-9-hydroxy-2-hydroxymethyl-1-(2-methylpropyl)-1H,12H-pyrano[3",4":6',7']indolizino[1',2':6,5]pyrido[4,3,2-de]quinazoline-10,13 (9H,15H)-dione This compound was prepared from (20S)-9-amino-7-(2-methylpropylamino)camptothecin 20-acetate of Reference Example 5.12 according to a manner analogous to those of Example 3.1 in two steps via compound (a).

(a) (9S)-9-acetoxy-2-acetoxymethyl-9-ethyl-1-(2-methylpropyl)-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.4 Hz, 3H), 1.05 (d, J=6.3 Hz, 6H), 2.01 (m, 1H), 2.06–2.31 (m, 2H), 2.21 (s, 3H), 2.24 (s, 3H), 3.70 (m, 2H), 4.66 (s, 2H), 5.08–5.18 (m, 2H), 5.39 (d, J=17.2 Hz, 1H), 5.66 (d, J=17.2H, 1H), 7.14 (s, 1H), 7.22 (dd, J=2.1 and 6.4 Hz, 1H), 7.67–7.75 (m, 2H); MS (ES) m/z 559 (M$^+$+1).

(b) (9S)-9-ethyl-9-hydroxy-2-hydroxymethyl-1-(2-methylpropyl)-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.1 Hz, 3H), 0.94 (m, 6H), 1.84 (m, 2H), 2.07 (m, 1H), 4.40 (m, 2H), 5.41 (m, 4H), 5.75 (t, J=5.9 Hz, 1H), 6.49 (s, 1H), 7.07 (d, J=7.9 Hz, 1H), 7.21 (s, 1H), 7.54 (d, J=8.6 Hz, 1H), 7.69 (dd, J=7.9 and 8.6 Hz, 1H); MS (ES) m/z 475 (M$^+$+1).

Example 3.3

Preparation of (9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione This compound was prepared from (20S)-9-amino-7-(3-methylbutylamino)camptothecin 20-acetate of Reference Example 5.21 according to a manner analogous to those of Example 3.1 in two steps via compound (a).

(a) (9S)-9-acetoxy-2-acetoxymethyl-9-ethyl-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.97 (t, J=7.6 Hz, 3H), 1.04 (d, J=6.6 Hz, 6H), 1.68 (m, 2H), 1.86 (m, 1H), 2.07–2.31 (m, 2H), 2.22 (s, 3H), 2.24 (s, 3H), 3.84 (t, J=8.4 Hz, 2H), 5.03 (s, 2H), 5.28 (m, 2H), 5.39 (d, J=17.2 Hz, 1H), 5.66 (d, J=17.2H, 1H), 7.13 (s, 1H), 7.18 (dd, J=1.5 and 6.4 Hz, 1H), 7.64–7.72 (m, 2H); MS (ES).m/z 573 (M$^+$+1).

(b) (9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 1.00 (d, J=5.9 Hz, 6H), 1.73–1.87 (m, 5H), 4.09 (m, 2H), 4.42 (d, J=5.6 Hz, 2H), 5.41 (s, 4H), 5.81 (t, J=5.6 Hz, 1H), 6.49 (s, 1H), 7.02 (dd, J=1.0 and 7.6 Hz, 1H), 7.20 (s, 1H), 7.50 (dd, J=1.0 and 8.6 Hz, 1H), 7.66 (dd, J=7.6 and 8.6 Hz, 1H); MS (ES) m/z 489 (M$^+$+1).

Example 3.4

Preparation of (9S)-2-chloromethyl-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione This compound was prepared from (20S)-9-amino-7-(3-methylbutylamino)camptothecin 20-acetate of Reference Example 5.21 and chloroacetyl chloride according to a manner analogous to those of Example 3.1 in two steps via compound (a).

(a) (9S)-9-acetoxy-2-chloromethyl-9-ethyl-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.4 Hz, 3H), 1.06 (d, J=6.6 Hz, 6H), 1.67 (m, 2H), 1.89 (m, 1H), 2.06–2.63 (m, 2H), 2.21 (s, 3H), 4.07 (m, 2H), 4.44 (s, 2H), 5.27 (s, 2H), 5.39 (d, J=17.2 Hz, 1H), 5.66 (d, J=17.2 Hz, 1H), 7.10 (s, 1H), 7.17 (dd, J=2.0 and 6.6 Hz, 1H), 7.64–7.73 (m, 2H); MS (ES) m/z 549 (M$^+$+1).

(b) (9S)-2-chloromethyl-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (DMSO-d$_6$) 0.87 (t, J=7.4 Hz, 3H), 1.01 (d, J=5.9 Hz, 6H), 1.81–1.86 (m, 5H), 4.04 (m, 2H), 4.68 (s, 2H), 5.41 (s, 4H), 6.50 (s, 1H), 7.06 (dd, J=1.0 and 7.6 Hz, 1H), 7.21 (s, 1H), 7.55 (dd, J=1.0 and 8.6 Hz, 1H), 7.69 (dd, J=7.6 and 8.6 Hz, 1H); MS (ES) m/z 507 (M$^+$+1).

Example 4

Preparation of (9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H,15H)-dione trifluoroacetic acid The preparation method comprises of the following three steps via compounds (a) and (b).

(a) (9S)-9-acetoxy-2-(t-butoxycarbonylamino)methyl-9-ethyl-1-pentyl-1H,12H-pyrano[3",4":6',7']indolizino[1',2':6,5]pyrido[4,3,2-de]quinazoline-10,13(9H,15H)-dione To a solution of (9S)-9-amino-7-(pentylamino)camptothecin 20-acetate hydrochloride (53 mg mg, 0.1 mmol) of Reference Example 5.14 in dry dichloromethane (4 ml) were added Boc-glycine-OSu (150 mg), diisopropylethylamine (70 μl) and 4-N,N-dimethylaminopyridine (15 mg) at room temperature. The mixture was heated to reflux for 15 hr. in an oil bath. After cooling to room temperature, 1N aqueous hydrochloric acid (2 ml) was added to the reaction mixture and extracted with dichloromethane (20 ml). The dichloromethane layer was washed with brine, dried over MgSO$_4$ and concentrated under reduced pressure. The obtaining residue was purified by column chromatography to give pure product (56 mg, 89%).

$^1$H NMR (400 MHz) δ (CDCl$_3$) 0.93 (t, J=6.9 Hz, 3H), 0.97 (t, J=7.6 Hz, 3H), 1.35–1.50 (m, 4H), 1.51 (s, 9H), 1.68–1.80 (m, 2H), 2.10–2.30 (m, 2H), 2.21 (s, 3H), 3.88 (t, J=6.9 Hz, 2H), 4.33 (d, J=4.3 Hz, 2H), 5.27 (s, 2H), 5.38 (d, J=17.2 Hz, 1H), 5.65 (d, J=17.2 Hz, 1H), 5.98 (brs, 1H), 7.18 (dd, J=1.3 and 7.3 Hz, 1H), 7.20 (s, 1H), 7.60–7.71 (m, 2H); MS (ES) m/z 630 (M$^+$+1).

(b) (9S)-2-(t-butoxycarbonylamino)methyl-9-ethyl-9-hydroxy-1-pentyl-1H,12H-pyrano[3",4":6',7']indolizino[1',2':6,5]pyrido[4,3,2-de]quinazoline-10,13(9H,15H)-dione To a solution of (9S)-9-acetoxy-2-(t-butoxycarbonylamino)methyl-9-ethyl-1-pentyl-1H,12H-pyrano[3",4":6',7']indolizino[1',2':6,5]pyrido[4,3,2-de]quinazoline-10,13(9H, 15H)-dione (56 mg, 0.089 mmol) in methanol (2 ml) cooled in an ice-bath was added anhydrous hydrazine (50 μl) and the mixture was stirred for 1 hr. at room temperature. Concentrated hydrochloric acid solution (0.3 ml) was added dropwise to the reaction mixture with cooling in an ice-bath, and the mixture was stirred for 1 hr. at room temperature. The mixture was concentrated under reduced pressure. The residue was purified by column chromatography (dichloromethane/methanol=25/1) to give pure product (33 mg, 63%).

$^1$H NMR (400 MHz) δ (CDCl$_3$) 0.93 (t, J=7.3 Hz, 3H), 1.00 (t, J=7.3 Hz, 3H), 1.35–1.50 (m, 4H), 1.54 (s, 9H), 1.66–1.90 (m, 2H), 3.75 (m, 2H), 3.96 (brs, 1H), 4.27 (brd, 2H), 5.14 (s, 2H), 5.27 (d, J=16.2 Hz, 1H), 5.70 (d, J=16.2 Hz, 1H), 5.97 (s, 1H), 7.09 (d, J=7.3 Hz, 1H), 7.47 (s, 1H), 7.56–7.66 (m, 2H); MS (ES) m/z 588(M$^+$+1).

(c) (9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H,15H)-dione trifluoroacetic acid (9S)-2-(t-Butoxycarbonylamino)methyl-9-ethyl-9-hydroxy-1-pentyl-1H,12H-pyrano[3",4":6',7']indolizino[1',2':6,5]pyrido[4,3,2-de]quinazoline-10,13(9H,15H)-dione (33 mg, 0.056 mmol) was dissolved in trifluoroacetic acid (1 ml) and mixture was stirred for 1 hr. at room temperature. The solution was concentrated under reduced pressure and the resulting residue was purified by reverse-phase C-18 column chromatography to obtain pure product (27 mg, 80%).

$^1$H NMR (400 MHz) δ (DMSO-d$_6$) 0.87 (t, J=7.3 Hz, 3H), 0.92 (t, J=6.6 Hz, 3H), 1.34–1.44 (m, 4H), 1.74–1.90 (m, 4H), 3.89 (m, 2H), 4.23 (s, 2H), 5.39 (s, 2H), 5.42 (s, 2H), 6.51 (brs, 1H), 7.08 (d, J=7.6 Hz, 1H), 7.21 (s, 1H), 7.56 (d, J=8.3 Hz, 1H), 7.71 (dd, J=7.6 and 8.3 Hz, 1H), 7.97 (brs, 3H); MS (ES) m/z 488(M$^+$+1).

Example 5

Preparation of (9S)-9-ethyl-9-hydroxy-1-pentyl-2-trifluoromethyl-1H,12H-pyrano[3",4":6',7']indolizino[1',2':6,5]pyrido[4,3,2-de]quinazoline-10,13(9H,15H)-dione The preparation method comprises of the following two steps via compound (a).

(a) (9S)-9-acetoxy-9-ethyl-1-pentyl-2-trifluoromethyl-1H,12H-pyrano[3",4":6',7']indolizino[1',2':6,5]pyrido[4,3,2-de]quinazoline-10,13(9H,15H)-dione (20S)-9-Amino-7-(pentylamino)camptothecin 20-acetate hydrochloride (116 mg, 0.22 mmol) of Reference Example 5.14 was suspended in (CF$_3$CO)$_2$O (25 ml) and stirred for 3.5 h. After the mixture was concentrated under reduced pressure, the residue was suspended in aqueous 50%(v/v) EtOH solution (50 ml) and stirred under refluxing for 30 min. After being cooled to room temperature, the mixture was concentrated under reduced pressure. The residue was purified by column chromatography on silica gel (dichloromethane/acetone=7/1) to give pure product (109 mg, 81%).

$^1$H NMR (400 MHz) δ (CDCl$_3$) 0.92 (t, J=7.0 Hz, 3H), 0.98 (t, J=7.4 Hz, 3H), 1.30–1.50 (m, 4H), 1.65–1.78 (m, 2H), 2.09–2.34 (m, 2H), 2.21 (s, 3H), 3.95 (br, 2H), 5.18 and 5.23 (d, J=18.2 Hz, 1H×2), 5.39 and 5.65 (d, J=17.4 Hz, 1H×2), 7.11 (s, 1H), 7.25–7.35 (m, 1H), 7.68–7.79 (m, 2H); MS (ES) m/z 569 (M$^+$+1).

(b) (9S)-9-Ethyl-9-hydroxy-1-pentyl-2-trifluoromethyl-1H,12H-pyrano[3',4":6',7']indolizino[1',2':6,5]pyrido[4,3,2-de]quinazoline-10,13(9H,15H)-dione To a cold (0° C.) stirred solution of (9S)-9-acetoxy-9-ethyl-1-pentyl-2-trifluoromethyl-1H,12H-pyrano[3",4":6',7']indolizino[1',2':6,5]pyrido[4,3,2-de]quinazoline-10,13 (9H,15H)-dione (105 mg, 0.18 mmol) in MeOH (15 ml) was added anhydrous hydrazine (0.29 ml, 9.00 mmol). After being stirred at room temperature for 2 hr., the mixture was acidified with 10% HCl solution in MeOH at 0° C. and stirred at room temperature for 2 h. The mixture was filtered and washed with $CH_2Cl_2$. After the combined filtrate and washings were concentrated under reduced pressure, the residue was suspended in $CH_2Cl_2$ (30 ml). The mixture was filtered and washed with $CH_2Cl_2$. The combined filtrate and washings were concentrated under reduced pressure. The residue was purified by column chromatography on silica gel (dichloromethane/methanol=40/1-20/1) to give pure product (74.0 mg, 76%).

$^1$H NMR (270 MHz) δ (DMSO-$d_6$) 0.87 (2t, J=7.2 Hz, 3H×2), 1.27–1.45 (m, 4H), 1.66–1.95 (m, 4H), 3.88–4.03 (m, 2H), 5.33 (br, 2H), 5.42 (s, 2H), 6.58 (br, 1H), 7.19–7.28 (m, 1H), 7.23 (s, 1H), 7.65–7.81 (m, 2H); MS (ES) m/z 527 ($M^+$+1).

Example 6

Preparation of (9S)-2-(dimethylamino)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione Hydrochloride The preparation method comprises of the following two steps via compound (a).

(a) (9S)-9-acetoxy-2-(dimethylamino)-9-ethyl-1-(2-methylpropyl)-1H,12H-pyrano[3",4":6',7']indolizino[1',2':6,5]pyrido[4,3,2-de]quinazoline-10,13(9H,15H)-dione (20S)-9-amino-7-(2-methylpropylamino)camptothecin 20-acetate hydrochloride (13 mg, 0.02 mmol) of Reference Example 5.12 was suspended in dry dichloromethane (2 ml) and cooled in an ice-bath. NN-diisopropylethylamine (20 µl, 0.12 mmol) and phosgene iminium chloride (20 mg, 0.12 mmol) were added successively and the mixture was stirred for 1 hr. in an ice-bath and warmed to room temperature then stirred at room temperature for 1 day. The reaction mixture was poured into ice-water, and extracted with dichloromethane. The organic layer was washed with brine, dried over $MgSO_4$, and evaporated under reduced pressure. The residue obtained was purified by column chromatography (dichloromethane/acetone=10/1) to give S30 (8.7 mg, 70%) as a yellow powder.

$^1$H NMR (270 MHz) δ ($CDCl_3$) 0.84 (m, 6H), 0.96 (t, J=7.4 Hz, 3H), 1.81 (m, 1H), 2.10–2.32 (m, 2H), 2.21 (s, 3H), 2.94 (s, 6H), 3.80 (d, J=7.6 Hz, 2H), 5.01 (s, 2H), 5.40 (d, J=17.2 Hz, 1H), 5.67 (d, J=17.2H, 1H), 7.09 (dd, J=1.0 and 7.6 Hz, 1H), 7.14 (s, 1H), 7.54 (dd, J=1.0 and 8.6 Hz, 1H), 7.67 (dd, J=7.6 and 8.6 Hz, 1H); MS (ES) m/z 530 ($M^+$+1).

(b) (9S)-2-(dimethylamino)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione hydrochloride To a solution of (9S)-9-acetoxy-2-(dimethylamino)-9-ethyl-1-(2-methylpropyl)-1H,12H-pyrano[3",4":6',7']indolizino[1',2':6,5]pyrido[4,3,2-de]quinazoline-10,13(9H,15H)-dione (8.7 mg, 0.023 mmol) in methanol (2 ml) and 1,4-dioxane(2 ml) cooled in an ice-bath was added anhydrous hydrazine (100 µl). The mixture was warmed to room temperature and stirred for 3 hr. 10% HCl in methanol was added dropwise to acidify the reaction mixture and the mixture was stirred at room temperature for 2 h. After concentrated under reduced pressure, the obtaining residue was purified by reversed phase column chromatography (water/methanol=1/0-1/2) to give the product (7.4 mg, 85%) as a yellow powder.

$^1$H NMR (270 MHz) δ (DMSO-$d_6$) 0.75 (m, 6H), 0.88 (t, J=7.3 Hz, 3H), 1.79–1.90 (m, 3H), 2.92 (s, 6H), 3.83 (m, 2H), 5.11 (brs, 2H), 5.42 (s, 2H), 6.50 (brs, 1H), 6.94 (d, J=7.6 Hz, 1H), 7.23 (s, 1H), 7.41 (d, J=8.3 Hz, 1H), 7.63 (dd, J=7.6 and 8.3 Hz, 1H); MS (ES) m/z 488 ($M^+$+1).

Example 7.1

Preparation of (9S)-9-ethyl-9-hydroxy-1-(3-methylbutyl)-2(3H)-thioxo-1H,12H-pyrano[3",4":6',7']indolizino[1',2':6,5]pyrido[4,3,2-de]quinazoline-10,13 (9H,15H)-dione The preparation method comprises of the following two steps via compound (a).

(a) (9S)-9-acetoxy-9-ethyl-1-(3-methylbutyl)-2(3H)-thioxo-1H,12H-pyrano[3",4":6',7']indolizino[1'2':6,5]pyrido[4,3,2-de]quinazoline-10,13(9H,15H)-dione (20S)-9-amino-7-(3-methylbutylamino)camptothecin 20-acetate hydrochloride (378 mg, 0.67 mmol) of Reference Example 5.21 was suspended in dry dichloromethane (60 ml). N,N-diisopropylethylamine (333 µl, 1.91 mmol), 4-(dimethylamino)pyridine (156 mg, 1.27 mmol) and 1,1'-thiocarbonyl diimidazole (764 mg, 4.29 mmol) were added successively and the mixture was stirred at 50° C. for 6 hr. The reaction mixture was quenched with aqueous $NH_4Cl$ solution and extracted with dichloromethane. The organic layer was washed with brine, dried over $MgSO_4$, and evaporated under reduced pressure. The residue obtained was purified by column chromatography (dichloromethane/acetone=20/1) to give the product (257.5 mg, 72%) as a yellow powder.

$^1$H NMR (400 MHz) δ (DMSO-$d_6$, 120° C.) 0.96 (t, J=7.4 Hz, 3H), 1.05 (d, J=6.4 Hz, 6H), 1.77–1.87 (m, 3H), 2.13–2.21 (m, 2H), 2.19 (s, 3H), 4.69 (m, 2H), 5.45 (s, 2H), 5.50 (s, 2H), 6.96 (s, 1H), 6.98 (d, J=7.2 Hz, 1H), 7.50 (d, J=8.4 Hz, 1H), 7.64 (dd, J=7.2 and 8.4 Hz, 1H), 12.2 (brs, 1H); MS (ES) m/z 533 ($M^+$+1).

(b) (9S)-9-ethyl-9-hydroxy-1-(3-methylbutyl)-2 (3H)-thioxo-1H,12H-pyrano[3",4":6',7']indolizino[1',2':6,5]pyrido[4,3,2-de]quinazoline-10,13(9H,15H)-dione To a solution of (9S)-9-acetoxy-9-ethyl-1-(3-methylbutyl)-2(3H)-thioxo-1H,12H-pyrano[3",4":6',7']indolizino[1',2':6,5]pyrido[4,3,2-de]quinazoline-10,13(9H, 15H)-dione (63.1 mg, 0.12 mmol) in methanol (3 ml) and 1,4-dioxane (3 ml) was added anhydrous hydrazine (250 µl). The mixture was stirred at room temperature for 2 hr. 10% HCl in methanol was added dropwise to acidify the reaction mixture and the mixture was stirred at room temperature for 2 hr. After concentrated under reduced pressure, the obtaining residue was partitioned between dichloromethane and water.

The organic layer was concentrated under reduced pressure. The residue was purified by column chromatography (dichloromethane/methanol=50/1-10/1) to give the crude product, which was dissolved in dichloromethane (30 ml) and methanol (6 ml) mixed solvent. After evaporating under reduced pressure, the resulting precipitate was filtered and washed with cold methanol to give the product (33.4 mg, 57%) as a yellow powder.

$^1$H NMR (400 MHz) δ (DMSO-$d_6$, 99.6° C.) 0.89 (t, J=7.2 Hz, 3H), 1.02 (d, J=6.4 Hz, 6H), 1.75–1.90 (m, 5H), 4.68 (m, 2H), 5.35 (d, J=16.0 Hz, 1H), 5.43 (d, J=16.0 Hz, 1H), 5.48 (s, 2H), 6.13 (brs, 1H), 6.96 (d, J=8.0 Hz, 1H), 7.27 (s, 1H), 7.50 (d, J=8.8 Hz, 1H), 7.64 (dd, J=8.0 and 8.8 Hz, 1H), 12.24 (s, 1H); MS (ES) m/z 491 ($M^+$+1).

Example 7.2

Preparation of (9S)-9-ethyl-9-hydroxy-1-phenethyl-2(3H)-thioxo-1H,12H-pyrano[3",4":6',7']indolizino[1',2':6,5]pyrido[4,3,2-de]quinazoline-10,13(9H,15H)-dione This compound was prepared from (20S)-9-amino-7-(phenethylamino)camptothecin 20-acetate of Reference Example 5.5 according to a manner analogous to those of Example 7.1 in two steps via compound (a).

(a) (9S)-9-acetoxy-9-ethyl-1-phenethyl-2(3H)-thioxo-1H,12H-pyrano[3",4":6',7']indolizino[1',2':6,5]pyrido[4,3,2-de]quinazoline-10,13(9H,15H)-dione $^1$H NMR (400 MHz) δ (CDCl$_3$, 99.6° C.) 0.99 (t, J=7.6 Hz, 3H), 2.11–2.33 (m, 2H), 2.24 (s, 3H), 5.46 (d, J=17.3 Hz, 1H), 5.49 (d, J=17.8 Hz, 1H), 5.58 (d, J=17.8 Hz, 1H), 5.70 (d, J=17.3 Hz, 1H), 6.81 (dd, J=3.3 and 5.3 Hz, 1H), 7.17 (s, 1H), 7.20–7.42 (m, 5H), 7.64–7.71 (m, 2H), 9.78 (brs, 1H); MS (ES) m/z 567 ($M^+$+1).

(b) (9S)-9-ethyl-9-hydroxy-1-phenethyl-2(3H)-thioxo-1H,12H-pyrano[3",4":6',7']indolizino[1',2':6,5]pyrido[4,3,2-de]quinazoline-10,13(9H,15H)-dione $^1$H NMR (400 MHz) δ (DMSO-$d_6$, 99.5° C.) 0.90 (t, J=7.4 Hz, 3H), 1.89 (m, 2H), 3.19 (t, J=8.2 Hz, 2H), 4.87 (m, 2H), 5.36 (d, J=16.6 Hz, 1H), 5.44 (d, J=16.6 Hz, 1H), 5.56 (s, 2H), 6.12 (brs, 1H), 6.99 (d, J=7.6 Hz, 1H), 7.25 (m, 1H), 7.28 (s, 1H), 7.33 (m, 2H), 7.40 (d, J=8.0 Hz, 1H), 7.52 (d, J=8.4 Hz, 1H), 7.66 (dd, J=7.6 and 8.4 Hz, 1H); MS ES) m/z 525 ($M^+$+1).

Example 7.3

Preparation of (9S)-9-Ethyl-9-hydroxy-1-pentyl-2(3H)-thioxo-1H,12H-pyrano[3",4":6',7']indolizino[1',2':6,5]pyrido[4,3,2-de]quinazoline-10,13(9H,15H)-dione This compound was prepared from (20S)-9-amino-7-(pentylamino)camptothecin 20-acetate of Reference Example 5.14 according to a manner analogous to those of Example 7.1 in two steps via compound (a).

(a) (9S)-9-Acetoxy-9-ethyl-1-pentyl-2(3H)-thioxo-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.92 (t, J=7.0 Hz, 3H), 0.99 (t, J=7.3 Hz, 3H), 1.29–1.58 (m, 4H), 1.58–1.93 (m, 2H), 2.05–2.38 (m, 2H), 2.23 (s, 3H), 3.91–3.99 (m, 1H), 4.78–4.88 (m, 1H), 5.29–5.56 (m, 2H), 5.41 and 5.68 (d, J=17.3 Hz, 1H×2), 6.71–6.82 (m, 1H), 7.15 (s, 1H), 7.57–7.72 (m, 2H), 9.84–10.05 (m, 1H).

(b) (9S)-9-Ethyl-9-hydroxy-1-pentyl-2(3H)-thioxo-1H,12H-pyrano[3",4":6',7']indolizino[1',2':6,5]pyrido[4,3,2-de]quinazoline-10,13 (9H,15H)-dione $^1$H NMR (400 MHz) δ (DMSO-$d_6$, 120° C.) 0.90 (t, J=7.4 Hz, 3H), 0.92 (t, J=7.0 Hz, 3H), 1.32–1.50 (m, 4H), 1.72–1.98 (m, 4H), 4.63 (br, 2H), 5.34 and 5.43 (d, J=16.0 Hz, 1H×2), 5.44 (s, 2H), 6.00 (br, 1H), 6.97 (d, J=7.6 Hz, 1H), 7.28 (s, 1H), 7.49 (d, J=7.6 Hz, 1H), 7.63 (t, J=7.6 Hz, 1H), 12.1 (brs, 1H); MS (FAB) m/z 491 ($M^+$+1).

Example 8.1

Preparation of (9S)-9-ethyl-9-hydroxy-1-(3-methylbutyl)-2-methylthio-1H,12H-pyrano[3",4":6',7']indolizino[1',2':6,5]pyrido[4,3,2-de]quinazoline-10,13 (9H,15H)-dione The preparation method comprises of the following two steps via compound (a).

(a) (9S)-9-acetoxy-9-ethyl-1-(3-methylbutyl)-2-methylthio-1H,12H-pyrano[3",4":6',7']indolizino[1',2':6,5]pyrido[4,3,2-de]quinazoline-10,13(9H,15H)-dione (9S)-9-Acetoxy-9-ethyl-1-(3-methylbutyl)-2(3H)-thioxo-1H,12H-pyrano[3",4":6',7']indolizino[1',2':6,5]pyrido[4,3,2-de]quinazoline-10,13(9H,15H)-dione (190 mg, 0.36 mmol) of Example 7.1 (a) was dissolved in dry dichloromethane (10 ml) in a sealed tube. N,N-diisopropylethylamine (124 μl, 0.71 mmol), and methyl iodide (222 μl, 3.57 mmol) were added successively and the mixture was stirred at 50° C. for 2 hr. After concentrated under reduced pressure, the residue obtained was purified by column chromatography (dichloromethane/acetone=20/1) to give the product (184 mg, 94%) as a yellow powder.

$^1$H NMR (270 MHz) δ (CDCl$_3$) 0.96 (t, J=7.4 Hz, 3H), 1.06 (d, J=6.6 Hz, 6H), 1.69–1.77 (m, 2H), 1.88 (m, 1H), 2.06–2.34 (m, 2H), 2.21 (s, 3H), 2.61 (s, 3H), 4.05 (m, 2H), 5.28 (s, 2H), 5.39 (d, J=17.2 Hz, 1H), 5.66 (d, J=17.2H, 1H), 7.09 (m, 1H), 7.10 (s, 1H), 7.55 (dd, J=1.0 and 8.6 Hz, 1H), 7.65 (dd, J=7.6 and 8.6 Hz, 1H); MS (ES) m/z 547 ($M^+$+1).

(b) (9S)-9-ethyl-9-hydroxy-1-(3-methylbutyl)-2-methylthio-1H,12H-pyrano[3",4":6',7']indolizino[1',2':6,5]pyrido[4,3,2-de]quinazoline-10,13(9H,15H)-dione To a solution of (9S)-9-acetoxy-9-ethyl-1-(3-methylbutyl)-2-methylthio-1H,12H-pyrano[3",4":6',7']indolizino[1',2':6,5]pyrido[4,3,2-de]quinazoline-10,13(9H,15H)-dione (43.0 mg, 0.08 mmol) in methanol (2 ml) and 1,4-dioxane (2 ml) was added anhydrous hydrazine (200 μl). The mixture was stirred at room temperature for 2.5 hr. 10% HCl in methanol was added dropwise to acidify the reaction mixture and the mixture was stirred at room temperature for 2 hr. After concentrated under reduced pressure, the obtaining residue was partitioned between dichloromethane and water. The organic layer was concentrated under reduced pressure. The residue was purified by column chromatography (dichloromethane/methanol=100/1) to give the product (33.2 mg, 84%) as an orange powder.

$^1$H NMR (270 MHz) δ (DMSO-$d_6$) 0.87 (t, J=7.3 Hz, 3H), 1.02 (d, J=6.3 Hz, 6H), 1.69–1.90 (m, 5H), 2.57 (s, 3H), 4.06 (m, 2H), 5.41 (brs, 4H), 6.51 (brs, 1H), 6.85 (dd, J=1.0 and 7.6 Hz, 1H), 7.20 (s, 1H), 7.47 (dd, J=1.0 and 8.4 Hz, 1H), 7.65 (dd, J=7.6 and 8.4 Hz, 1H); MS (ES) m/z 505 (M$^+$+1).

Example 8.2

Preparation of (9S)-9-ethyl-2-ethylthio-9-hydroxy-1-(3-methylbutyl)-1H,12H-pyrano[3",4":6',7']indolizino[1',2':6,5]pyrido[4,3,2-de]quinazoline-10,13(9H,15H)-dione This compound was prepared from (9S)-9-acetoxy-9-ethyl-1-(3-methylbutyl)-2(3H)-thioxo-1H,12H-pyrano[3",4":6',7']indolizino[1', 2':6,5]pyrido[4,3,2-de]quinazoline-10,13(9H,15H)-dione of Example 7.1 (a) and ethyl iodide according to a manner analogous to those of Example 8.1 in two steps via compound (a).

(a) (9S)-9-acetoxy-9-ethyl-2-ethylthio-1-(3-methylbutyl)-1H,12H-pyrano[3",4":6',7']indolizino[1',2':6,5]pyrido[4,3,2-de]quinazoline-10,13(9H,15H)-dione $^1$H NMR (270 MHz) δ (CDCl$_3$) 0.96 (t, J=7.5 Hz, 3H), 1.06 (d, J=6.6 Hz, 6H), 1.43 (t, J=7.3 Hz, 3H), 1.64–1.75 (m, 2H), 1.86 (m, 1H), 2.03–2.34 (m, 2H), 2.21 (s, 3H), 3.22 (q, J=7.3 Hz, 2H), 4.01 (m, 2H), 5.26 (s, 2H), 5.39 (d, J=17.2 Hz, 1H), 5.66 (d, J=17.2H, 1H), 7.04 (dd, J=1.0 and 7.6 Hz, 1H), 7.09 (s, 1H), 7.52 (dd, J=1.0 and 8.6 Hz, 1H), 7.63 (dd, J=7.6 and 8.6 Hz, 1H); MS (ES) m/z 561 (M$^+$+1).

(b) (9S)-9-ethyl-2-ethylthio-9-hydroxy-1-(3-methylbutyl)-1H,12H-pyrano[3",4":6',7']indolizino[1', 2':6,5]pyrido[4,3,2-de]quinazoline-10,13(9H,15H)-dione $^1$H NMR (270 MHz) δ (DMSO-d$_6$) 0.87 (t, J=7.3 Hz, 3H), 1.01 (d, J=5.9 Hz, 6H), 1.36 (t, J=7.3 Hz, 3H), 1.68–1.91 (m, 5H), 3.19 (q, J=7.3 Hz, 2H), 4.01 (m, 2H), 5.36 (s, 2H), 5.41 (s, 2H), 6.50 (brs, 1H), 6.95 (d, J=7.6 Hz, 1H), 7.20 (s, 1H), 7.45 (d, J=8.6 Hz, 1H), 7.63 (dd, J=7.6 and 8.6 Hz, 1H); MS (ES) m/z 519 (M$^+$+1).

Example 9

Preparation of (9S)-2-(butylamino)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione hydrochloride The preparation method comprises of the following three steps via compounds (a) and (b).

(a) (9S)-9-acetoxy-9-ethyl-1-(3-methylbutyl)-2-methylsulfinyl-1H,12H-pyrano[3",4":6',7']indolizino[1', 2':6,5]pyrido[4,3,2-de]quinazoline-10,13(9H,15H)-dione To a solution of (9S)-9-acetoxy-9-ethyl-1-(3-methylbutyl)-2-methylthio-1H,12H-pyrano[3",4":6',7']indolizino[1', 2':6,5]pyrido[4,3,2-de]quinazoline-10,13(9H,15H)-dione (13.4 mg, 0.03 mmol) of Example 8.1 (a) in dichloromethane(1 ml) and methanol (0.2 ml) was added 0.25M OXONE in water (0.6 ml). The mixture was stirred at room temperature for 6 hr. After concentrated under reduced pressure, the obtaining residue was purified by column chromatography (dichloromethane/acetone=5/1) to give the product (6.4 mg, 46%) as a yellow powder.

$^1$H NMR (270 MHz) δ (CDCl$_3$) 0.98 (t, J=7.6 Hz, 3H), 1.05 (d, J=6.6 Hz, 6H), 1.71–1.92 (m, 3H), 2.09–2.31 (m, 2H), 2.22 (s, 3H), 3.09 (s, 3H), 3.77–4.36 (m, 2H), 5.27 (s, 2H), 5.39 (d, J=17.2 Hz, 1H), 5.66 (d, J=17.2H, 1H), 7.11 (s, 1H), 7.30 (m, 1H), 7.73 (m, 2H); MS (ES) m/z 563 (M$^+$+1).

(b) (9S)-9-acetoxy-2-(butylamino)-9-ethyl-1-(3-methylbutyl)-1H,12H-pyrano[3",4":6',7']indolizino[1',2':6,5]pyrido[4,3,2-de]quinazoline-10,13(9H, 15H)-dione To a solution of (9S)-9-acetoxy-9-ethyl-1-(3-methylbutyl)-2-methylsulfinyl-1H,12H-pyrano[3",4":6',7']indolizino[1',2':6,5]pyrido[4,3,2-de]quinazoline-10,13(9H,15H)-dione (6.4 mg, 0.01 mmol) in 1,4-dioxane (1.0 ml) was added n-butylamine (30 µl, 0.3 mmol). The mixture was stirred at 100° C. for 5 hr, and then stirred at room temperature for 2 days. After concentrated under reduced pressure, the obtaining residue was purified by column chromatography (dichloromethane/acetone=10/1) to give the product (5.4 mg, 83%) as a yellow powder.

$^1$H NMR (270 MHz) δ (CDCl$_3$) 0.91–1.06 (m, 12H), 1.40–1.69 (m, 6H), 1.81 (m, 1H), 2.10–2.29 (m, 2H), 2.21 (s, 3H), 3.49 (m, 2H), 3.79 (m, 2H), 4.34 (m, 1H), 5.25 (m, 2H), 5.39 (d, J=17.2 Hz, 1H), 5.66 (d, J=17.2H, 1H), 6.94 (m, 1H), 7.09 (s, 1H), 7.38 (m, 1H), 7.56 (m, 1H); MS (ES) m/z 572 (M$^+$+1).

(a) (9S)-2-(butylamino)-9-ethyl-9-hydroxy-1-(3-methylbutyl)-1H,12H-pyrano[3",4":6',7']indolizino[1',2':6,5]pyrido[4,3,2-de]quinazoline-10,13(9H, 15H)-dione hydrochloride To a solution of (9S)-9-acetoxy-2-butylamino-9-ethyl-1-(3-methylbutyl)-1H,12H-pyrano[3",4":6',7']indolizino[1',2':6,5]pyrido[4,3,2-de]quinazoline-10,13(9H,15H)-dione (5.4 mg, 0.01 mmol) in methanol (2 ml) was added anhydrous hydrazine (100 µl). The mixture was stirred at room temperature for 2 hr. 10% HCl solution in methanol was added dropwise to acidify the reaction mixture and the mixture was stirred at room temperature for 2 hr. After concentrated under reduced pressure, the obtaining residue was purified by reversed phase column chromatography (water/methanol=1/0–1/2) to give the product (2.8 mg, 56%) as a yellow powder.

$^1$H NMR (270 MHz) δ (DMSO-d$_6$) 0.87 (t, J=7.4 Hz, 3H), 0.94 (t, J=7.3 Hz, 3H), 0.97 (d, J=6.3 Hz, 6H), 1.29–1.45 (m, 2H), 1.55–1.65 (m, 4H), 1.72–1.92 (m, 3H), 3.28–3.41 (m, 2H), 4.01 (m, 2H), 5.38 (s, 2H), 5.41 (s, 2H), 6.47 (s, 1H), 6.71 (dd, J=1.0 and 7.6 Hz, 1H), 6.99 (m, 2H), 7.21 (m, 2H), 7.51 (dd, J=7.6 and 8.2 Hz, 1H); MS (ES) m/z 530 (M$^+$+1).

The following Examples illustrate pharmaceutical preparations containing a hexacyclic compound of the present invention i.e. (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione (Compound B)

Example A

Tablet Formulation

The following tablets may be prepared by conventional methods:

| Ingredient | mg/tablet | | |
|---|---|---|---|
| Compound of formula (1) | 5 | 25 | 100 |
| anhydrous lactose | 103 | 83 | 35 |
| croscarmellose | 6 | 6 | 8 |
| povidone K30 | 5 | 5 | 6 |
| magnesium stearate | 1 | 1 | 1 |
| Total weight | 120 | 120 | 150 |

Example B

Capsule Formulation

Interlocking gelatin capsules each containing the following ingredients were manufactured in a known manner:

| Ingredient | mg/capsule | | |
|---|---|---|---|
| Compound of formula (1) | 5 | 25 | 100 |
| anhydrous lactose | 103 | 83 | 35 |
| croscarmellose | 6 | 6 | 8 |
| povidone K30 | 5 | 5 | 6 |
| magnesium stearate | 1 | 1 | 1 |
| Total weight | 120 | 120 | 150 |

Example C

Injection Solution

The following solution may be prepared by methods known in the art:

| Ingredients | Mg/ml |
|---|---|
| Compound of formula (1) | 1 mg |
| Glycerol | 10–50 mg |
| Lecthin | 20–50 mg |
| Soy oil | 1.5 mg |
| Water | q.s. ml |

What is claimed is:

1. A method for treating a cancer comprising administering to a patient in need thereof a therapeutically effective amount of a compound according to a hexacyclic compound of formula (1B), wherein the cancer is colorectal cancer, lung cancer, breast cancer, stomach cancer, cervical cancer or bladder cancer

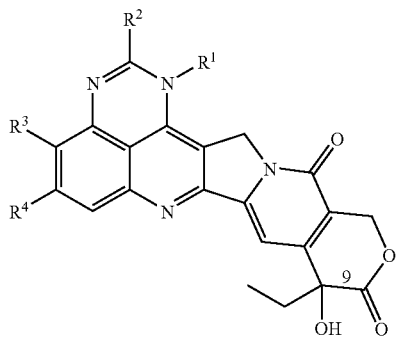

[1B]

wherein $R^1$ is hydrogen;
(C1–C10) alkyl, optionally substituted with one to three moieties independently selected from the group consisting of (C1–C5) alkoxy, hydroxyl, halogen, amino, mono-(C1–C5) alkylamino, di-(C1–C5) alkylamino and (C3–C7) cycloalkyl, a heterocyclic ring and aryl in which the aryl ring is optionally substituted with one to three moieties independently selected from the group consisting of hydroxy, alkoxy, halogen, amino, mono-(C1–C5) alkylamino and di-(C1–C5) alkylamino;

$R^2$ is hydrogen; amino; (C1–C5) alkyl, (C1–C5) alkoxy, (C1–C5) alkylthio, mono-(C1–C5) alkylamino, di-(C1–C5) alkylamino optionally substituted with one to three moieties independently selected from the group consisting of (C1–C5) alkoxy, hydroxy, halogen, amino, (C3–C7) cycloalkyl, heterocyclic ring or aryl in which the aryl ring is optionally substituted with one to three moieties independently selected from the group consisting of hydroxy, (C1–C5) alkoxy, amino, mono-(C1–C5) alkylamino or di-(C1–C5) alkylamino;

$R^3$ and $R^4$ are independently hydrogen, halogen or (C1–C5) alkyl;

or pharmaceutically acceptable salts thereof.

2. The method for treating a cancer according to claim 1, wherein $R^1$ is hydrogen;
(C1–C8) alkyl which is optionally substituted with one to three moieties independently selected from the group consisting of (C1–C3) alkoxy, hydroxy, halogen, amino, mono-(C1–C3) alkylamino, di-(C1–C3) alkylamino, (C3–C7) cycloalkyl, a heterocyclic ring and aryl in which the aryl ring is optionally substituted with one to three moieties independently selected from the group consisting of hydroxy, alkoxy and halogen;

$R^2$ is hydrogen;
amino;
(C1–C5) alkyl optionally substituted with one to three moieties independently selected from the group consisting of(C1–C5) alkoxy, hydroxy, halogen, amino, mono-(C1–C5) alkylamino, di-(C1–C5) alkylamino, (C3–C7) cycloalkyl, a heterocyclic ring and aryl; (C1–C5) alkylthio; (C1–C5) alkoxy; mono-(C1–C5) alkylamino; and di-(C1–C5) alkylamino;

$R^3$ is hydrogen or (C1–C3) alkyl; and
$R^4$ is hydrogen.

3. The method for treating a cancer according to claim 2, wherein $R^1$ is methyl, ethyl, n-propyl, 1-methylethyl, n-butyl, 1,1-dimethylethyl, 2-methylpropyl, 2,2-dimethylpropyl, n-pentyl, 3-methylbutyl, 2-n-hexyl, 3,3-dimethylbutyl, n-heptyl, n-octyl, benzyl, phenethyl, 2-(dimethylamino)ethyl, 2-(4-morpholino)ethyl, 3-(dimethylamino)propyl, 2-(pyridin-2-yl)ethyl, 2-(pyridin-3-yl)ethyl, 2-(4-methoxyphenyl)ethyl, 2-(4-chlorophenyl) ethyl or 2-(4-fluorophenyl)ethyl, 3-phenylpropyl;

$R^2$ is hydrogen, methyl, ethyl, propyl, hydroxymethyl, aminomethyl, (methylamino)methyl, (dimethylamino) methyl, chloromethyl, trifluoromethyl, phenyl, 2-pyridyl, methoxy, ethoxy, methylthio, ethylthio, methylamino, butylamino or dimethylamino;

$R^3$ hydrogen or methyl; and
$R^4$ hydrogen.

4. The method for treating a cancer according to claim 1, wherein the hexacyclic compound is selected from the group consisting of:

a) (9S)-1-butyl-9-ethyl-9-hydroxy-1H,12H-pyrano[3,"4": 6',7']indolizino[1',2':6,5]pyrido[4,3,2-de]quinazoline-10,13(9H,15H)-dione;

b) (9S)-9-ethyl-9-hydroxy-1-[2-(4-morpholino)ethyl]-1H,12H-pyrano[3,"4":6',7']indolizino[1',2':6,5]pyrido[4,3,2-de]quinazoline-10,13(9H,15H)-dione hydrochloride;
c) (9S)-9-ethyl-9-hydroxy-1-propyl-1H,12H-pyrano[3,"4":6',7']indolizino[1',2':6,5]pyrido[4,3,2-de]quinazoline-10,13(9H, 15H)-dione;
d) (9S)-1-benzyl-9-ethyl-9-hydroxy-1H,12H-pyrano[3,"4":6',7']indolizino[1',2':6,5]pyrido[4,3,2-de]quinazoline-10,13(9H,15H)-dione;
e) (9S)-9-ethyl-9-hydroxy-1-phenethyl-1H,12H-pyrano[3,"4":6',7']indolizino[1',2':6,5]pyrido[4,3,2-de]quinazoline-10,13(9H,15H)-dione;
f) (9S)-2,9-diethyl-9-hydroxy-1-phenethyl-1H,12H-pyrano[3,"4":6',7']indolizino[1',2':6,5]pyrido[4,3,2-de]quinazoline-10,13(9H,15H)-dione;
g) (9S)-9-ethyl-9-hydroxy-1-(3-phenylpropyl)-1H,12H-pyrano[3,"4":6',7']indolizino[1',2':6,5]pyrido[4,3,2-de]quinazoline-10,13(9H,15H)-dione;
h) (9S)-9-ethyl-9-hydroxy-1-(3-methylbutyl)-1H,12H-pyrano[3,"4":6',7']indolizino[1',2':6,5]pyrido[4,3,2-de]quinazoline-10,13(9H,15H)-dione;
i) (9S)-2,9-diethyl-9-hydroxy-1-(3-methylbutyl)-1H,12H-pyrano[3,"4":6',7']indolizino[1',2':6,5]pyrido[4,3,2-de]quinazoline-10,13(9H,15H)-dione; and
j) (9S)-2,9-diethyl-9-hydroxy-1-(2-methylpropyl)-1H,12H-pyrano[3,"4":6',7']indolizino[1',2':6,5]pyrido[4,3,2-de]quinazoline-10,13(9H,15H)-dione.

5. The method for treating a cancer according to claim 1, wherein the hexacyclic compound is selected from the group consisting of:
a) (9S)-9-ethyl-1-heptyl-9-hydroxy-1H,12H-pyrano[3,"4":6',7']indolizino[1',2':6,5]pyrido[4,3,2-de]quinazoline-10,13(9H,15H)-dione;
b) (9S)-9-ethyl-9-hydroxy-1-methyl-1H,12H-pyrano[3,"4":6',7']indolizino[1',2':6,5]pyrido[4,3,2-de]quinazoline-10,13(9H,15H)-dione;
c) (9S)-9-ethyl-9-hydroxy-1-(2-methylpropyl)-1H,12H-pyrano[3,"4":6',7']indolizino[1',2':6,5]pyrido[4,3,2-de]quinazoline-10,13(9H,15H)-dione;
d) (9S)-9-ethyl-1-hexyl-9-hydroxy-1H,12H-pyrano[3,"4":6',7']indolizino[1',2':6,5]pyrano[4,3,2-de]quinazoline-10,13(9H,15H)-dione;
e) (9S)-9-ethyl-9-hydroxy-1-pentyl-1H,12H-pyrano[3,"4":6',7']indolizino[1',2':6,5]pyrido[4,3,2-de]quinazoline-10,13(9H,15H)-dione;
f) (9S)-1,9-diethyl-9-hydroxy-1H,12H-pyrano[3,"4":6',7']indolizino[1',2':6,5]pyrido[4,3,2-de]quinazoline-10,13(9H,15H)-dione;
g) (9S)-9-ethyl-9-hydroxy-1-[2-(4-methoxyphenyl)ethyl]-1H,12H-pyrano[3,"4":6',7']indolizino[1',2':6,5]pyrido[4,3,2-de]quinazoline-10,13(9H,15H)-dione;
h) (9S)-1-[2-(4-chlorophenyl)ethyl]-9-ethyl-9-hydroxy-1H,12H-pyrano[3,"4":6',7']indolizino[1',2':6,5]pyrido[4,3,2- de]quinazoline-10,13(9H,15H)-dione;
i) (9S)-9-ethyl-1-[2-(4-fluorophenyl)ethyl]-9-hydroxy-1H,12H-pyrano[3,"4":6',7']indolizino[1',2':6,5]pyrido[4,3,2- de]quinazoline-10,13(9H,15H)-dione; and
j) (9S)-9-ethyl-1-[2-(4-fluorophenyl)ethyl]-9-hydroxy-2-methyl-1H,12H-pyrano[3,"4":6',7']indolizino[1',2':6,5]pyrido[4,3,2-de]quinazoline-10,13(9H,15H)-dione.

6. The method for treating a cancer according to claim 1, wherein the hexacyclic compound is selected from the group consisting of:
a) (9S)-9-ethyl-9-hydroxy-1-(1-methylethyl)-1H,12H-pyrano[3,"4":6',7']indolizino[1',2':6,5]pyrido[4,3,2-de]quinazoline-10,13(9H,15H)-dione;
b) (9S)-1-(3,3-dimethylbutyl)-9-ethyl-9-hydroxy-1H,12H-pyrano[3,"4":6',7']indolizino[1',2':6,5]pyrido[4,3,2-de]quinazoline-10,13(9H,15H)-dione;
c) (9S)-9-ethyl-9-hydroxy-2-methoxy-1-(3-methylbutyl)-1H,12H-pyrano[3,"4":6',7']indolizino[1',2':6,5]pyrido[4,3,2-de]quinazoline-10,13(9H,15H)-dione;
d) (9S)-2,9-diethyl-9-hydroxy-1-(3-methylbutyl)-1H,12H-pyrano[3,"4":6',7']indolizino[1',2':6,5]pyrido[4,3,2-de]quinazoline-10,13(9H,15H)-dione;
e) (9RS)-9-ethyl-9-hydroxy-4-methyl-1-pentyl-1H,12H-pyrano[3,"4":6',7']indolizino[1',2':6,5]pyrido[4,3,2-de]quinazoline-10,13(9H,15H)-dione;
f) (9S)-9-ethyl-9-hydroxy-1-(2-hydroxyethyl)-1H,12H-pyrano[3,"4":6',7']indolizino[1',2':6,5]pyrido[4,3,2-de]quinazoline-10,13(9H,15H)-dione;
g) (9S)-9-ethyl-9-hydroxy-1-(2-hydroxyethyl)-2-methyl-1H,12H-pyrano[3,"4":6',7']indolizino[1',2':6,5]pyrido[4,3,2-de]quinazoline-10,13(9H,15H)-dione;
h) (9S)-9-ethyl-9-hydroxy-2-methyl-1-pentyl-1H,12H-pyrano[3,"4":6',7']indolizino[1',2':6,5]pyrido[4,3,2-de]quinazoline-10,13(9H,15H)-dione;
i) (9S)-2,9-diethyl-9-hydroxy-1-pentyl-1H,12H-pyrano[3,"4":6',7']indolizino[1',2':6,5]pyrido[4,3,2-de]quinazoline-10,13(9H,15H)-dione; and
j) (9S)-9-ethyl-9-hydroxy-1-pentyl-2-propyl-1H,12H-pyrano[3,"4":6',7']indolizino[1',2':6,5]pyrido[4,3,2-de]quinazoline-10,13(9H,15H)-dione.

7. The method for treating a cancer according to claim 1, wherein the hexacyclic compound is selected from the group consisting of:
a) (9S)-9-ethyl-9-hydroxy-2-hydroxymethyl-1-pentyl-1H,12H-pyrano[3,"4":6',7']indolizino[1',2':6,5]pyrido[4,3,2-de]quinazoline-10,13(9H,15H)-dione;
b) (9S)-9-ethyl-9-hydroxy-2-hydroxymethyl-1-(2-methylpropyl)-1H,12H-pyrano[3,"4":6',7']indolizino[1',2':6,5]pyrido[4,3,2-de]quinazoline-10,13(9H,15H)-dione;
c) (9S)-9-ethyl-9-hydroxy-2-hydroxymethyl-1-(3-methylbutyl)-1H,12H-pyrano[3,"4":6',7']indolizino[1',2':6,5]pyrido[4,3,2-de]quinazoline-10,13(9H,15H)-dione;
d) (9S)-2-chloromethyl-9-ethyl-9-hydroxy-1-(3-methylbutyl)-1H,12H-pyrano[3,"4":6',7']indolizino[1',2':6,5]pyrido[4,3,2-de]quinazoline-10,13(9H,15H)-dione;
e) (9S)-2-aminomethyl-9-ethyl-9-hydroxy-1-pentyl-1H,12H-pyrano[3,"4":6',7']indolizino[1',2':6,5]pyrido[4,3,2-de]quinazoline-10,13(9H,15H)-dione;
f) (9S)-9-ethyl-9-hydroxy-1-pentyl-2-trifluoromethyl-1H,12H-pyrano[3,"4":6',7']indolizino[1',2':6,5]pyrido[4,3,2-de]quinazoline-10,13(9H,15H)-dione;
g) (9S)-9-ethyl-9-hydroxy-1-(3-methylbutyl)-2-methylthio-1H,12H-pyrano[3,"4":6',7']indolizino[1',2':6,5]pyrido[4,3,2-de]quinazoline-10,13(9H,15H)-dione;
h) (9S)-9-ethyl-2-ethylthio-9-hydroxy-1-(3-methylbutyl)-1H,12H-pyrano[3,"4":6',7']indolizino[1',2':6,5]pyrido[4,3,2-de]quinazoline-10,13(9H,15H)-dione;
i) (9S)-2-(dimethylamino)-9-ethyl-9-hydroxy-1-(2-methylpropyl)-1H,12H-pyrano[3,"4":6',7']indolizino[1',2':6,5]pyrido[4,3,2-de]quinazoline-10,13(9H,15H)-dione hydrochloride; and
j) (9S)-9-ethyl-9-hydroxy-1-(3-methylbutyl)-1H,12H-pyrano[3,"4":6',7']indolizino[1',2':6,5]pyrido[4,3,2-de]quinazoline-10,13(9H,15H)-dione hydrochloride.

* * * * *